(12) United States Patent
Jewett et al.

(10) Patent No.: US 11,673,921 B2
(45) Date of Patent: Jun. 13, 2023

(54) **CELL-FREE PROTEIN SYNTHESIS PLATFORM DERIVED FROM CELLULAR EXTRACTS OF *VIBRIO NATRIEGENS***

(71) Applicant: Northwestern University, Evanston, IL (US)

(72) Inventors: Michael Christopher Jewett, Evanston, IL (US); Benjamin James Des Soye, Evanston, IL (US); Samuel Ryan Davidson, Evanston, IL (US)

(73) Assignee: Northwestern University, Evanston, IL (US)

( * ) Notice: Subject to any disclaimer, the term of this patent is extended or adjusted under 35 U.S.C. 154(b) by 267 days.

(21) Appl. No.: 16/762,889

(22) PCT Filed: Nov. 12, 2018

(86) PCT No.: PCT/US2018/060279
§ 371 (c)(1),
(2) Date: May 8, 2020

(87) PCT Pub. No.: WO2019/094859
PCT Pub. Date: May 16, 2019

(65) Prior Publication Data
US 2021/0171584 A1    Jun. 10, 2021

Related U.S. Application Data

(60) Provisional application No. 62/584,406, filed on Nov. 10, 2017.

(51) Int. Cl.
| | | |
|---|---|---|
| C07K 14/28 | (2006.01) | |
| C07K 1/00 | (2006.01) | |
| C12N 1/20 | (2006.01) | |

(52) U.S. Cl.
CPC ............ *C07K 14/28* (2013.01); *C07K 1/00* (2013.01); *C12N 1/20* (2013.01)

(58) Field of Classification Search
CPC .............................. C07K 14/55; A61K 47/60
See application file for complete search history.

(56) References Cited

U.S. PATENT DOCUMENTS

| | | |
|---|---|---|
| 4,458,066 A | 7/1984 | Caruthers |
| 4,683,195 A | 7/1987 | Kary |
| 4,683,202 A | 7/1987 | Mullis |
| 5,494,810 A | 2/1996 | Barany |
| 6,994,986 B2 | 2/2006 | Swartz |
| 7,008,651 B2 | 3/2006 | Ambuel |
| 7,312,049 B2 | 12/2007 | Calhoun |
| 7,396,664 B2 | 7/2008 | Daly |
| 9,528,137 B2 | 12/2016 | Jewett |
| 9,951,392 B2 | 4/2018 | Jewett |
| 10,017,728 B2 | 7/2018 | Jewett |
| 10,118,950 B2 | 11/2018 | Jewett |
| 10,457,932 B2 | 10/2019 | Jewett |
| 10,465,221 B2 | 11/2019 | Jewett |
| 10,577,632 B2 | 3/2020 | Jewett |
| 10,590,456 B2 | 3/2020 | Jewett |
| 10,829,795 B2 | 11/2020 | Jewett |
| 2002/0058303 A1 | 5/2002 | Swartz |
| 2004/0038332 A1 | 2/2004 | Swartz |
| 2004/0209321 A1 | 10/2004 | Swartz |
| 2005/0032086 A1 | 2/2005 | Sakanyan |
| 2005/0064592 A1 | 3/2005 | Endo |
| 2005/0148046 A1 | 7/2005 | Endo |
| 2005/0186655 A1 | 8/2005 | Endo |
| 2007/0141661 A1 | 6/2007 | Endo |
| 2007/0154983 A1 | 7/2007 | Calhoun |
| 2008/0024821 A1 | 1/2008 | Silverbrook |
| 2008/0138857 A1 | 6/2008 | Swartz |
| 2008/0248521 A1 | 10/2008 | Knapp |
| 2009/0042244 A1 | 2/2009 | Voloshin |
| 2012/0088269 A1 | 4/2012 | Kusumegi |
| 2014/0295492 A1 | 10/2014 | Jewett |
| 2016/0060301 A1 | 3/2016 | Jewett |
| 2016/0083688 A1 | 3/2016 | Jewett |
| 2016/0362708 A1 | 12/2016 | Jewett |
| 2017/0073381 A1 | 3/2017 | Jewett |
| 2017/0292139 A1 | 10/2017 | Alfonta |
| 2017/0306320 A1 | 10/2017 | Jewett |
| 2017/0349928 A1 | 12/2017 | Jewett |
| 2018/0016612 A1 | 1/2018 | Jewett |
| 2018/0016614 A1 | 1/2018 | Jewett |
| 2018/0298416 A1 | 10/2018 | Jewett |
| 2019/0284600 A1 | 9/2019 | Jewett |

(Continued)

FOREIGN PATENT DOCUMENTS

| | | | |
|---|---|---|---|
| WO | 2016196940 A1 | 12/2016 | |
| WO | 2017172994 A1 | 10/2017 | |

OTHER PUBLICATIONS

Kamekura et al., "Effect of chloride and glutamate ions on in vitro protein synthesis by the moderate halophile Vibrio costicola", Journal of Bacteriology, vol. 160, No. 1, pp. 385-390, 1984 (Year: 1984).*

Choquet et al., "In vitro protein synthesis by the moderate halophile Vibrio costicola: Site of action of Cl-Ions", Journal of Bacteriology, vol. 171, No. 2, pp. 880-886, 1989 (Year: 1989).*

Martin et al., "High-ionic strength interference of ribosomal inhibition produced by aminoglycoside antibiotics", Biochemistry, vol. 34, pp. 16519-16523, 1995 (Year: 1995).*

Choquet et al., "Use of natural mRNAs in the cell-free protein-synthesizing systems of the moderate halophile Vibrio costicola", Journal of Bacteriology, vol. 172, No. 6, 1990 (Year: 1990).*

Wydro et al., "Salt-sensitive in vitro protein synthesis by a moderately halophilic bacterium", Nature, vol. 269, pp. 824-825, 1977 (Year: 1977).*

(Continued)

*Primary Examiner* — Tekchand Saidha
(74) *Attorney, Agent, or Firm* — Quarles & Brady LLP

(57) ABSTRACT

Disclosed are compositions, methods, and kits for performing cell-free RNA transcription and/or cell-free protein synthesis (CFPS). The disclosed compositions, methods, and kits include or utilize components prepared from *Vibrio* species such as cellular extracts from *Vibrio natriegens*.

21 Claims, 12 Drawing Sheets

Specification includes a Sequence Listing.

(56) References Cited

U.S. PATENT DOCUMENTS

| | | | |
|---|---|---|---|
| 2020/0010816 A1* | 1/2020 | Weinstock | C12P 21/00 |
| 2020/0270665 A1 | 8/2020 | Jewett | |
| 2021/0171584 A1* | 6/2021 | Jewett | C07K 14/28 |

OTHER PUBLICATIONS

Airen, I. O. Genome-wide functional genomic analysis for physiological investigation and improvement of cell-free protein synthesis PhD thesis, Stanford University, (2011).

Borja, G. M. et al. Engineering *Escherichia coli* to increase plasmid DNA production in high cell-density cultivations in batch mode. Microbial cell factories 11, 132, (2012).

Bundy, B. C. et al. Efficient disulfide bond formation in virus-like particles. Journal of biotechnology 154, 230-239, (2011).

Bundy, B. C. et al. Site-specific incorporation of p-propargyloxyphenylalanine in a cell-free environment for direct protein-protein click conjugation. Bioconjugate chemistry 21, 255-263, (2010).

Buntru, M., et al. A versatile coupled cell-free transcription-translation system based on tobacco BY-2 cell lysates. Biotechnology and bioengineering 112, 867-878, (2015).

Calhoun, K. A. et al. Total amino acid stabilization during cell-free protein synthesis reactions. Journal of biotechnology 123, 193-203, (2006).

Carlson, E. D., et al. "Cell-free protein synthesis: applications come of age." Biotechnology advances 30.5 (2012): 1185-1194.

Caschera, F. et al. Synthesis of 2.3 mg/ml of protein with an all *Escherichia coli* cell-free transcription-translation system. Biochimie 99, 162-168, (2014).

Chappell, J., et al. Validation of an entirely in vitro approach for rapid prototyping of DNA regulatory elements for synthetic biology. Nucleic acids research 41, 3471-3481, (2013).

Des Soye et al., "Establishing a High-Yielding Cell-Free Protein Synthesis Platform Derived from Vibrio natriegens," ACS Synth. Biol. Sep. 2018. 21;7(9):2245-2255.

Dudley, Q. M., et al. Cell-Free Mixing of *Escherichia coli* Crude Extracts to Prototype and Rationally Engineer High-Titer Mevalonate Synthesis. ACS synthetic biology 5, 1578-1588, (2016).

Failmezger, J., et al. Cell-free protein synthesis from non-growing, stressed *Escherichia coli*. Scientific reports 7, 16524, (2017).

Failmezger, J., et al. Cell-free protein synthesis from fast-growing Vibrio natriegens. Front Microbiol, (2018).

Harris, D. C., et al. "Cell-free biology: exploiting the interface between synthetic biology and synthetic chemistry." Current opinion in biotechnology 23.5 (2012): 672-678.

Hodgman, C. E. et al. Optimized extract preparation methods and reaction conditions for improved yeast cell-free protein synthesis. Biotechnology and bioengineering 110, 2643-2654, (2013).

Hodgman, C. E. et al. "Cell-free synthetic biology: thinking outside the cell." Metabolic engineering 14.3 (2012): 261-269.

Hong, S. H. et al. Improving cell-free protein synthesis through genome engineering of *Escherichia coli* lacking release factor 1. Chembiochem : a European journal of chemical biology 16, 844-853, (2015).

Huang, A. et al. BioBits Explorer: a modular synthetic biology education kit. Science Advances 4.8 (2018).

Hunt, J. P., et al. The growing impact of lyophilized cell-free protein expression systems. Bioengineered 8, 325-330, (2017).

International Searching Authority. International Search Report and Written Opinion for application PCT/US2018/060279, dated Feb. 28, 2019.

Jaroentomeechai, T. et al. Single-pot glycoprotein biosynthesis using a cell-free transcription-translation system enriched with glycosylation machinery. Nature communications 9, 2686, (2018).

Jewett, M. C. et al. Mimicking the *Escherichia coli* cytoplasmic environment activates long-lived and efficient cell-free protein synthesis. Biotechnology and bioengineering 86, 19-26, (2004).

Jewett, M. C. et al. An integrated cell-free metabolic platform for protein production and synthetic biology. Molecular systems biology 4, 220, (2008).

Jeweyy, M. C. et al. In vitro integration of ribosomal RNA synthesis, ribosome assembly, and translation. Molecular systems biology 9, 678, (2013).

Karig, D. K., et al. Preservation of protein expression systems at elevated temperatures for portable therapeutic production. Journal of the Royal Society, Interface 14, (2017).

Karim, A. S. et al. A cell-free framework for rapid biosynthetic pathway prototyping and enzyme discovery. Metabolic engineering 36, 116-126, (2016).

Kelwick, R., et al. Development of a Bacillus subtilis cell-free transcription-translation system for prototyping regulatory elements. Metabolic engineering 38, 370-381, (2016).

Kightlinger, W. et al. Design of glycosylation sites by rapid synthesis and analysis of glycosyltransferases. Nature chemical biology, (2018).

Kwon, Y. C. et al. High-throughput preparation methods of crude extract for robust cell-free protein synthesis. Scientific reports 5, 8663, (2015).

Lee, H. H. et al. Vibrio natriegens, a new genomic powerhouse. bioRxiv 058487, (2016).

Li, J. et al. Cell-free protein synthesis enables high yielding synthesis of an active multicopper oxidase. Biotechnology journal 11, 212-218, (2016).

Li, J., et al. Expanding the palette of Streptomyces-based cell-free protein synthesis systems with enhanced yields. Biochemical engineering journal 130, 29-33, (2018).

Li, J., et al. Establishing a high yielding streptomyces-based cell-free protein synthesis system. Biotechnology and bioengineering 114, 1343-1353, (2017).

Liu, D. V., et al. Streamlining *Escherichia coli* S30 extract preparation for economical cell-free protein synthesis. Biotechnology progress 21, 460-465, (2005).

Martin, R. W. et al. Cell-free protein synthesis from genomically recoded bacteria enables multisite incorporation of noncanonical amino acids. Nature communications 9, 1203, (2018).

Martin, R. W. et al. Development of a CHO-Based Cell-Free Platform for Synthesis of Active Monoclonal Antibodies. ACS synthetic biology 6, 1370-1379, (2017).

Moore, S. J. et al. Rapid acquisition and model-based analysis of cell-free transcription-translation reactions from nonmodel bacteria. Proceedings of the National Academy of Sciences of the United States of America 115, E4340-E4349, (2018).

Moore, S. J. et al. Streptomyces venezuelae TX-TL—a next generation cell-free synthetic biology tool. Biotechnology journal 12, (2017).

Mukai et al., "Highly reproductive *Escherichia coli* cells with no specific assignment to the UAG codon," Sci. Rep. May 18, 2015;5:9699.

Pardee, K. et al. Portable, On-Demand Biomolecular Manufacturing. Cell 167, 248-259 e212, (2016).

Pardee, K. et al. Rapid, Low-Cost Detection of Zika Virus Using Programmable Biomolecular Components. Cell 165, 1255-1266, (2016).

Penalber-Johnstone, C. et al. Optimizing cell-free protein expression in CHO: Assessing small molecule mass transfer effects in various reactor configurations. Biotechnology and bioengineering 114, 1478-1486, (2017).

Schoborg, J. A. et al. A cell-free platform for rapid synthesis and testing of active oligosaccharyltransferases. Biotechnology and bioengineering 115, 739-750, (2018).

Slomovic, S., et al. Synthetic biology devices for in vitro and in vivo diagnostics. Proceedings of the National Academy of Sciences of the United States of America 112, 14429-14435, (2015).

Smith, M. T., et al. Lyophilized *Escherichia coli*-based cell-free systems for robust, high-density, long-term storage. BioTechniques 56, 186-193, (2014).

Sullivan, C. J. et al. A cell-free expression and purification process for rapid production of protein biologics. Biotechnology journal 11, 238-248, (2016).

(56) References Cited

OTHER PUBLICATIONS

Swartz, J. R., et al. Cell-free protein synthesis with prokaryotic combined transcription-translation. Methods in molecular biology 267, 169-182, (2004).

Takahashi, M. K. et al. Characterizing and prototyping genetic networks with cell-free transcription-translation reactions. Methods 86, 60-72, (2015).

Wang, H., et al. Development of a Pseudomonas putida cell-free protein synthesis platform for rapid screening of gene regulatory elements. Synthetic Biology 3, ysy003-ysy003, (2018).

Weinstock, M. T., et al. "Vibrio natriegens as a fast-growing host for molecular biology." Nature methods 13.10 (2016): 849-851.

Zemella, A., et al. Cell-free protein synthesis: pros and cons of prokaryotic and eukaryotic systems. Chembiochem : a European journal of chemical biology 16, 2420-2431, (2015).

Kigawa, T et al. "Preparation of *Escherichia coli* cell extract for highly productive cell-free protein expression". Journal of Structural and Functional Genomics. Feb. 2004, 5, 63-68.

Liu, D et al. "Streamlining *Escherichia coli* S30 Extract Preparation for Economical Cell-Free Protein Synthesis". Biotechnol. Prog. 2005, 21, 460-465. Published on Web Dec. 22, 2004.

Sun, Z et al. "Protocols for Implementing an *Escherichia coli* Based TX-TL Cell-Free Expression System for Synthetic Biology". Journal of Visualized Experiments. Published Sep. 13, 2013.

Wada, A et al. "Structure and probable genetic location of a "ribosome modulation factor" associated with 100S ribosomes in stationary-phase *Escherichia coli* cells". Proc. Natl. Acad. Sci. Jan. 2, 1990, 87, 2657-2661.

\* cited by examiner

CELL-FREE PROTEIN SYNTHESIS PLATFORM DERIVED FROM CELLULAR EXTRACTS OF *VIBRIO NATRIEGENS*

CROSS-REFERENCE TO RELATED PATENT APPLICATIONS

The present application is the U.S. National Stage Entry of International Application PCT/US2018/060279, filed Nov. 12, 2018, which application claims the benefit of priority under 35 U.S.C. § 119(e) to U.S. Provisional Patent Application No. 62/584,406, filed on Nov. 10, 2017, the contents of which are incorporated herein by reference in their entireties.

STATEMENT REGARDING FEDERALLY SPONSORED RESEARCH OR DEVELOPMENT

This invention was made with government support under HR0011-15-C-0084 awarded by the Defense Advanced Research Projects Agency (DARPA). The government has certain rights in the invention.

BACKGROUND

The present invention generally relates to compositions, methods, and kits for performing cell-free RNA transcription and/or cell-free protein synthesis (CFPS). More specifically, the present invention relates to compositions, methods, and kits for performing cell-free RNA transcription and/or performing cell-free protein synthesis (CFPS) that include or utilize components prepared from naturally occurring or recombinant *Vibrio* species such as cellular extracts from *Vibrio natriegens*.

Cell-free protein synthesis (CFPS) is fueling numerous applications as a powerful in vitro expression system. Yet, in spite of significant improvements to system productivity and a rapid expansion of platform capabilities, widespread adoption of these technologies for various applications has been slow to materialize. This may be due, at least in part, to the relative difficulty in producing efficacious lysates, as this generally requires specialized equipment and expertise to consistently succeed.

In an effort to alleviate these requirements and lower the entry barrier into the use of CFPS systems, here we describe the development and characterization of a novel, facile CFPS platform based on lysates derived from the non-model bacterium *Vibrio natriegens*, which has been characterized as a fast-growing host for molecular biology and a genomic powerhouse. (See Weinstock et al., Nature Methods 13, 849-851, doi:10.1038/nmeth.3970 (2016); and Lee et al., bioRxiv, doi: 10.1101/058487 (Jun. 12, 2016); the contents of which are incorporated by reference in their entireties. Working with the wildtype strain, we identified the optimal culture media, temperature, and harvest time-point for the generation of highly-productive lysates. Next, we analyzed lysis conditions via sonication and discovered that *V. natriegens* cells are relatively agnostic to both cell pellet resuspension volume as well as sonication energy. Once optimal practices for producing lysates were established, we next looked to optimize the CFPS reagent mix specifically for use with *V. natriegens* lysates. By varying the concentrations of critical CFPS reaction substrates including salts, amino acids, and phosphoenol pyruvate, we identified an optimized reagent mix for *V. natriegens* CFPS. Our final optimized system is capable of synthesizing 1.6 g/L of superfolder green fluorescent protein in batch mode CFPS, making it competitive with existing bacterial CFPS platforms.

We applied our new platform to the successful synthesis of complex eukaryotic proteins including luciferase, an inactivated mutant diphtheria toxin, and an antibody fragment. We also demonstrate that lyophilized *V. natriegens* CFPS reactions assembled with a cryoprotectant retain ~100% productivity after being stored for a week at room temperature. Finally, to further increase the productivity of the system, we explored a small knockout library in which putative negative effectors of CFPS were genomically removed from the source strain. Our *V. natriegens*-derived platform is versatile, and simple to prepare and use. We expect it will facilitate expansion of CFPS systems into new laboratories and fields.

SUMMARY

Disclosed are compositions, methods, and kits for performing cell-free RNA transcription and/or performing cell-free protein synthesis (CFPS). The disclosed compositions, methods, and kits include or utilize components prepared from naturally occurring or recombinant *Vibrio* species such as cellular extracts from *Vibrio natriegens*.

DETAILED DESCRIPTION

Definitions and Terminology

Figure 1:
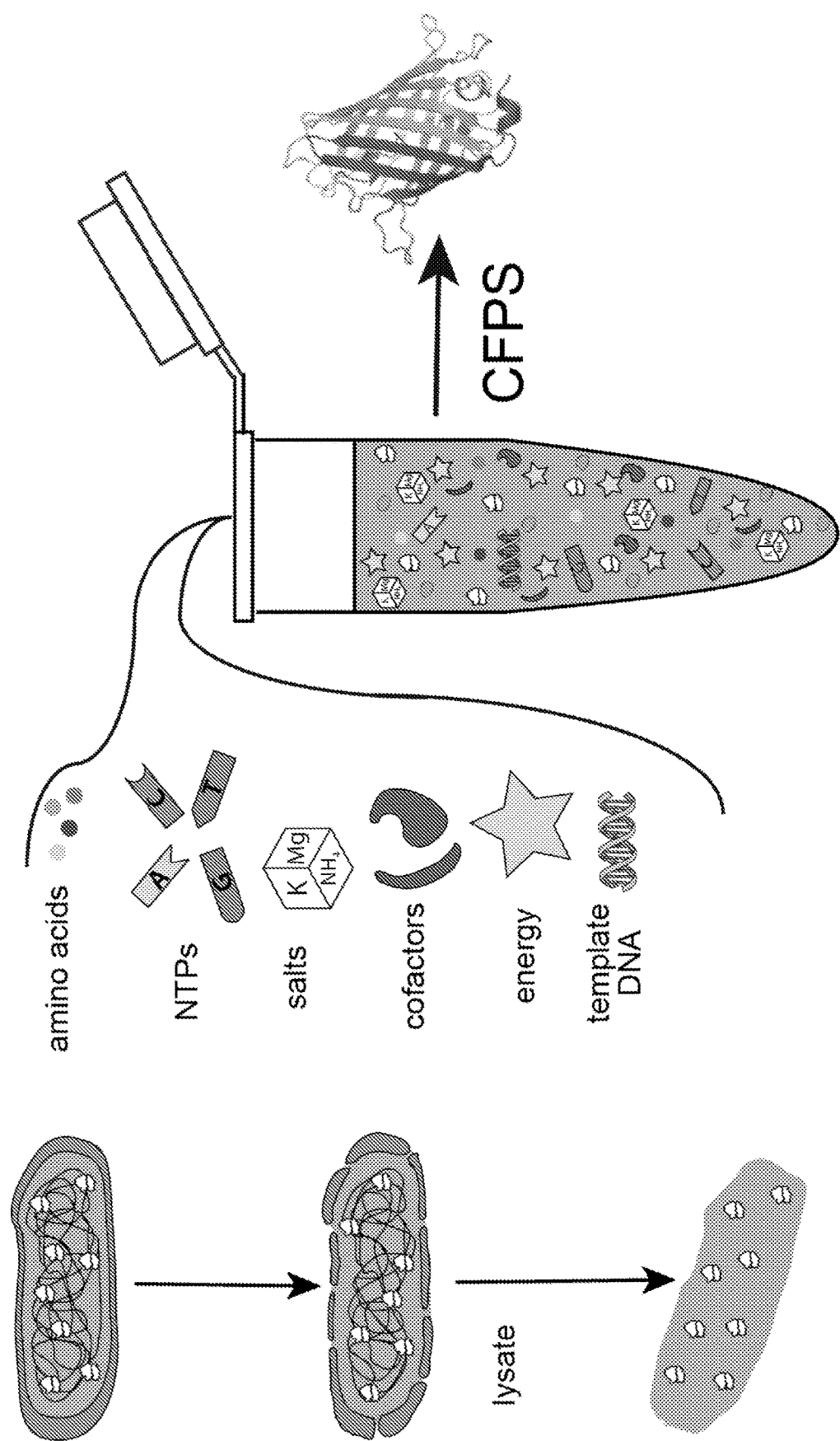
FIG. 1. Simplified schematic of the production and utilization of crude lysates from bacterial chassis cells to catalyze cell-free protein synthesis (CFPS). Reactions are supplemented with enzymatic cofactors, energy, and other substrates required for protein synthesis as well as plasmid DNA template directing the system towards the production of a product of interest.

The disclosed subject matter may be further described using definitions and terminology as follows. The definitions and terminology used herein are for the purpose of describing particular embodiments only, and are not intended to be limiting.

As used in this specification and the claims, the singular forms "a," "an," and "the" include plural forms unless the context clearly dictates otherwise. For example, the term "a component" should be interpreted to mean "one or more components" unless the context clearly dictates otherwise. As used herein, the term "plurality" means "two or more."

As used herein, "about", "approximately," "substantially," and "significantly" will be understood by persons of ordinary skill in the art and will vary to some extent on the context in which they are used. If there are uses of the term which are not clear to persons of ordinary skill in the art given the context in which it is used, "about" and "approximately" will mean up to plus or minus 10% of the particular term and "substantially" and "significantly" will mean more than plus or minus 10% of the particular term.

As used herein, the terms "include" and "including" have the same meaning as the terms "comprise" and "comprising." The terms "comprise" and "comprising" should be interpreted as being "open" transitional terms that permit the inclusion of additional components further to those components recited in the claims. The terms "consist" and "consisting of" should be interpreted as being "closed" transitional terms that do not permit the inclusion of additional components other than the components recited in the claims. The term "consisting essentially of" should be interpreted to be partially closed and allowing the inclusion only of additional components that do not fundamentally alter the nature of the claimed subject matter.

The phrase "such as" should be interpreted as "for example, including." Moreover the use of any and all exemplary language, including but not limited to "such as", is intended merely to better illuminate the invention and does not pose a limitation on the scope of the invention unless otherwise claimed.

Furthermore, in those instances where a convention analogous to "at least one of A, B and C, etc." is used, in general such a construction is intended in the sense of one having ordinary skill in the art would understand the convention (e.g., "a system having at least one of A, B and C" would include but not be limited to systems that have A alone, B alone, C alone, A and B together, A and C together, B and C together, and/or A, B, and C together.). It will be further understood by those within the art that virtually any disjunctive word and/or phrase presenting two or more alternative terms, whether in the description or figures, should be understood to contemplate the possibilities of including one of the terms, either of the terms, or both terms. For example, the phrase "A or B" will be understood to include the possibilities of "A" or 'B or "A and B."

All language such as "up to," "at least," "greater than," "less than," and the like, include the number recited and refer to ranges which can subsequently be broken down into subranges as discussed above.

A range includes each individual member. Thus, for example, a group having 1-3 members refers to groups having 1, 2, or 3 members. Similarly, a group having 6 members refers to groups having 1, 2, 3, 4, or 6 members, and so forth.

The modal verb "may" refers to the preferred use or selection of one or more options or choices among the several described embodiments or features contained within the same. Where no options or choices are disclosed regarding a particular embodiment or feature contained in the same, the modal verb "may" refers to an affirmative act regarding how to make or use and aspect of a described embodiment or feature contained in the same, or a definitive decision to use a specific skill regarding a described embodiment or feature contained in the same. In this latter context, the modal verb "may" has the same meaning and connotation as the auxiliary verb "can."

Polynucleotides and Synthesis Methods

The disclosed methods, devices, kits, and components may utilize and/or include polynucleotides. The terms "polynucleotide," "polynucleotide sequence," "nucleic acid" and "nucleic acid sequence" refer to a nucleotide, oligonucleotide, polynucleotide (which terms may be used interchangeably), or any fragment thereof. These phrases also refer to DNA or RNA of genomic, natural, or synthetic origin (which may be single-stranded or double-stranded and may represent the sense or the antisense strand).

The terms "nucleic acid" and "oligonucleotide," as used herein, refer to polydeoxyribonucleotides (containing 2-deoxy-D-ribose), polyribonucleotides (containing D-ribose), and to any other type of polynucleotide that is an N glycoside of a purine or pyrimidine base. There is no intended distinction in length between the terms "nucleic acid", "oligonucleotide" and "polynucleotide", and these terms will be used interchangeably. These terms refer only to the primary structure of the molecule. Thus, these terms include double- and single-stranded DNA, as well as double- and single-stranded RNA. For use in the present methods, an oligonucleotide also can comprise nucleotide analogs in which the base, sugar, or phosphate backbone is modified as well as non-purine or non-pyrimidine nucleotide analogs.

Regarding polynucleotide sequences, the terms "percent identity" and "% identity" refer to the percentage of residue matches between at least two polynucleotide sequences aligned using a standardized algorithm. Such an algorithm may insert, in a standardized and reproducible way, gaps in the sequences being compared in order to optimize alignment between two sequences, and therefore achieve a more meaningful comparison of the two sequences. Percent identity for a nucleic acid sequence may be determined as understood in the art. (See, e.g., U.S. Pat. No. 7,396,664, which is incorporated herein by reference in its entirety). A suite of commonly used and freely available sequence comparison algorithms is provided by the National Center for Biotechnology Information (NCBI) Basic Local Alignment Search Tool (BLAST), which is available from several sources, including the NCBI, Bethesda, Md., at its website. The BLAST software suite includes various sequence analysis programs including "blastn," that is used to align a known polynucleotide sequence with other polynucleotide sequences from a variety of databases. Also available is a tool called "BLAST 2 Sequences" that is used for direct pairwise comparison of two nucleotide sequences. "BLAST 2 Sequences" can be accessed and used interactively at the NCBI website. The "BLAST 2 Sequences" tool can be used for both blastn and blastp (discussed above).

Regarding polynucleotide sequences, percent identity may be measured over the length of an entire defined polynucleotide sequence, for example, as defined by a particular SEQ ID number, or may be measured over a shorter length, for example, over the length of a fragment taken from a larger, defined sequence, for instance, a fragment of at least 20, at least 30, at least 40, at least 50, at least 70, at least 100, or at least 200 contiguous nucleotides. Such lengths are exemplary only, and it is understood that any fragment length supported by the sequences shown herein, in the tables, figures, or Sequence Listing, may be used to describe a length over which percentage identity may be measured.

Regarding polynucleotide sequences, "variant," "mutant," or "derivative" may be defined as a nucleic acid sequence having at least 50% sequence identity to the particular nucleic acid sequence over a certain length of one of the nucleic acid sequences using blastn with the "BLAST 2 Sequences" tool available at the National Center for Biotechnology Information's website. (See Tatiana A. Tatusova, Thomas L. Madden (1999), "Blast 2 sequences—a new tool for comparing protein and nucleotide sequences", FEMS Microbiol Lett. 174:247-250). Such a pair of nucleic acids may show, for example, at least 60%, at least 70%, at least 80%, at least 85%, at least 90%, at least 91%, at least 92%, at least 93%, at least 94%, at least 95%, at least 96%, at least 97%, at least 98%, or at least 99% or greater sequence identity over a certain defined length.

Nucleic acid sequences that do not show a high degree of identity may nevertheless encode similar amino acid sequences due to the degeneracy of the genetic code where multiple codons may encode for a single amino acid. It is understood that changes in a nucleic acid sequence can be made using this degeneracy to produce multiple nucleic acid sequences that all encode substantially the same protein. For example, polynucleotide sequences as contemplated herein may encode a protein and may be codon-optimized for expression in a particular host. In the art, codon usage frequency tables have been prepared for a number of host organisms including humans, mouse, rat, pig, *E. coli*, plants, and other host cells.

Oligonucleotides can be prepared by any suitable method, including direct chemical synthesis by a method such as the phosphotriester method of Narang et al., 1979, Meth. Enzymol. 68:90-99; the phosphodiester method of Brown et al., 1979, Meth. Enzymol. 68:109-151; the diethylphosphoramidite method of Beaucage et al., 1981, Tetrahedron Letters 22:1859-1862; and the solid support method of U.S. Pat. No. 4,458,066, each incorporated herein by reference. A review of synthesis methods of conjugates of oligonucleotides and modified nucleotides is provided in Goodchild, 1990, Bioconjugate Chemistry 1(3): 165-187, incorporated herein by reference.

The term "amplification reaction" refers to any chemical reaction, including an enzymatic reaction, which results in increased copies of a template nucleic acid sequence or results in transcription of a template nucleic acid. Amplification reactions include reverse transcription, the polymerase chain reaction (PCR), including Real Time PCR (see U.S. Pat. Nos. 4,683,195 and 4,683,202; PCR Protocols: A Guide to Methods and Applications (Innis et al., eds, 1990)), and the ligase chain reaction (LCR) (see Barany et al., U.S. Pat. No. 5,494,810). Exemplary "amplification reactions conditions" or "amplification conditions" typically comprise either two or three step cycles. Two-step cycles have a high temperature denaturation step followed by a hybridization/elongation (or ligation) step. Three step cycles comprise a denaturation step followed by a hybridization step followed by a separate elongation step.

The terms "target," "target sequence", "target region", and "target nucleic acid," as used herein, are synonymous and refer to a region or sequence of a nucleic acid which is to be amplified, sequenced, or detected.

The term "hybridization," as used herein, refers to the formation of a duplex structure by two single-stranded nucleic acids due to complementary base pairing. Hybridization can occur between fully complementary nucleic acid strands or between "substantially complementary" nucleic acid strands that contain minor regions of mismatch. Conditions under which hybridization of fully complementary nucleic acid strands is strongly preferred are referred to as "stringent hybridization conditions" or "sequence-specific hybridization conditions". Stable duplexes of substantially complementary sequences can be achieved under less stringent hybridization conditions; the degree of mismatch tolerated can be controlled by suitable adjustment of the hybridization conditions. Those skilled in the art of nucleic acid technology can determine duplex stability empirically considering a number of variables including, for example, the length and base pair composition of the oligonucleotides, ionic strength, and incidence of mismatched base pairs, following the guidance provided by the art (see, e.g., Sambrook et al., 1989, Molecular Cloning—A Laboratory Manual, Cold Spring Harbor Laboratory, Cold Spring Harbor, N.Y.; Wetmur, 1991, Critical Review in Biochem. and Mol. Biol. 26(3/4):227-259; and Owczarzy et al., 2008, Biochemistry, 47: 5336-5353, which are incorporated herein by reference).

The term "primer," as used herein, refers to an oligonucleotide capable of acting as a point of initiation of DNA synthesis under suitable conditions. Such conditions include those in which synthesis of a primer extension product complementary to a nucleic acid strand is induced in the presence of four different nucleoside triphosphates and an agent for extension (for example, a DNA polymerase or reverse transcriptase) in an appropriate buffer and at a suitable temperature.

A primer is preferably a single-stranded DNA. The appropriate length of a primer depends on the intended use of the primer but typically ranges from about 6 to about 225 nucleotides, including intermediate ranges, such as from 15 to 35 nucleotides, from 18 to 75 nucleotides and from 25 to 150 nucleotides. Short primer molecules generally require cooler temperatures to form sufficiently stable hybrid complexes with the template. A primer need not reflect the exact sequence of the template nucleic acid, but must be sufficiently complementary to hybridize with the template. The design of suitable primers for the amplification of a given target sequence is well known in the art and described in the literature cited herein.

Primers can incorporate additional features which allow for the detection or immobilization of the primer but do not alter the basic property of the primer, that of acting as a point of initiation of DNA synthesis. For example, primers may contain an additional nucleic acid sequence at the 5' end which does not hybridize to the target nucleic acid, but which facilitates cloning or detection of the amplified product, or which enables transcription of RNA (for example, by inclusion of a promoter) or translation of protein (for example, by inclusion of a 5'-UTR, such as an Internal Ribosome Entry Site (IRES) or a 3'-UTR element, such as a $poly(A)_n$ sequence, where n is in the range from about 20 to about 200). The region of the primer that is sufficiently complementary to the template to hybridize is referred to herein as the hybridizing region.

As used herein, a primer is "specific," for a target sequence if, when used in an amplification reaction under sufficiently stringent conditions, the primer hybridizes primarily to the target nucleic acid. Typically, a primer is specific for a target sequence if the primer-target duplex stability is greater than the stability of a duplex formed between the primer and any other sequence found in the sample. One of skill in the art will recognize that various factors, such as salt conditions as well as base composition of the primer and the location of the mismatches, will affect the specificity of the primer, and that routine experimental confirmation of the primer specificity will be needed in many cases. Hybridization conditions can be chosen under which the primer can form stable duplexes only with a target sequence. Thus, the use of target-specific primers under suitably stringent amplification conditions enables the selective amplification of those target sequences that contain the target primer binding sites.

As used herein, a "polymerase" refers to an enzyme that catalyzes the polymerization of nucleotides. "DNA polymerase" catalyzes the polymerization of deoxyribonucleotides. Known DNA polymerases include, for example, *Pyrococcus furiosus* (Pfu) DNA polymerase, *E. coli* DNA polymerase I, T7 DNA polymerase and *Thermus aquaticus* (Taq) DNA polymerase, among others. "RNA polymerase" catalyzes the polymerization of ribonucleotides. The foregoing examples of DNA polymerases are also known as DNA-dependent DNA polymerases. RNA-dependent DNA polymerases also fall within the scope of DNA polymerases. Reverse transcriptase, which includes viral polymerases encoded by retroviruses, is an example of an RNA-dependent DNA polymerase. Known examples of RNA polymerase ("RNAP") include, for example, RNA polymerases of bacteriophages (e.g. T3 RNA polymerase, T7 RNA polymerase, SP6 RNA polymerase), and *E. coli* RNA polymerase, among others. The foregoing examples of RNA polymerases are also known as DNA-dependent RNA polymerase. The polymerase activity of any of the above enzymes can be determined by means well known in the art.

The term "promoter" refers to a cis-acting DNA sequence that directs RNA polymerase and other trans-acting transcription factors to initiate RNA transcription from the DNA template that includes the cis-acting DNA sequence.

As used herein, the term "sequence defined biopolymer" refers to a biopolymer having a specific primary sequence. A sequence defined biopolymer can be equivalent to a genetically-encoded defined biopolymer in cases where a gene encodes the biopolymer having a specific primary sequence. As used herein, "expression" refers to the process by which a polynucleotide is transcribed from a DNA template (such as into and mRNA or other RNA transcript) and/or the process by which a transcribed mRNA is subsequently translated into peptides, polypeptides, or proteins. Transcripts and encoded polypeptides may be collectively referred to as "gene product." If the polynucleotide is derived from genomic DNA, expression may include splicing of the mRNA in a eukaryotic cell.

As used herein, "expression template" refers to a nucleic acid that serves as substrate for transcribing at least one RNA that can be translated into a sequence defined biopolymer (e.g., a polypeptide or protein). Expression templates include nucleic acids composed of DNA or RNA. Suitable sources of DNA for use a nucleic acid for an expression template include genomic DNA, cDNA and RNA that can be converted into cDNA. Genomic DNA, cDNA and RNA can be from any biological source, such as a tissue sample, a biopsy, a swab, sputum, a blood sample, a fecal sample, a urine sample, a scraping, among others. The genomic DNA, cDNA and RNA can be from host cell or virus origins and from any species, including extant and extinct organisms. As used herein, "expression template" and "transcription template" have the same meaning and are used interchangeably.

In certain exemplary embodiments, vectors such as, for example, expression vectors, containing a nucleic acid encoding one or more rRNAs or reporter polypeptides and/or proteins described herein are provided. As used herein, the term "vector" refers to a nucleic acid molecule capable of transporting another nucleic acid to which it has been linked. One type of vector is a "plasmid," which refers to a circular double stranded DNA loop into which additional DNA segments can be ligated. Such vectors are referred to herein as "expression vectors." In general, expression vectors of utility in recombinant DNA techniques are often in the form of plasmids. In the present specification, "plasmid" and "vector" can be used interchangeably. However, the disclosed methods and compositions are intended to include such other forms of expression vectors, such as viral vectors (e.g., replication defective retroviruses, adenoviruses and adeno-associated viruses), which serve equivalent functions.

In certain exemplary embodiments, the recombinant expression vectors comprise a nucleic acid sequence (e.g., a nucleic acid sequence encoding one or more rRNAs or reporter polypeptides and/or proteins described herein) in a form suitable for expression of the nucleic acid sequence in one or more of the methods described herein, which means that the recombinant expression vectors include one or more regulatory sequences which is operatively linked to the nucleic acid sequence to be expressed. Within a recombinant expression vector, "operably linked" is intended to mean that the nucleotide sequence encoding one or more rRNAs or reporter polypeptides and/or proteins described herein is linked to the regulatory sequence(s) in a manner which allows for expression of the nucleotide sequence (e.g., in an in vitro ribosomal assembly, transcription and/or translation system). The term "regulatory sequence" is intended to include promoters, enhancers and other expression control elements (e.g., polyadenylation signals). Such regulatory sequences are described, for example, in Goeddel; Gene Expression Technology: Methods in Enzymology 185, Academic Press, San Diego, Calif. (1990).

The polynucleotide sequences contemplated herein may be present in expression vectors. For example, the vectors may comprise: (a) a polynucleotide encoding an ORF of a protein; (b) a polynucleotide that expresses an RNA that directs RNA-mediated binding, nicking, and/or cleaving of a target DNA sequence; and both (a) and (b). The polynucleotide present in the vector may be operably linked to a prokaryotic or eukaryotic promoter. "Operably linked" refers to the situation in which a first nucleic acid sequence is placed in a functional relationship with a second nucleic acid sequence. For instance, a promoter is operably linked to a coding sequence if the promoter affects the transcription or expression of the coding sequence. Operably linked DNA sequences may be in close proximity or contiguous and, where necessary to join two protein coding regions, in the same reading frame. Vectors contemplated herein may comprise a heterologous promoter (e.g., a eukaryotic or prokaryotic promoter) operably linked to a polynucleotide that encodes a protein. A "heterologous promoter" refers to a promoter that is not the native or endogenous promoter for the protein or RNA that is being expressed. Vectors as disclosed herein may include plasmid vectors.

Oligonucleotides and polynucleotides may optionally include one or more non-standard nucleotide(s), nucleotide analog(s) and/or modified nucleotides. Examples of modified nucleotides include, but are not limited to diaminopurine, $S^2T$, 5-fluorouracil, 5-bromouracil, 5-chlorouracil, 5-iodouracil, hypoxanthine, xantine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-D46-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, 2,6-diaminopurine and the like. Nucleic acid molecules may also be modified at the base moiety (e.g., at one or more atoms that typically are available to form a hydrogen bond with a complementary nucleotide and/or at one or more atoms that are not typically capable of forming a hydrogen bond with a complementary nucleotide), sugar moiety or phosphate backbone.

Peptides, Polypeptides, Proteins, and Synthesis Methods

The disclosed methods, devices, kits, and components may be utilized to synthesize proteins, polypeptides, and/or peptides. As used herein, the terms "protein" or "polypeptide" or "peptide" may be used interchangeable to refer to a polymer of amino acids. Typically, a "polypeptide" or "protein" is defined as a longer polymer of amino acids, of a length typically of greater than 50, 60, 70, 80, 90, or 100 amino acids. A "peptide" is defined as a short polymer of amino acids, of a length typically of 50, 40, 30, 20 or less amino acids.

As used herein, the terms "peptide," "polypeptide," and "protein," refer to molecules comprising a chain a polymer of amino acid residues joined by amide linkages. The term "amino acid residue," includes but is not limited to amino acid residues contained in the group consisting of alanine (Ala or A), cysteine (Cys or C), aspartic acid (Asp or D), glutamic acid (Glu or E), phenylalanine (Phe or F), glycine (Gly or G), histidine (His or H), isoleucine (Ile or I), lysine (Lys or K), leucine (Leu or L), methionine (Met or M), asparagine (Asn or N), proline (Pro or P), glutamine (Gln or Q), arginine (Arg or R), serine (Ser or S), threonine (Thr or T), valine (Val or V), tryptophan (Trp or W), and tyrosine (Tyr or Y) residues. The term "amino acid residue" also may include nonstandard, noncanonical, or unnatural amino acids, which optionally may include amino acids other than any of the following amino acids: alanine, cysteine, aspartic acid, glutamic acid, phenylalanine, glycine, histidine, isoleucine, lysine, leucine, methionine, asparagine, proline, glutamine, arginine, serine, threonine, valine, tryptophan, and tyrosine residues. The term "amino acid residue" may include alpha-, beta-, gamma-, and delta-amino acids.

In some embodiments, the term "amino acid residue" may include nonstandard, noncanonical, or unnatural amino acid residues contained in the group consisting of homocysteine, 2-Aminoadipic acid, N-Ethylasparagine, 3-Aminoadipic acid, Hydroxylysine, β-alanine, β-Amino-propionic acid, allo-Hydroxylysine acid, 2-Aminobutyric acid, 3-Hydroxyproline, 4-Aminobutyric acid, 4-Hydroxyproline, piperidinic acid, 6-Aminocaproic acid, Isodesmosine, 2-Aminoheptanoic acid, allo-Isoleucine, 2-Aminoisobutyric acid, N-Methylglycine, sarcosine, 3-Aminoisobutyric acid, N-Methylisoleucine, 2-Aminopimelic acid, 6-N-Methyllysine, 2,4-Diaminobutyric acid, N-Methylvaline, Desmosine, Norvaline, 2,2'-Diaminopimelic acid, Norleucine, 2,3-Diaminopropionic acid, Ornithine, and N-Ethylglycine. The term "amino acid residue" may include L isomers or D isomers of any of the aforementioned amino acids.

Other examples of nonstandard, noncanonical, or unnatural amino acids include, but are not limited, to a p-acetyl-L-phenylalanine, a p-iodo-L-phenylalanine, an O-methyl-L-tyrosine, a p-propargyloxyphenylalanine, a p-propargyl-phenylalanine, an L-3-(2-naphthyl)alanine, a 3-methyl-phenylalanine, an O-4-allyl-L-tyrosine, a 4-propyl-L-tyrosine, a tri-O-acetyl-GlcNAcpβ-serine, an L-Dopa, a fluorinated phenylalanine, an isopropyl-L-phenylalanine, a p-azido-L-phenylalanine, a p-acyl-L-phenylalanine, a p-benzoyl-L-phenylalanine, an L-phosphoserine, a phosphonoserine, a phosphonotyrosine, a p-bromophenylalanine, a p-amino-L-phenylalanine, an isopropyl-L-phenylalanine, an unnatural analogue of a tyrosine amino acid; an unnatural analogue of a glutamine amino acid; an unnatural analogue of a phenylalanine amino acid; an unnatural analogue of a serine amino acid; an unnatural analogue of a threonine amino acid; an unnatural analogue of a methionine amino acid; an unnatural analogue of a leucine amino acid; an unnatural analogue of a isoleucine amino acid; an alkyl, aryl, acyl, azido, cyano, halo, hydrazine, hydrazide, hydroxyl, alkenyl, alkynl, ether, thiol, sulfonyl, seleno, ester, thioacid, borate, boronate, 18ufa18hor, phosphono, phosphine, heterocyclic, enone, imine, aldehyde, hydroxylamine, keto, or amino substituted amino acid, or a combination thereof; an amino acid with a photoactivatable cross-linker; a spin-labeled amino acid; a fluorescent amino acid; a metal binding amino acid; a metal-containing amino acid; a radioactive amino acid; a photocaged and/or photoisomerizable amino acid; a biotin or biotin-analogue containing amino acid; a keto containing amino acid; an amino acid comprising polyethylene glycol or polyether; a heavy atom substituted amino acid; a chemically cleavable or photocleavable amino acid; an amino acid with an elongated side chain; an amino acid containing a toxic group; a sugar substituted amino acid; a carbon-linked sugar-containing amino acid; a redox-active amino acid; an α-hydroxy containing acid; an amino thio acid; an α,α disubstituted amino acid; a β-amino acid; a γ-amino acid, a cyclic amino acid other than proline or histidine, and an aromatic amino acid other than phenylalanine, tyrosine or tryptophan.

As used herein, a "peptide" is defined as a short polymer of amino acids, of a length typically of 20 or less amino acids, and more typically of a length of 12 or less amino acids (Garrett & Grisham, Biochemistry, $2^{nd}$ edition, 1999, Brooks/Cole, 110). In some embodiments, a peptide as contemplated herein may include no more than about 2, 3, 4, 5, 6, 7, 8, 9, 10, 11, 12, 13, 14, 15, 16, 17, 18, 19, or 20 amino acids. A polypeptide, also referred to as a protein, is typically of length ≥100 amino acids (Garrett & Grisham, Biochemistry, $2^{nd}$ edition, 1999, Brooks/Cole, 110). A polypeptide, as contemplated herein, may comprise, but is not limited to, 100, 101, 102, 103, 104, 105, about 110, about 120, about 130, about 140, about 150, about 160, about 170, about 180, about 190, about 200, about 210, about 220, about 230, about 240, about 250, about 275, about 300, about 325, about 350, about 375, about 400, about 425, about 450, about 475, about 500, about 525, about 550, about 575, about 600, about 625, about 650, about 675, about 700, about 725, about 750, about 775, about 800, about 825, about 850, about 875, about 900, about 925, about 950, about 975, about 1000, about 1100, about 1200, about 1300, about 1400, about 1500, about 1750, about 2000, about 2250, about 2500 or more amino acid residues.

A peptide as contemplated herein may be further modified to include non-amino acid moieties. Modifications may include but are not limited to acylation (e.g., O-acylation (esters), N-acylation (amides), S-acylation (thioesters)), acetylation (e.g., the addition of an acetyl group, either at the N-terminus of the protein or at lysine residues), formylation lipoylation (e.g., attachment of a lipoate, a C8 functional group), myristoylation (e.g., attachment of myristate, a C14 saturated acid), palmitoylation (e.g., attachment of palmitate, a C16 saturated acid), alkylation (e.g., the addition of an alkyl group, such as an methyl at a lysine or arginine residue), isoprenylation or prenylation (e.g., the addition of an isoprenoid group such as farnesol or geranylgeraniol), amidation at C-terminus, glycosylation (e.g., the addition of a glycosyl group to either asparagine, hydroxylysine, serine, or threonine, resulting in a glycoprotein). Distinct from glycation, which is regarded as a nonenzymatic attachment of sugars, polysialylation (e.g., the addition of polysialic acid), glypiation (e.g., glycosylphosphatidylinositol (GPI) anchor formation, hydroxylation, iodination (e.g., of thyroid hormones), and phosphorylation (e.g., the addition of a phosphate group, usually to serine, tyrosine, threonine or histidine).

The proteins disclosed herein may include "wild type" proteins and variants, mutants, and derivatives thereof. As used herein the term "wild type" is a term of the art understood by skilled persons and means the typical form of an organism, strain, gene or characteristic as it occurs in nature as distinguished from mutant or variant forms. As used herein, a "variant, "mutant," or "derivative" refers to a protein molecule having an amino acid sequence that differs from a reference protein or polypeptide molecule. A variant or mutant may have one or more insertions, deletions, or substitutions of an amino acid residue relative to a reference molecule. A variant or mutant may include a fragment of a reference molecule. For example, a mutant or variant molecule may one or more insertions, deletions, or substitution of at least one amino acid residue relative to a reference polypeptide.

Regarding proteins, a "deletion" refers to a change in the amino acid sequence that results in the absence of one or more amino acid residues. A deletion may remove at least 1, 2, 3, 4, 5, 10, 20, 50, 100, 200, or more amino acids residues. A deletion may include an internal deletion and/or a terminal deletion (e.g., an N-terminal truncation, a C-terminal truncation or both of a reference polypeptide). A "variant," "mutant," or "derivative" of a reference polypeptide sequence may include a deletion relative to the reference polypeptide sequence.

Regarding proteins, "fragment" is a portion of an amino acid sequence which is identical in sequence to but shorter in length than a reference sequence. A fragment may comprise up to the entire length of the reference sequence, minus at least one amino acid residue. For example, a fragment may comprise from 5 to 1000 contiguous amino acid residues of a reference polypeptide, respectively. In some embodiments, a fragment may comprise at least 5, 10, 15, 20, 25, 30, 40, 50, 60, 70, 80, 90, 100, 150, 250, or 500 contiguous amino acid residues of a reference polypeptide. Fragments may be preferentially selected from certain regions of a molecule. The term "at least a fragment" encompasses the full-length polypeptide. A fragment may include an N-terminal truncation, a C-terminal truncation, or both truncations relative to the full-length protein. A "variant," "mutant," or "derivative" of a reference polypeptide sequence may include a fragment of the reference polypeptide sequence.

Regarding proteins, the words "insertion" and "addition" refer to changes in an amino acid sequence resulting in the addition of one or more amino acid residues. An insertion or addition may refer to 1, 2, 3, 4, 5, 10, 20, 30, 40, 50, 60, 70, 80, 90, 100, 150, 200, or more amino acid residues. A "variant," "mutant," or "derivative" of a reference polypeptide sequence may include an insertion or addition relative to the reference polypeptide sequence. A variant of a protein may have N-terminal insertions, C-terminal insertions, internal insertions, or any combination of N-terminal insertions, C-terminal insertions, and internal insertions.

Regarding proteins, the phrases "percent identity" and "% identity," refer to the percentage of residue matches between at least two amino acid sequences aligned using a standardized algorithm. Methods of amino acid sequence alignment are well-known. Some alignment methods take into account conservative amino acid substitutions. Such conservative substitutions, explained in more detail below, generally preserve the charge and hydrophobicity at the site of substitution, thus preserving the structure (and therefore function) of the polypeptide. Percent identity for amino acid sequences may be determined as understood in the art. (See, e.g., U.S. Pat. No. 7,396,664, which is incorporated herein by reference in its entirety). A suite of commonly used and freely available sequence comparison algorithms is provided by the National Center for Biotechnology Information (NCBI) Basic Local Alignment Search Tool (BLAST), which is available from several sources, including the NCBI, Bethesda, Md., at its website. The BLAST software suite includes various sequence analysis programs including "blastp," that is used to align a known amino acid sequence with other amino acids sequences from a variety of databases.

Regarding proteins, percent identity may be measured over the length of an entire defined polypeptide sequence, for example, as defined by a particular SEQ ID number, or may be measured over a shorter length, for example, over the length of a fragment taken from a larger, defined polypeptide sequence, for instance, a fragment of at least 15, at least 20, at least 30, at least 40, at least 50, at least 70 or at least 150 contiguous residues. Such lengths are exemplary only, and it is understood that any fragment length supported by the sequences shown herein, in the tables, figures or Sequence Listing, may be used to describe a length over which percentage identity may be measured.

Regarding proteins, the amino acid sequences of variants, mutants, or derivatives as contemplated herein may include conservative amino acid substitutions relative to a reference amino acid sequence. For example, a variant, mutant, or derivative protein may include conservative amino acid substitutions relative to a reference molecule. "Conservative amino acid substitutions" are those substitutions that are a substitution of an amino acid for a different amino acid where the substitution is predicted to interfere least with the properties of the reference polypeptide. In other words, conservative amino acid substitutions substantially conserve the structure and the function of the reference polypeptide. The following table provides a list of exemplary conservative amino acid substitutions which are contemplated herein:

| Original Residue | Conservative Substitution |
|---|---|
| Ala | Gly, Ser |
| Arg | His, Lys |
| Asn | Asp, Gln, His |
| Asp | Asn, Glu |
| Cys | Ala, Ser |
| Gln | Asn, Glu, His |
| Glu | Asp, Gln, His |
| Gly | Ala |
| His | Asn, Arg, Gln, Glu |
| Ile | Leu, Val |
| Leu | Ile, Val |
| Lys | Arg, Gln, Glu |
| Met | Leu, Ile |
| Phe | His, Met, Leu, Trp, Tyr |
| Ser | Cys, Thr |
| Trp | Phe, Tyr |
| Tyr | His, Phe, Trp |
| Val | Ile, Leu, Thr |

Conservative amino acid substitutions generally maintain (a) the structure of the polypeptide backbone in the area of the substitution, for example, as a beta sheet or alpha helical conformation, (b) the charge or hydrophobicity of the molecule at the site of the substitution, and/or (c) the bulk of the side chain. Non-conservative amino acids typically disrupt (a) the structure of the polypeptide backbone in the area of the substitution, for example, as a beta sheet or alpha helical conformation, (b) the charge or hydrophobicity of the molecule at the site of the substitution, and/or (c) the bulk of the side chain.

The disclosed proteins, mutants, variants, or described herein may have one or more functional or biological activities exhibited by a reference polypeptide (e.g., one or more functional or biological activities exhibited by wild-type protein).

The disclosed proteins may be substantially isolated or purified. The term "substantially isolated or purified" refers to proteins that are removed from their natural environment, and are at least 60% free, preferably at least 75% free, and more preferably at least 90% free, even more preferably at least 95% free from other components with which they are naturally associated.

The proteins disclosed herein may be expressed from a "translation template." As used herein, "translation template" refers to an RNA product of transcription from an expression template that can be used by ribosomes to synthesize polypeptides or proteins.

The proteins disclosed herein may be expressed in a "reaction mixture." The term "reaction mixture," as used herein, refers to a solution containing reagents necessary to carry out a given reaction. A reaction mixture is referred to as complete if it contains all reagents necessary to perform the reaction. Components for a reaction mixture may be stored separately in separate container, each containing one or more of the total components. Components may be packaged separately for commercialization and useful commercial kits may contain one or more of the reaction components for a reaction mixture.

Cell-Free Protein Synthesis

Cell-free protein synthesis (CFPS) and methods for making cell extracts for use in CFPS are known in the art. (See, e.g., Carlson et al., "Cell-free protein synthesis: Applications come of age," Biotech. Adv. Vol. 30, Issue 5, September-October 2012, Pages 1185-1194; Hodgman et al., "Cell-free synthetic biology: Thinking outside the cell," Metabol. Eng. Vol. 14, Issue 3, May 2012, Pages 261-269; and Harris et al., "Cell-free biology: exploiting the interface between synthetic biology and synthetic chemistry," Curr. Op. Biotech. Vol. 23, Issue 5, October 2012, Pages 672-678; see also U.S. Pat. Nos. 7,312,049; 7,008,651; and 6,994,986; see also U.S. Published Application Nos. 20170306320; 20160362708; 20160060301; 20120088269; 20090042244; 2008024821; 20080138857; 20070154983; 20070141661; 20050186655; 200501480461 20050064592; 20050032086; 20040209321; and 20040038332; the contents of which are incorporated herein by reference in their entireties).

The disclosed compositions may include platforms for preparing a sequence defined biopolymer of protein in vitro. The platforms for preparing a sequence defined polymer or protein in vitro comprises a cellular extract from an organism, and in particular a species of *Vibrio*, such as *Vibrio natriegens*. Because CFPS exploits an ensemble of catalytic proteins prepared from the crude lysate of cells, the cell extract (whose composition is sensitive to growth media, lysis method, and processing conditions) is an important component of extract-based CFPS reactions. A variety of methods exist for preparing an extract competent for cell-free protein synthesis, including those disclosed in U.S. Published Application No. 20140295492, published on Oct. 2, 2014, which is incorporated by reference.

The platform may comprise an expression template, a translation template, or both an expression template and a translation template. The expression template serves as a substrate for transcribing at least one RNA that can be translated into a sequence defined biopolymer (e.g., a polypeptide or protein). The translation template is an RNA product that can be used by ribosomes to synthesize the sequence defined biopolymer. In certain embodiments the platform comprises both the expression template and the translation template. In certain specific embodiments, the platform may be a coupled transcription/translation ("Tx/Tl") system where synthesis of translation template and a sequence defined biopolymer from the same cellular extract.

The platform may comprise one or more polymerases capable of generating a translation template from an expression template. The polymerase may be supplied exogenously or may be supplied from the organism used to prepare the extract. In certain specific embodiments, the polymerase is expressed from a plasmid present in the organism used to prepare the extract and/or an integration site in the genome of the organism used to prepare the extract.

The platform may comprise an orthogonal translation system. An orthogonal translation system may comprise one or more orthogonal components that are designed to operate parallel to and/or independent of the organism's orthogonal translation machinery. In certain embodiments, the orthogonal translation system and/or orthogonal components are configured to incorporation of unnatural amino acids. An orthogonal component may be an orthogonal protein or an orthogonal RNA. In certain embodiments, an orthogonal protein may be an orthogonal synthetase. In certain embodiments, the orthogonal RNA may be an orthogonal tRNA or an orthogonal rRNA. An example of an orthogonal rRNA component has been described in U.S. Published Application Nos. 20170073381 and 20160060301, the contents of which are incorporated by reference in their entireties. In certain embodiments, one or more orthogonal components may be prepared in vivo or in vitro by the expression of an oligonucleotide template. The one or more orthogonal components may be expressed from a plasmid present in the genomically recoded organism, expressed from an integration site in the genome of the genetically recoded organism, co-expressed from both a plasmid present in the genomically recoded organism and an integration site in the genome of the genetically recoded organism, express in the in vitro transcription and translation reaction, or added exogenously as a factor (e.g., a orthogonal tRNA or an orthogonal synthetase added to the platform or a reaction mixture.

Platforms Comprising Extracts from *Vibrio* Species

The disclosed compositions (or systems) my include platforms for preparing a sequence defined biopolymer or protein in vitro, where the platform comprising a cellular extract prepared from a cell culture of a species of *Vibrio*. In particular, the species of *Vibrio* may include *Vibrio natriegens*.

The species of *Vibrio* may be a naturally occurring isolate (i.e., a wild-type species), or the species of *Vibrio* may be engineered. For example, the species of *Vibrio* may be engineered genetically to be deficient in a negative effector for cell-free protein synthesis (CFPS), for example via a knock-out mutation. Negative effectors for CFPS have been defined for *E. coli* and may include, but are not limited to, endA (SEQ ID NO:7), lon (SEQ ID NO:8), mazF (SEQ ID NO:9), ompT (SEQ ID NO:10), rna (SEQ ID NO:11), rnb (SEQ ID NO:12), glpK (SEQ ID NO:13), gor (SEQ ID NO:14), gshA (SEQ ID NO:15), tnaA (SEQ ID NO:16), rne (SEQ ID NO:31), gdhA (SEQ ID NO:32), sdaA (SEQ ID NO:33), sdaB (SEQ ID NO:34), speA (SEQ ID NO:35), WaaL (SEQ ID NO:36), and any combination thereof.

The species of *Vibrio* contemplated herein may be engineered to be deficient in a gene encoding the corresponding homolog of any of *E. coli* endA, mazF, rna, rnb, rne, gor, lon, ompT, gdhA, gshA, sdaA, sdaB, speA, WaaL, tnaA, glpK, and any combination thereof. For example, the species of *Vibrio* contemplated herein may be deficient in a gene which encodes the corresponding homolog of any of *E. coli* endA, mazF, rna, rnb, rne, gor, lon, ompT, gdhA, gshA, sdaA, sdaB, speA, WaaL, tnaA, glpK, which homolog has at least about 20%, 30%, 40%, 50%, 60%, 70%, 75%, 80%, 85%, 90%, 95%, 96%, 97%, 98%, or 99% amino acid sequence identity to one or more of endA (SEQ ID NO:7), lon (SEQ ID NO:8), mazF (SEQ ID NO:9), ompT (SEQ ID NO:10), rna (SEQ ID NO:11), rnb (SEQ ID NO:12), glpK (SEQ ID NO:13), gor (SEQ ID NO:14), gshA (SEQ ID NO:15), tnaA (SEQ ID NO:16), rne (SEQ ID NO:31), gdhA (SEQ ID NO:32), sdaA (SEQ ID NO:33), sdaB (SEQ ID NO:34), speA (SEQ ID NO:35), WaaL (SEQ ID NO:36), and any combination thereof.

In some embodiments, the species of *Vibrio* contemplated herein may be engineered to be deficient in one or more of Vnat_endA (SEQ ID NO:17), Vnat_lon (SEQ ID NO:18), Vnat_rnb (SEQ ID NO:19), Vnat_glpK (SEQ ID NO:20), Vnat_gor (SEQ ID NO:21), Vnat_gshA (SEQ ID NO:22), Vnat_tnaA (SEQ ID NO:23), or any combination thereof. In other embodiments, the species of *Vibrio* contemplated herein may be deficient in a gene encoding one or more of Vnat_endA (SEQ ID NO:24), Vnat_lon (SEQ ID NO:25), Vnat_rnb (SEQ ID NO:26), Vnat_glpK (SEQ ID NO:27), Vnat_gor (SEQ ID NO:28), Vnat_gshA (SEQ ID NO:29), Vnat_tnaA (SEQ ID NO:30), or any combination thereof.

In addition or in the alternative, the species of *Vibrio* may be engineered to express an upregulated gene product that is a positive effector for CFPS. Positive effectors for CFPS have been defined for *E. coli* and may include, but are not limited to ackA, ndk, pykF, cdd, dsbC, dnaK, dnaJ, crpE, tig, groS, groL, infA, infB, fusA, efp, lepA, tufB, hs1R, ffr, and any combination thereof. The species of *Vibrio* may be engineered genomically, for example by recombinantly introducing heterologous DNA into the genome of the species of *Vibrio*, and or the species of *Vibrio* may be engineered by introducing an episomal vector (e.g., a plasmid) to the species of *Vibrio* in order to create an engineered species of *Vibrio* that expresses an upregulated gene product that is the corresponding homolog of any of *E. coli* ackA, ndk, pykF, cdd, dsbC, dnaK, dnaJ, crpE, tig, groS, groL, infA, infB, fusA, efp, lepA, tufB, hs1R, ffr, and any combination thereof. For example, the species of *Vibrio* contemplated herein may be engineered to express an upregulated gene product that has an amino acid sequence having at least about 20%, 30%, 40%, 50%, 60%, 70%, 75%, 80%, 85%, 90%, 95%, 96%, 97%, 98%, or 99% amino acid sequence identity to one or more of *E. coli* ackA, ndk, pykF, cdd, dsbC, dnaK, dnaJ, crpE, tig, groS, groL, infA, infB, fusA, efp, lepA, tufB, hs1R, ffr, and any combination thereof.

The species of *Vibrio* may be engineered to be deficient specifically in a release factor of translation. Release factors for translation may include, but are not limited to release factor 1 (RF-1).

The species of *Vibrio* may be genomically-recoded. For example, the species of *Vibrio* may be genomically-recoded to replace one or more stop codons with a different codon, optionally where all of one stop codon is replaced in the genome of the species of *Vibrio* with a different codon.

The species of *Vibrio* may be engineered to express a non-native or heterologous RNA polymerase, for example, by recombinantly introducing heterologous DNA encoding the RNA polymerase into the genome of the species of *Vibrio*, and or the species of *Vibrio* may be engineered by introducing an episomal vector that expresses the RNA polymerase (e.g., a plasmid) to the species of *Vibrio*. Suitable RNA polymerases may include, but are not limited to T7 RNA polymerase.

The cellular extract of the platform is prepared from a cell culture of a species of *Vibrio*. In some embodiments, the cell culture is in stationary phase. In some embodiments, stationary phase may be defined as the cell culture having an $OD_{600}$ of greater than about 3.0, 3.5, 4.0, 4.5, 5.0, 5.5, 6.0, 6.5, 7.0, 7.5, 8.0, or having an $OD_{600}$ within a range bounded by any of these values.

The cell extract may be prepared by lysing the cells of the cell culture and isolating a fraction from the lysed cells. For example, the cell extract may be may be prepared by lysing the cells of the cell culture and subjecting the lysed cells to centrifugal force, and isolating a fraction after centrifugation (e.g., where the S12 fraction and/or S30 fraction is isolated).

The platforms disclosed herein may include additional components, for example, one or more components for performing CFPS. Components may include, but are not limited to amino acids which optionally may include non-canonical amino acids, NTPs, salts (e.g., sodium salts, potassium salts, and/or magnesium salts), cofactors (e.g., nicotinamide adenine dinucleotide (NAD) and/or coenzyme-A (CoA)), an energy source and optionally an energy source comprising a phosphate group (e.g., phosphoenol pyruvate (PEP), ATP, or creatine phosphate), a translation template (e.g., a non-native mRNA that is translated in the platform) and/or a transcription template (e.g., a template DNA for synthesizing a non-native mRNA that is translated in the platform), and any combination thereof.

In some embodiments, the platform may comprise an energy source and optionally an energy source comprising a phosphate group (e.g., phosphoenol pyruvate (PEP), ATP, or creatine phosphate), where the energy source is present in the platform at a concentration of greater than about 30 mM, 40 mM, 50 mM, 60 mM, 70 mM, 80 mM, or 90 mM (preferably greater than about 67 mM), but less than about 100 mM, or within a concentration range bounded by of these values.

In some embodiments, the platform further comprises a source of potassium ($K^+$)(such as a potassium salt such as potassium glutamate), where the platform comprises potassium at a concentration greater than about 50 mM, 100 mM, 150 mM, 200 mM, 250 mM, 300 mM, 350 mM, 400 mM, or 450 mM (preferably about 300 mM), but less than about 500 mM, or within a concentration range bounded by of these values, The disclosed platforms and cell extracts may be utilized in methods for preparing a sequence defined biopolymer or protein in vitro. The disclosed methods typically include translating in vitro a translation template (e.g., mRNA) encoding the sequence defined biopolymer or protein in the platform of any of the foregoing claims. Optionally, the disclosed methods may include transcribing a transcription template (e.g., DNA) in the platform to provide the translation template.

The disclosed methods may be performed under conditions that are suitable for cellular extracts prepared from a species of *Vibrio*. In some embodiments, the disclosed methods are performed at a temperature between about 20-40° C., and preferably at a temperature of about 30° C.

The disclosed methods may be performed to synthesize any sequence defined biopolymer or protein. In some embodiments, the sequence defined polymer or protein is a therapeutic protein and/or the method may utilized to identify therapeutic proteins or biomaterials by translating a library of transcription templates. In some embodiments, the disclosed methods may be performed to optimize in vitro translation conditions for a cellular extract prepared from a species of *Vibrio*.

Kits also are contemplated herein. In some embodiments, the contemplated kits comprise as components: (a) a cellular extract prepared from a cell culture of a species of *Vibrio* (e.g., *Vibrio natriegens*); and (b) a reaction mixture for translating an mRNA. Suitable components for the reaction mixture of the disclosed kits may include, but are not limited to, amino acids which optionally may include noncanonical amino acids, NTPs, salts (e.g., sodium salts, potassium salts, and/or magnesium salts), cofactors (e.g., nicotinamide adenine dinucleotide (NAD) and/or coenzyme-A (CoA)), an energy source and optionally an energy source comprising a phosphate group (e.g., ATP or creatine phosphate).

Knock-Out Mutations

The species of *Vibrio* disclosed herein may include a genetic knock-out mutation, preferably a knock-out mutation that downregulates or eliminates a negative protein effector for CFPS. In certain embodiments, the at least one additional genetic knock-out mutation improves DNA stability, RNA stability, protein stability, amino acid stability, energy supply, or any combination thereof. In certain embodiments, the at least one additional genetic knock-out mutation comprises 1, 2, 3, 4, or more than 4 genetic knock-out mutations. In embodiments where the strain comprises 2 or more genetic knock-out mutations, at least 2 of the genetic knock-out mutations may both improve the same attribute, improved DNA stability, improved RNA stability, improved protein stability, improved amino acid stability, improved energy supply, or may both improve different attributes.

To improve DNA or RNA stability, the at least one additional genetic knock-out mutation may target the functional inactivation of nucleases. In vivo, nucleases play important roles in regulating DNA and mRNA turnover. However, their presence in crude cell extracts is expected to be deleterious, leading to template instability and reaction termination. A nonexhaustive list of potential negative effectors that have been identified in *E. coli* follow: RNase A (encoded by ma) degrades RNA by catalyzing the cleavage of phosodiester bonds, and identification of strains (e.g., MRE600, A19) lacking ma was important for early studies in in vitro translation. RNase II (encoded by rnb) is responsible for mRNA decay by 3' to 5' exonuclease activity, and cell extracts lacking RNase II exhibit a 70% increase in CFPS efficiency. RNase E (encoded by me) is part of a cold shock degradosome that induces mRNA decay in cold shock, which the cells experience during harvest prior to extract generation. MazF (encoded by mazF) is a toxin that degrades mRNA by sequence-specific (ACA) endoribonuclease activity, which could affect transcript stability. CsdA (encoded by csdA) is part of a cold shock degradosome along with RNase E and induces mRNA decay in cold shock, which the cells experience during harvest prior to extract generation. DNA-specific endonuclease I (encoded by endA) breaks double-stranded DNA, and its deletion has previously shown to be important for extending the duration of CFPS reactions. The corresponding *Vibrio* homolog of these and other nucleases may be functionally inactivated by the at least on additional genetic knock-out mutation.

To improve protein stability, the at least one additional genetic knock-out mutation may target the functional inactivation of proteases. In vivo, these proteases play important roles in regulating protein turnover. However, their presence in CFPS reactions is expected to be deleterious, leading to protein instability issues. A nonexhaustive list of potential negative effectors identified in *E. coli* follow: Glutathione reductase (encoded by gor) reduces oxidized glutathione to maintain a reducing environment in the cytoplasm of a cell, making synthesis of disulfide-bonded proteins problematic. Lon (encoded by lon) is an ATP-dependent protease that demonstrated improved protein production in cell-free systems in BL21 strains upon transcriptional down regulation. Outer membrane protease VII (encoded by ompT) demonstrates specificity for paired basic residues and has been shown to stabilize proteins during CFPS upon removal. The corresponding *Vibrio* homolog of these and other proteases may be functionally inactivated by the at least on additional genetic knock-out mutation.

The at least one additional genetic knock-out mutation may target proteins known to negatively affect amino acid or energy supply. In vivo, these proteins play important roles in metabolism and substrate turnover. However, their presence in crude cell extracts is expected to be deleterious, leading to decreased amino acid and energy supply to support translation. A nonexhaustive list of potential negative effectors identified in *E. coli* follow. Glutamate dehydrogenase (encoded by gdhA) catalyzes the deamination of glutamate, which may affect glutamate's stability. Glutamate-cysteine-ligase (encoded by gshA) catalyzes the first step of glutathione synthesis and may decrease the stability of cysteine. Serine deaminase I (encoded by sdaA) and serine deaminase II (encoded by sdaB) are two of the three enzymes involved in serine degradation. Arginine decarboxylase (encoded by speA) consumes arginine in the biosynthetic production of putrescine. Tryptophanase (encoded by tnaA) consumes tryptophan in the production of indole. Lastly, glycerol kinase (encoded by glpK) consumes ATP to phosphorylate glycerol, which could help deplete the energy supply required for cell-free reactions. The corresponding *Vibrio* homolog of these and other proteins may be functionally inactivated by the at least on additional genetic knock-out mutation.

Strains having at least one additional genetic knock-out mutation, may be prepared by any method of engineering a strain to functionally inactivate the negative effector to lessen or eliminate the negative effector from a lysate prepared from the strain. In certain embodiments, the genetic knock-out mutations may be prepared by inserting either a nonsense mutation and/or a frameshift mutation into the genome of the strain as well as deleting a vital portion of a gene coding sequence. In certain embodiments, the genetic knock-out mutations may be prepared by removing regulatory sequences (i.e. promoter, ribosome binding site) or otherwise changing these sequences in the genome as to render them non-functional. In certain embodiments, negative effectors can be functionally knocked out in lysates by introducing a unique affinity tag and subsequently using the tag to selectively remove the effector protein from the lysates. In certain embodiments a strain having at least one additional genetic knock-out mutation may be prepared by multiplex automated genome engineering (MAGE), λ-Red recombinase-mediated recombination (Datsenko-Wanner), zinc-finger nucleases (ZFNs), transcription activator-like effector nucleases (TALENs), clustered regularly interspaced short palindromic repeats (CRISPR)-associated protein-9 nuclease (Cas9), and any other commonly used recombineering and genome engineering tools.

Upregulated Gene Products

The species of *Vibrio* disclosed herein may be engineered to express an additional upregulated gene product. The at least one additional upregulated gene product is preferably an upregulated gene product that is a positive effector for CFPS. In certain embodiments, the at least one additional upregulated gene product improves energy supply, chaperone levels, translations function, ribosome recycling, or any combination thereof. In certain embodiments, the at least on additional upregulated gene product comprises 1, 2, 3, 4, or more than 4 upregulated gene products. In embodiments where the strain comprises 2 or more upregulated gene products, at least 2 of the upregulated gene products may both improve the same attribute, improved energy supply, improved chaperone levels, improved translation function, or improved ribosome recycling, or may both improve different attributes.

To improve energy supply, the at least one additional upregulated gene product may target the upregulation of kinases. In vivo, these proteins play important roles in metabolism and the transfer of phosphate groups. The upregulated presence in crude cell extracts is expected to improve energy supply to support translation. A nonexhaustive list of potential positive effectors identified in *E. coli* follow. Acetate kinase (encoded by ackA) increases the overall metabolic flux of metabolites toward substrate-level ATP generation. Nucleoside-diphosphate kinase (encoded by ndk) facilitates the synthesis of NTPs from their corresponding NDPs. Pyruvate kinase monomer (encoded by pykF) helps drive ATP generation. The corresponding *Vibrio* homolog of these and other kinases may be the at least one additional upregulated gene product.

To improve energy supply, the at least one additional upregulated gene product may target the upregulate of deaminases. In vivo, these proteins may play important roles in metabolism and preparing metabolites. A nonexhaustive list of potential positive effectors identified in *E. coli* follow. Cytidine deaminase (encoded by cdd) initiates the deamination of cytidine which may lead to the synthesis of UTP. The corresponding *Vibrio* homolog of these and other deaminases may be the at least one additional upregulated gene product.

To improve chaperone levels, the at least one upregulated gene product may target the upregulation of isomerases, foldases and/or holdases. In vivo, these proteins may play important roles in the assisting proteins to adopt functionally active conformations. The upregulated presence in crude cell extracts is expected to improve chaperone levels to support protein production into soluble and/or active confirmations. A nonexhaustive list of potential positive effectors identified in *E. coli* follow. Disulfide bond isomerase (encoded by dsbC) shuffles disulfide bonds into correct positions. Chaperone protein DnaK (encoded by dnaK) aids the folding of nascent polypeptide chains and the rescue of misfolded proteins. Chaperone protein DnaJ (encoded by dnaJ) stimulates the ATPase activity of DnaK. Protein GrpE (encoded by grpE) stimulates the ATPas activity of DnaK. Trigger Factor (encoded by tig) aids the folding of nascent polypeptides. The 10 kDa chaperonin subunit (encoded by groS) forms part of the GroEL-GroES chaperonin complex that aids in protein folding. The 60 kDa chaperonin subunit (encoded by groL) forms part of the GroEL-GroES chaperonin complex that aids in protein folding. The corresponding *Vibrio* homolog of these and other isomerases, foldases, and/or holdases may be the at least one additional upregulated gene product.

To improve translation function, the at least one upregulated gene product may target the upregulation of initiation factors and/or elongation factors. In vivo, these proteins play important roles in the translation function. The upregulated presence in crude cell extracts is expected to improve translation function. A nonexhaustive list of potential positive effectors identified in *E. coli* follow. Translation initiation factor IF-1 (encoded by infA) interacts with the 30S ribosomal subunit to initiate translations. Translation initiation faction IF-2 (encoded by infB) has a role in the proper placement of the charged initiator fMet-tRNA via a GTP-dependent mechanism. Elongation factor G (encoded by fusA) facilitates translocation of the ribosome by one codon along a mRNA. Elongation factor P (encoded by efp) stimulates the synthesis of peptide bonds. Elongation factor 4 (encoded by lepA) can alter the rate of translation, leading to increases in the rate of translation under certain stress conditions. Elongation factor TU 2 (encoded by tufB) helps shuttle charged tRNAs to ribosomes. The corresponding *Vibrio* homolog of these and other initiation factors and/or elongation factors may be the at least one additional upregulated gene product.

To improve translation function, the at least one upregulated gene product may target the upregulation of recycling factors. In vivo, these proteins play important roles in the ribosome recycling. The upregulated presence in crude cell extracts is expected to improve ribosome recycling. A nonexhaustive list of potential positive effectors identified in *E. coli* follow. Heat shock protein 15 (encoded by hslR) is involved with the recycling of free 50S ribosomal subunits. Ribosome-recycling factor (encoded by frr) promotes rapid recycling of ribosomal subunits after the release of the polypeptide chain. The corresponding *Vibrio* homolog of these and other recycling factors may be the at least one additional upregulated gene product.

Strains having at least one additional genetic knock-out mutation, may be prepared by any method of engineering a strain to functionally increase a positive effector to increase the presence of the positive effector in the lysate prepared from the strain. In certain embodiments, the upregulated gene product is expressed from a plasmid present in the GRO and/or expressed from an integration site in GRO genome. Additionally, gene upregulation may be enhanced by engineering the promoter and/or ribosome binding site in front of your gene of interest located either on a plasmid or on the genome. A stronger promoter/ribosome binding site would lead to an increase in transcriptional activity. Techniques commonly employed to integrate a plasmid overexpressing a positive effector into a strain includes transformation. Techniques commonly employed to integrate a gene cassette containing a positive effector into the genome for overexpression includes X-Red recombinase-mediated recombination (Datsenko-Wanner).

Genomically Recoded Organisms

An aspect of the present invention is a genomically recoded organism (GRO) which optionally may be a strain deficient in release factor 1 (RF1) or a genetic homolog thereof. GROs may be prepared by any method of strain engineering. In certain embodiments, a strain deficient in RF1 is prepared by replacing in the strain all instances of the UAG codon, permitting the deletion of release factor 1 (RF1; terminates translation at UAG and UAA) and, hence, eliminating translational termination at UAG codons. This GRO allows for the reintroduction of UAG codons, along with orthogonal translation machinery to permit efficient and site-specific incorporation of nonstandard or noncanonical amino acids into proteins. That is, UAG may be transformed from a nonsense codon (terminates translation) to a sense codon (incorporates amino acid of choice), provided the appropriate translation machinery is present.

ILLUSTRATIVE EMBODIMENTS

The following embodiments are illustrative and should not be interpreted to limit the scope of the claimed subject matter.

Embodiment 1

A platform for preparing mRNA, a sequence defined biopolymer, a peptide (e.g., an amino acid sequence of 5-100 residues), or a polypeptide in vitro, the platform comprising a cellular extract prepared from a cell culture of a species of *Vibrio*.

Embodiment 2

The platform of embodiment 1, wherein the species of *Vibrio* is *Vibrio natriegens*.

Embodiment 3

The platform of embodiment 1 or 2, wherein the species of *Vibrio* is engineered to be deficient in a negative effector for cell-free protein synthesis (CFPS).

Embodiment 4

The platform of embodiment 3, wherein the negative effector for CFPS is selected from the group consisting of the *Vibrio* homolog of *E. coli* endA, mazF, rna, rnb, rne, gor, lon, ompT, gdhA, gshA, sdaA, sdaB, speA, WaaL, tnaA, glpK, and any combination thereof.

Embodiment 5

The platform of any of the foregoing embodiments, wherein the species of *Vibrio* is engineered to express an upregulated gene product that is a positive effector for CFPS.

Embodiment 6

The platform of embodiment 5, wherein the positive effector for CFPS is selected from the group consisting of the *Vibrio* homolog of *E. coli* ackA, ndk, pykF, cdd, dsbC, dnaK, dnaJ, crpE, tig, groS, groL, infA, infB, fusA, efp, lepA, tufB, hs1R, ffr, and any combination thereof.

Embodiment 7

The platform of any of the foregoing embodiments, wherein the species of *Vibrio* is engineered to be deficient in a release factor 1.

Embodiment 8

The platform of any of the foregoing embodiments, wherein the species of *Vibrio* has been engineered to express T7 RNA polymerase.

Embodiment 9

The platform of any of the foregoing embodiments, wherein the cell culture are in stationary phase.

Embodiment 10

The platform of embodiment 9, wherein stationary phase is defined as the cell culture having an $OD_{600}$ of greater than about 3.0.

Embodiment 11

The platform of any of the foregoing embodiments, wherein the cellular extract comprises an S12 fraction and/or S30 fraction of the cell culture.

Embodiment 12

The platform of any of the foregoing embodiments further comprising one or more components selected from the group consisting of amino acids which optionally may include non-canonical amino acids, NTPs, salts, cofactors, an energy source and optionally an energy source comprising a phosphate group (such as phosphoenol pyruvate (PEP)), a translation template, a transcription template, and any combination thereof.

Embodiment 13

The platform of any of the foregoing embodiments further comprising an energy source and optionally an energy source comprising a phosphate group (such as phosphoenol pyruvate (PEP)), wherein the energy source is present at a concentration of greater than about 30 mM, 40 mM, 50 mM, 60 mM, 70 mM, 80 mM, or 90 mM (preferably greater than about 67 mM), but less than about 100 mM, or within a concentration range bounded by of these values.

Embodiment 14

The platform of any of the foregoing embodiments further comprising a source of potassium ($K^+$), wherein the platform comprises potassium at a concentration greater than about 50 mM, 100 mM, 150 mM, 200 mM, 250 mM, 300 mM, 350 mM, 400 mM, or 450 mM (preferably about 300 mM), but less than about 500 mM, or within a concentration range bounded by of these values; and/or the platform of any of the foregoing embodiments further comprising a source of magnesium ($Mg^+$), wherein the platform comprises magnesium at a concentration greater than about 1 mM, 2 mM, 3 mM, 4 mM, 5 mM, 6 mM, 8 mM, 12 mM, 16 mM or 20 mM (preferably about 8 mM), but less than about 30 mM, or within a concentration range bounded by of these values.

Embodiment 15

The platform of any of the foregoing embodiments, wherein the platform or one or more components thereof are preserved by freeze-drying.

Embodiment 16

A method for preparing mRNA, a sequence defined biopolymer, a peptide (e.g., an amino acid sequence having 5-100 residues), or a polypeptide in vitro, the method comprising transcribing the mRNA from a transcription template and/or translating an mRNA in the platform of any of the foregoing embodiments, wherein the mRNA encodes the sequence defined biopolymer, the peptide, or the polypeptide.

Embodiment 17

The method of embodiment 16, wherein the method comprises transcribing a DNA template in the platform to provide the translated mRNA.

Embodiment 18

The method of embodiment 16 or 17, wherein the method is performed at a temperature between about 20-40° C.

Embodiment 19

The method of any of the embodiments 16-18, wherein the sequence defined biopolymer or protein is a therapeutic protein and/or the method is utilized to identify therapeutic proteins or biomaterials.

Embodiment 20

A method of detecting a target molecule in a biological or environmental sample, the method comprising detecting the target molecule in a cell-free protein synthesis system with *Vibrio*-based cell lysates.

Embodiment 21

A kit comprising as components: (a) a cellular extract prepared from a cell culture of a species of *Vibrio*; and (b) a reaction mixture for translating an mRNA, optionally wherein the species of *Vibrio* is *Vibrio natriegens*.

Embodiment 22

The kit of embodiment 21 or 22, wherein the reaction mixture comprises one or more components selected from the group consisting of amino acids which optionally may include non-canonical amino acids, NTPs, salts, cofactors, an energy source and optionally an energy source comprising a phosphate group (such as phosphoenol pyruvate (PEP)).

Embodiment 23

A recombinant species of *Vibrio*, optionally *Vibrio natriegens*, wherein the species of *Vibrio* is engineered to be deficient in a negative effector for cell-free protein synthesis (CFPS).

Embodiment 24

The recombinant species of *Vibrio* of embodiment 23, wherein the negative effector for CFPS is selected from the group consisting of the *Vibrio* homolog of *E. coli* endA, mazF, rna, rnb, rne, gor, lon, ompT, gdhA, gshA, sdaA, sdaB, speA, WaaL, tnaA, glpK, and any combination thereof.

Embodiment 25

The recombinant species of *Vibrio* of any of the foregoing embodiments, wherein the species of *Vibrio* is engineered to express an upregulated gene product that is a positive effector for CFPS.

Embodiment 26

The recombinant species of *Vibrio* embodiment 25, wherein the positive effector for CFPS is selected from the group consisting of the *Vibrio* homolog of *E. coli* ackA, ndk, pykF, cdd, dsbC, dnaK, dnaJ, crpE, tig, groS, groL, infA, infB, fusA, efp, lepA, tufB, hs1R, ffr, and any combination thereof.

Embodiment 27

The recombinant species of *Vibrio* of any of the foregoing embodiments, wherein the species of *Vibrio* is engineered to be deficient in a release factor 1.

Embodiment 28

The recombinant species of *Vibrio* of any of the foregoing embodiments, wherein the species of *Vibrio* has been genomically-recoded to replace one or more stop codons with a different codon.

Embodiment 29

The recombinant species of *Vibrio* of any of the foregoing embodiments, wherein the species of *Vibrio* has been engineered to express T7 RNA polymerase.

EXAMPLES

The following Examples are illustrative and should not be interpreted to limit the scope of the claimed subject matter.

Example 1—Establishing a High-Yielding Cell-Free Protein Synthesis Platform Derived from *Vibrio natriegens*

Reference is made to Des Soye et al., "Establishing a High-Yielding Cell-Free Protein Synthesis Platform Derived from *Vibrio natriegens*," ACS Synth. Biol. 2018 Sep. 21; 7(9):2245-2255, the content of which is incorporated herein by reference in its entirety.

Abstract

A new wave of interest in cell-free protein synthesis (CFPS) systems has shown their utility for producing proteins at high titers, establishing genetic regulatory element libraries (e.g., promoters, ribosome binding sites) in non-model organisms, optimizing biosynthetic pathways before implementation in cells, and sensing biomarkers for diagnostic applications. Unfortunately, most previous efforts have focused on a select few model systems, such as *Escherichia coli*. Broadening the spectrum of organisms used for CFPS promises to better mimic host cell processes in prototyping applications and open up new areas of research. Here, we describe the development and characterization of a facile CFPS platform based on lysates derived from the fast-growing bacterium *Vibrio natriegens*, which is an emerging host organism for biotechnology. We demonstrate robust preparation of highly active extracts using sonication, without specialized and costly equipment. After optimizing the extract preparation procedure and cell-free reaction conditions, we show synthesis of 1.6±0.05 g/L of superfolder green fluorescent protein in batch mode CFPS, making it competitive with existing *E. coli* CFPS platforms. To showcase the flexibility of the system, we demonstrate that it can be lyophilized and retain biosynthesis capability, that it is capable of producing antimicrobial peptides, and that our extract preparation procedure can be coupled with the recently described Vmax™ Express strain in a one-pot system. Finally, to further increase system productivity, we explore a knockout library in which putative negative effectors of CFPS are genetically removed from the source strain. Our *V. natriegens*-derived CFPS platform is versatile, and simple to prepare and use. We expect it will facilitate expansion of CFPS systems into new laboratories and fields for compelling applications in synthetic biology.

INTRODUCTION

Cell-free systems have recently enjoyed a technical renaissance that has transformed them into robust platforms for the synthesis of a wide variety of useful and interesting products[1-4]. Such platforms combine crude cell lysates or purified components with substrates in a test tube, enabling the activation and use of cellular processes in vitro (FIG. 1). Cell-free protein synthesis (CFPS) systems in particular have made significant advances in reaction volume, duration, and productivity, now reaching g/L quantities of protein[3,5-12]. These systems provide several unique advantages for understanding, harnessing, and expanding the capabilities of natural biological systems. Reactions are open, and are therefore easily accessible for sample extraction and substrate feeding. Dilute reaction environments facilitate the folding of complex eukaryotic protein products which may otherwise express poorly in bacterial systems[4]. Importantly, the removal of genomic material from the chassis organism directs reaction substrates and machinery towards the desired synthesis reaction at high rates. Exploiting these features, CFPS platforms enjoy increasingly widespread use as a complement to in vivo expression for applications including biomolecular breadboarding[13-16], expression of toxic products[17-20], production of complex protein products that are poorly soluble in vivo[7,21-23], manufacture of glycoproteins[24-27], detection of disease[28-30], on demand biomanufacturing[21,31-35], and education[36,37].

Despite the emergence of cell-free systems as a prominent research tool for fundamental and applied biology, the vast majority of previous efforts have focused on a select few model systems such as *Escherichia coli*, *Saccharomyces cerevisiae*, and Chinese Hamster Ovary cells, among others[2,5,11,12,38,39]. However, we and others hypothesize that developing cell-free systems composed of extracts derived from relevant chassis organisms that better mimic the natural physicochemical environment might enhance predictive power for synthetic biology applications. This idea motivates the development of new cell-free systems. In this context, several new CFPS systems have been developed, including some from *Streptomyces* species and *Bacillus*[40-44]. For example, an elegant study by Freemont and colleagues characterized new DNA parts from the non-model bacterium *Bacillus megaterium* by combining automated CFPS and Bayesian models[44].

A particularly exciting chassis organism for developing a new cell-free system is the fast-growing halophilic marine bacterium *Vibrio natriegens*. First discovered in a Georgia salt marsh in 1958, *V. natriegens* (originally classified as *Pseudomonas natriegens*) was identified as the fastest-growing bacterium known to date when it was discovered that cell populations in liquid culture double approximately once every 10 minutes[45,46]. Despite this noteworthy trait, *V. natriegens* went largely unstudied for decades. Recently, interest in this organism has been renewed, largely out of a desire to leverage its rapid generational time to accelerate molecular biology efforts and improve recombinant protein production[47,48].

*V. natriegens*' rapid doubling time is particularly interesting for potential CFPS system development, as in the context of CFPS it is generally accepted that lysate productivity loosely correlates to chassis organism growth rate[49,50]. After all, proper cell division relies on the coordinated activities of a large suite of proteins, so it is reasonable to infer that rapidly dividing cells require high protein synthesis rates, and by extension possess highly active protein translation machinery. This is very likely the case for *V. natriegens*—the species features 12 rRNA operons as compared to the 7 found in *E. coli* strain MG1655[47]. Furthermore, it has been suggested that exponentially-growing *V. natriegens* cells contain ~115,000 ribosomes/cell, significantly higher than the ~70,000 ribosomes/cell observed in *E. coli*[51]. Considering these advantages, we hypothesized that lysates derived from *V. natriegens* would be enriched in active protein translation machinery and thus compose a highly productive CFPS platform.

In this study, we describe the development of a facile CFPS platform derived from *V. natriegens*. Key design criteria were to make the system robust, easy to use, and accessible to all. Therefore, since cell lysis procedures using homogenization or French press can be expensive, time and labor intensive, and hard to standardize, we focused on developing an extract preparation procedure using standard sonication equipment[52]. Previously, we have shown that sonication offers a simple strategy to reduce cost and variability in crude *E. coli* extract preparation, while eliminating the need for specialized and expensive growth and lysis equipment[52]. We first showed the ability to create a protein synthesis competent cell-free system. We then optimized the extract preparation process by modifying growth media, cultivation time, cell disruption conditions, and lysate clarification conditions. This led to a 400% increase from the non-optimized case, resulting in a cell-free system capable of synthesizing ~1 mg/mL of superfolder green fluorescent protein (sfGFP) using a typical *E. coli* CFPS reagent mix. Further optimization of key reagent concentrations increased the productivity of the system to ~1.6 mg/mL. We lyophilized fully-assembled *V. natriegens* CFPS reactions and found that, if prepared in the presence of trehalose, reactions retain 100% productivity after one week of storage at room temperature. Next, we applied homologous recombination-based genome engineering to prepare a small library of knockout strains in which the genes encoding putative negative effectors of CFPS have been removed. Lysates were prepared from each of these knockout strains in an attempt to identify a strain background with improved productivity in vitro. The *V. natriegens* CFPS system described here is productive, robust, and facile to prepare. We expect it will lower the barrier for entry into the use of CFPS systems.

Results and Discussion

Identifying Extract Preparation Conditions for *V. natriegens* CFPS.

We began our study by trying to develop extract preparation procedures. Because CFPS exploits an ensemble of catalytic proteins prepared from the crude lysate of cells, the cell extract (whose composition is sensitive to growth media, lysis method, and processing conditions) is the most critical component of extract-based CFPS reactions. In recent years, systematic optimization of each step in extract preparation for *E. coli* CFPS has improved extract robustness and productivity[1,52]. Similar advances have been made in *S. cerevisiae*, *Streptomyces*, and *Pseudomonas* CFPS systems[38,41,53]. Based on these successes, we chose to vary extract preparation conditions in search of parameters that might improve reproducibility between extract preps, increase the level of protein synthesized, and allow for potential downstream scalability. A key focus was to generate a large volumetric yield of lysate even when chassis cells are cultured at volumes that can be accommodated by shake flasks.

Figure 7:
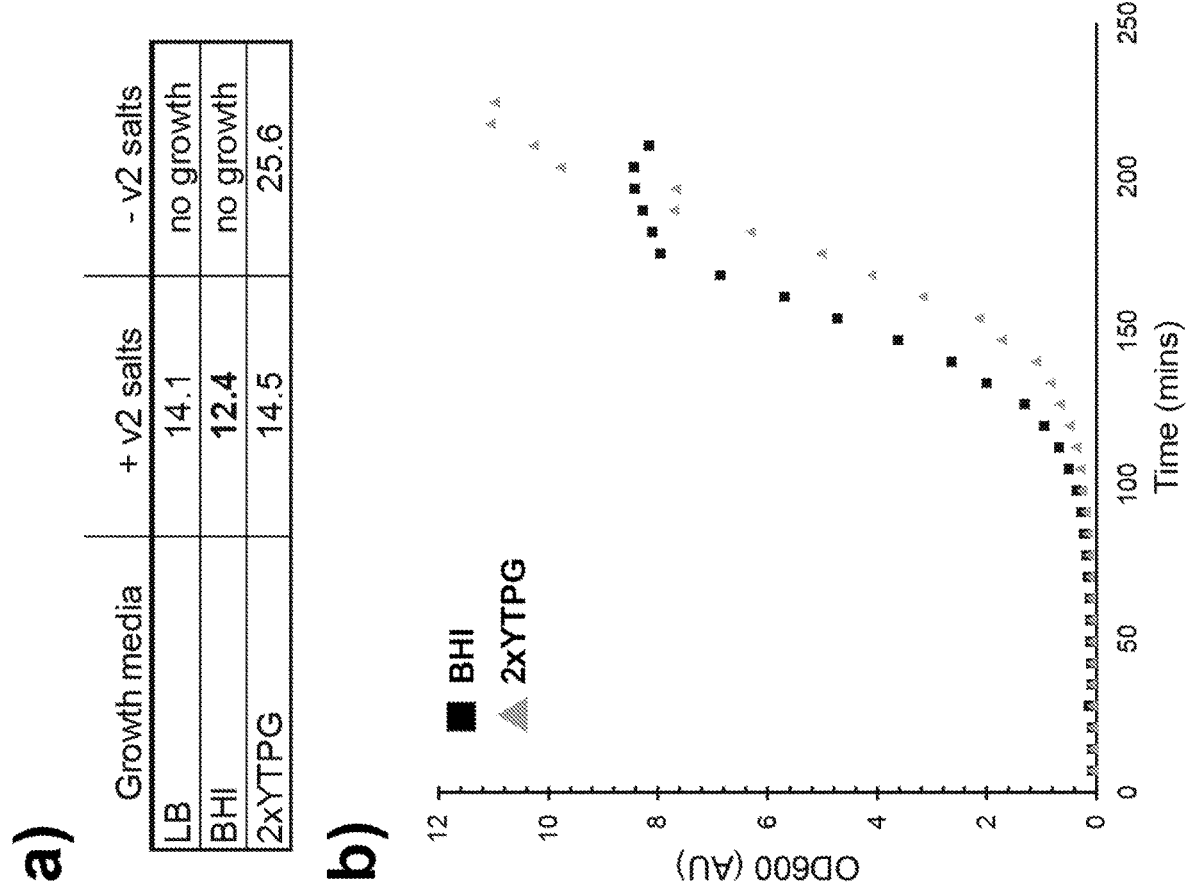
FIG. 7. Characterization of *V. natriegens* growth rate. (a) Doubling time, in minutes, of *V. natriegens* grown in the specified media and salt conditions at 37° C. v2 salts=204 mM NaCl, 4.2 mM KCl, 23.14 mM $MgCl_2$. (b) Timecourse of *V. natriegens* growth in liquid culture at 1 L scale using the listed growth media. Cells were grown in a 2.5 L Tunair® shake flask and incubated at 37° C. at 250 RPM.

Generally, the extract preparation process includes the following major steps: cell cultivation, cell disruption, lysate clarification, and some optional steps like run-off reaction and dialysis. We decided to explore each of these steps. First, we wanted to confirm the previously reported doubling times for *V. natriegens* (Vnat). To accomplish this, we prepared liquid cultures of wild type Vnat cells in several different liquid growth media. Each growth medium was tested with and without v2 salt supplementation[47], and culture growth was monitored via plate reader over a 20 hour incubation (FIG. 7A). Under the conditions tested, Vnat was found to double approximately every 12-14 minutes in salt-supplemented growth medium. This range aligns with previously reported data and outpaces standard *E. coli* laboratory strains[47,48]. Unsurprisingly, in most of the media investigated, the growth of Vnat is severely inhibited in the absence of salt. This held true at culturing volumes of 1 L incubated in shake flasks, which are typical volumes and conditions used to culture cells for lysate preparation (FIG. 7B).

Figure 2:
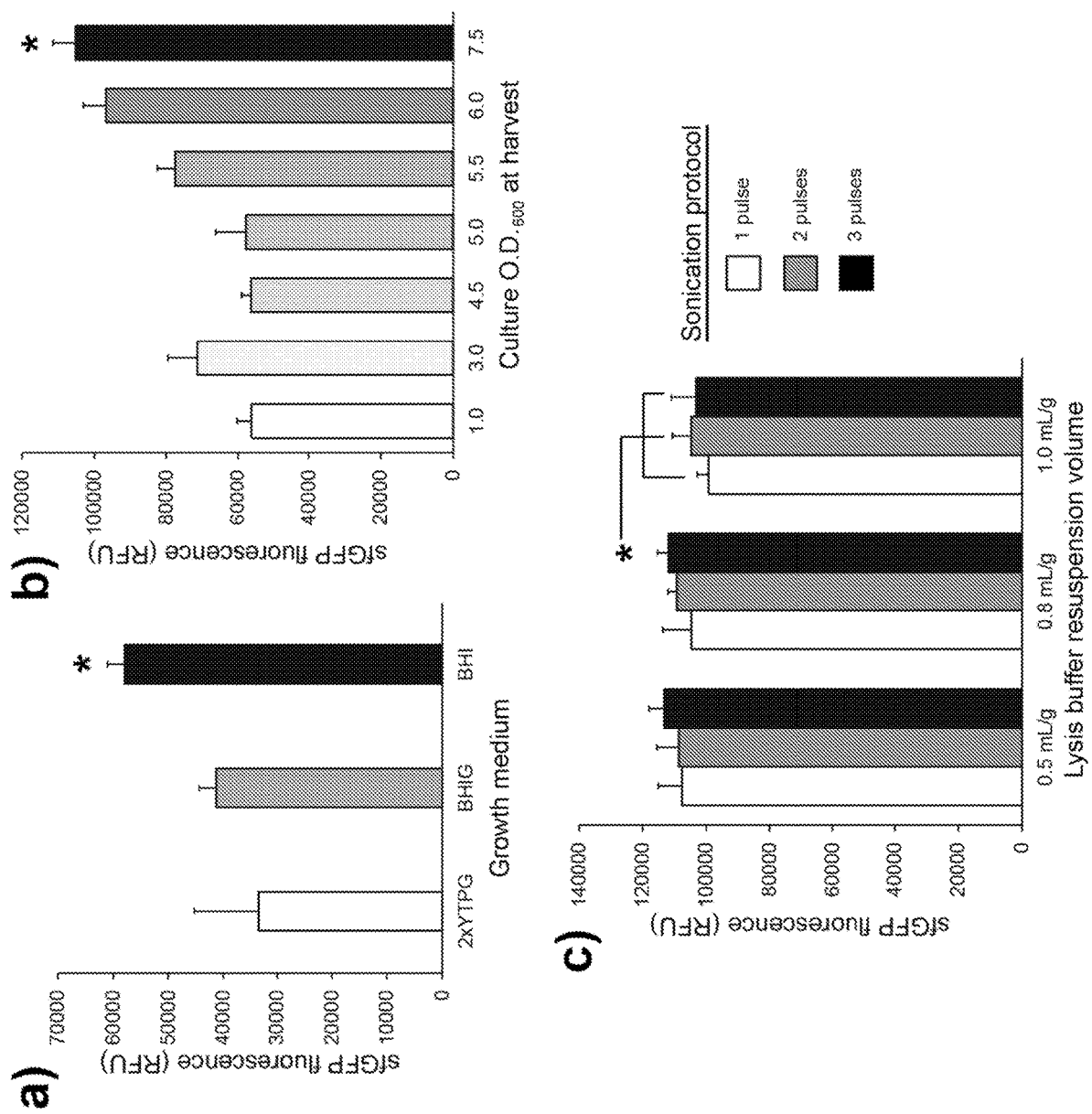
FIG. 2. Optimization of *V. natriegens* harvest and lysis procedures. (a) sfGFP fluorescence in vitro from cell extracts derived from *V. natriegens* cultured in the specified liquid medium supplemented with v2 salts (204 mM NaCl, 4.2 mM KCl, 23.14 mM $MgCl_2$). Cells were harvested at $OD_{600}$=4.5 (b) sfGFP fluorescence from cell extracts derived from *V. natriegens* harvested at the specified $OD_{600}$. Cell culture was performed using BHI medium plus v2 salts. For both (a) and (b), established *E. coli* protocols were used for lysate preparation. (c) Lysis optimization. *V. natriegens* cell pellets were suspended in the specified volume of S30 lysis buffer and subjected to the indicated number of sonication pulses to achieve lysis. sfGFP fluorescence in vitro from the resulting lysates is shown. All CFPS reactions used an existing *E. coli* reagent mix. For all conditions, three independent reactions were performed and one standard deviation is shown. *=statistically significant for $p<0.05$. Bullet points: BHI medium is best for culturing cells for CFPS lysate preparation; the most productive *V. natriegens* lysates are derived from stationary phase cultures; and *V. natriegens* cells are agnostic to lysis conditions.

We next set out to establish the growth medium that is optimal for culturing cells for Vnat CFPS lysate preparation. 1 L cultures of Vnat were grown in 2×YTPG (16 g/L tryptone, 10 g/L yeast extract, 5 g/L NaCl, 7 g/L $K_2HPO_4$, 3 g/L $KH_2PO_4$, 18 g/L glucose), BHI (brain-heart infusion), and a BHI variant supplemented with 1.8% (m/v) glucose (BHIG), in all cases supplemented with v2 salts. Cell pellets were collected at $OD_{600}$=4.5 to mimic the best practice of harvesting *E. coli* cultures during mid-exponential phase, and protocols previously established for *E. coli* were used for lysate preparation and CFPS synthesis of sfGFP. Specifically, we assembled CFPS reactions with the sfGFP template and carried out 15 μL batch reactions for 20 h at 30° C. Lysates derived from cells cultured in BHI were significantly more productive than those from cells grown in either of the other two media types (FIG. 2A). Based on these cumulative results, we selected BHI for use in Vnat cultures going forward.

Figure 8:
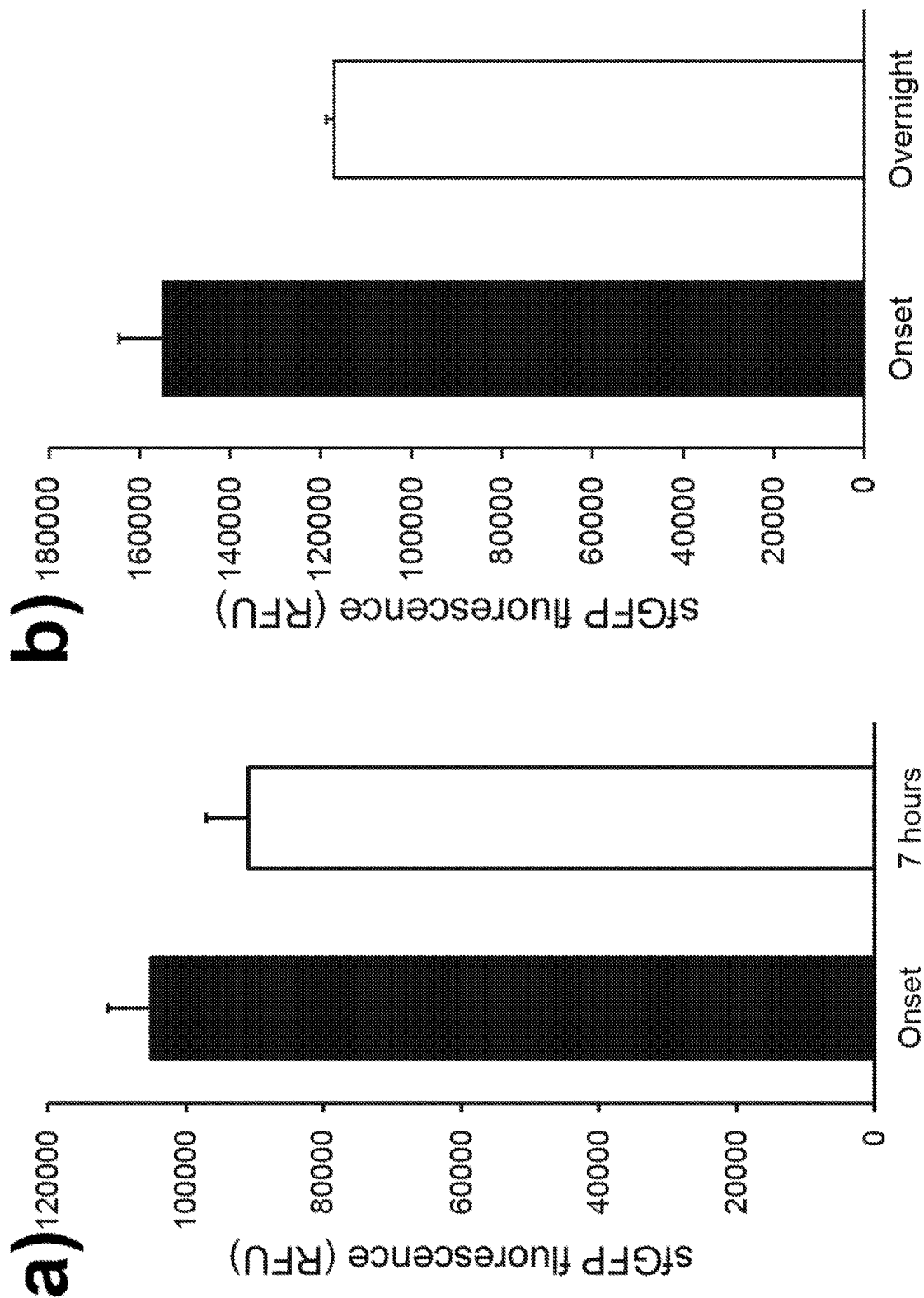
FIG. 8. CFPS yields from *V. natriegens* cells harvested at late stages of growth. (a) sfGFP fluorescence values from a lysate that was prepared from *V. natriegens* cells that remained in stationary phase for 7 hours, compared to a lysate prepared from cells gathered right at the onset of stationary phase. (b) sfGFP fluorescence values from a lysate that was prepared from *V. natriegens* cells that were inoculated near the end of the day and allowed to grow at 37° C. overnight (total culture time=16 hours). The result is compared to a lysate prepared from cells gathered right at the onset of stationary phase. For each condition 3 independent reactions were performed, and one standard deviation is shown.

Next, we investigated the ideal time point at which to collect Vnat cell pellets for CFPS lysate production. As previously mentioned, in *E. coli*-based systems, the most productive lysates are derived from cells gathered during mid-exponential phase growth[3,52,54]. It is generally accepted that this is because the pool of active ribosomes is most enriched during this phase of the growth cycle. We therefore hypothesized that the most productive Vnat lysates would similarly be derived from cells harvested in mid-exponential phase. To test this, we harvested Vnat cultures at a range of optical densities ranging from lag phase, through exponential phase, and even into stationary phase. Lysates were prepared from each cell pellet and directed to synthesize sfGFP in CFPS (FIG. 2B). We were surprised to observe that Vnat lysate productivity increases with increasing $OD_{600}$ past the exponential phase of growth—indeed, the most productive lysate identified was prepared from cells in early stationary phase. Lysates retain ~85% productivity when prepared from cultures at stationary phase for several hours (FIG. 8A) and ~75% productivity when prepared from overnight cultures (FIG. 8B). These surprising results run counter to what is typically observed with other CFPS chassis organisms. In *E. coli*, for instance, it is believed that stationary phase cells experience a reduction in active ribosomes in response to the reduced demand for protein synthesis; this effect propagates to lysates, resulting in a severe reduction in CFPS productivity[55]. Going forward, Vnat cultures were harvested for lysate preparation immediately upon entry into stationary phase ($OD_{600}$~7.5).

Identification of Optimal Procedures for Preparation of *V. natriegens* Lysates.

Having established Vnat-specific cell culture and harvest parameters, we proceeded to identify conditions for preparing Vnat lysates via sonication that maximized CFPS yields. We focused our investigation on two key factors pertaining to lysate preparation. The first of these, cell pellet resuspension volume, describes the volume of lysis buffer used to resuspend a cell pellet prior to lysis. Modulating this volume has a direct influence on the concentration of cellular components in the final lysate, which in turn affects lysate productivity. The second factor considered was energy delivery to the cells during sonication. During lysis, enough energy must be delivered to ensure adequate rupturing of cellular compartments but must then be constrained to prevent denaturation of ribosomes, enzymes, and other fragile cellular components required for robust protein synthesis. Both of these parameters were simultaneously varied for lysis optimization, as we have done before when developing a similar protocol for *E. coli*[52]. Vnat cell pellets were resuspended in 0.5, 0.8, or 1.0 mL of S30 buffer per gram of wet cell mass. Each suspension was then sonicated, with lysis achieved using one, two, or three 45-second pulses. Each resulting lysate was directed in CFPS to synthesize sfGFP (FIG. 2C).

Collectively, the results reveal that Vnat cells are relatively agnostic to both resuspension volume and lysis energy. Productivities of all nine lysates tested were within 10% of one another. The more concentrated suspensions demonstrate a modest (but statistically significant) increase in productivity relative to the samples prepared from cells resupended in 1.0 mL buffer/g cells, likely a consequence of slightly more concentrated translation components. There is no appreciable difference between samples suspended in 0.5 mL buffer/g cells vs. 0.8 mL buffer/g cells. Due to the relative difficulty of resuspending cells in 0.5 mL buffer/g as well as the accompanying reduction in the volume of lysate yielded under that condition, we selected 0.8 mL buffer/g cells as our resuspension density going forward. Due to the insignificant differences in productivity when two or three sonication pulses are used for lysis, we settled on the use of three pulses to remain consistent with several recently-reported *E. coli* lysis protocols[3,54].

Figure 9:
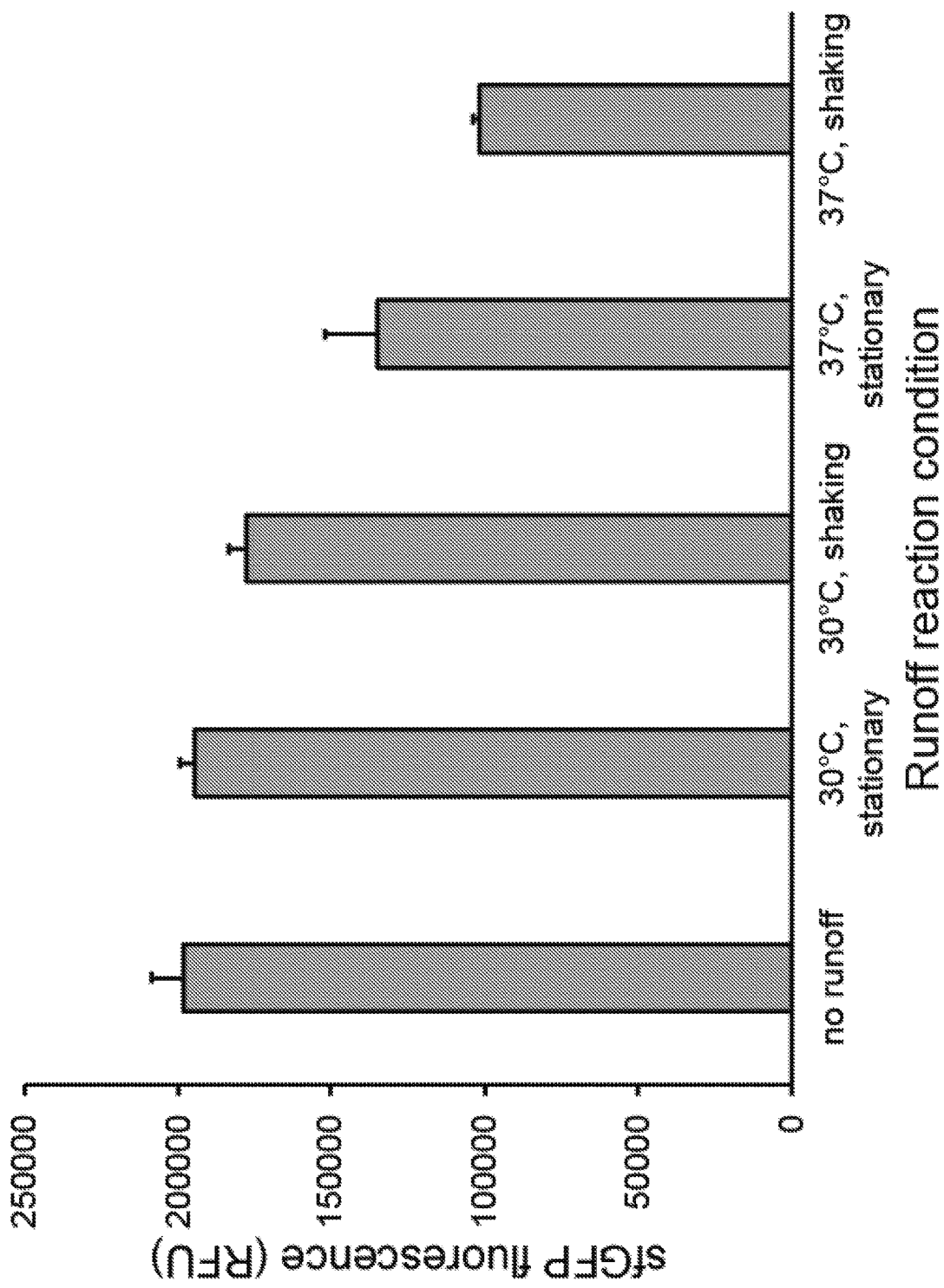
FIG. 9. Characterization of *V. natriegens* run-off reaction. sfGFP fluorescence from lysates prepared using run-off reactions performed under the specified conditions is shown. Run-off reactions, if performed, ran for 1 hr. Shaking=agitated at 250 RPM. For each condition 3 independent reactions were performed, and one standard deviation is shown.

After we defined a reproducible cell lysis strategy to generate highly active extracts, we decided to investigate a post-lysis extract preparation step. Specifically, we evaluated the effect of the run-off reaction. Lysates derived from some strains of *E. coli* benefit tremendously from a run-off reaction, whereby clarified lysate is shaken in an incubator followed by a second clarifying spin to yield the final extract[3,52,54]. It is believed that this incubation allows ribosomes to complete translation of native mRNAs that they were bound to at the moment of lysis and subsequent degradation of those mRNAs by native RNAses. In this way, ribosomes are made available for synthesis of a target CFPS product[56,57]. To see if Vnat lysate productivity could be improved in this way, we prepared a panel of lysates subjected to run-off reactions at either 30° C. or 37° C., both with and without shaking at 250 RPM (FIG. 9). This analysis revealed no benefit to performing any sort of run-off reaction. Indeed, overall productivity suffers when Vnat lysates are subjected to prolonged agitation or elevated temperatures. Since pre-incubation is not necessary, we chose to not include the run-off reaction step in our Vnat cell extract preparation procedure.

Optimization of Reagent Concentrations and Reaction Conditions in *Vibrio* CFPS.

With extraction preparation procedures in hand, we turned our attention to optimizing several reaction conditions which are known to impact CFPS yields. These optimizations were essential, since all reactions performed up until this point had been done using reagent and substrate conditions previously developed for *E. coli* CFPS. Because Vnat in nature are found in a different environment than *E. coli*, we reasoned that Vnat lysates may have different demands for small molecules and other reagents. Previous studies have demonstrated that CFPS performance can be improved by supplying reagents at concentrations similar to what is encountered by the chassis organism in natures ss Thus, we hypothesized that yields of the system could be increased by modifying the existing *E. coli* reagent mix to have a more Vnat-specific composition. To test this, we varied the concentrations of several key components and observed how each change affected the yields of the system in CFPS.

Figure 3:
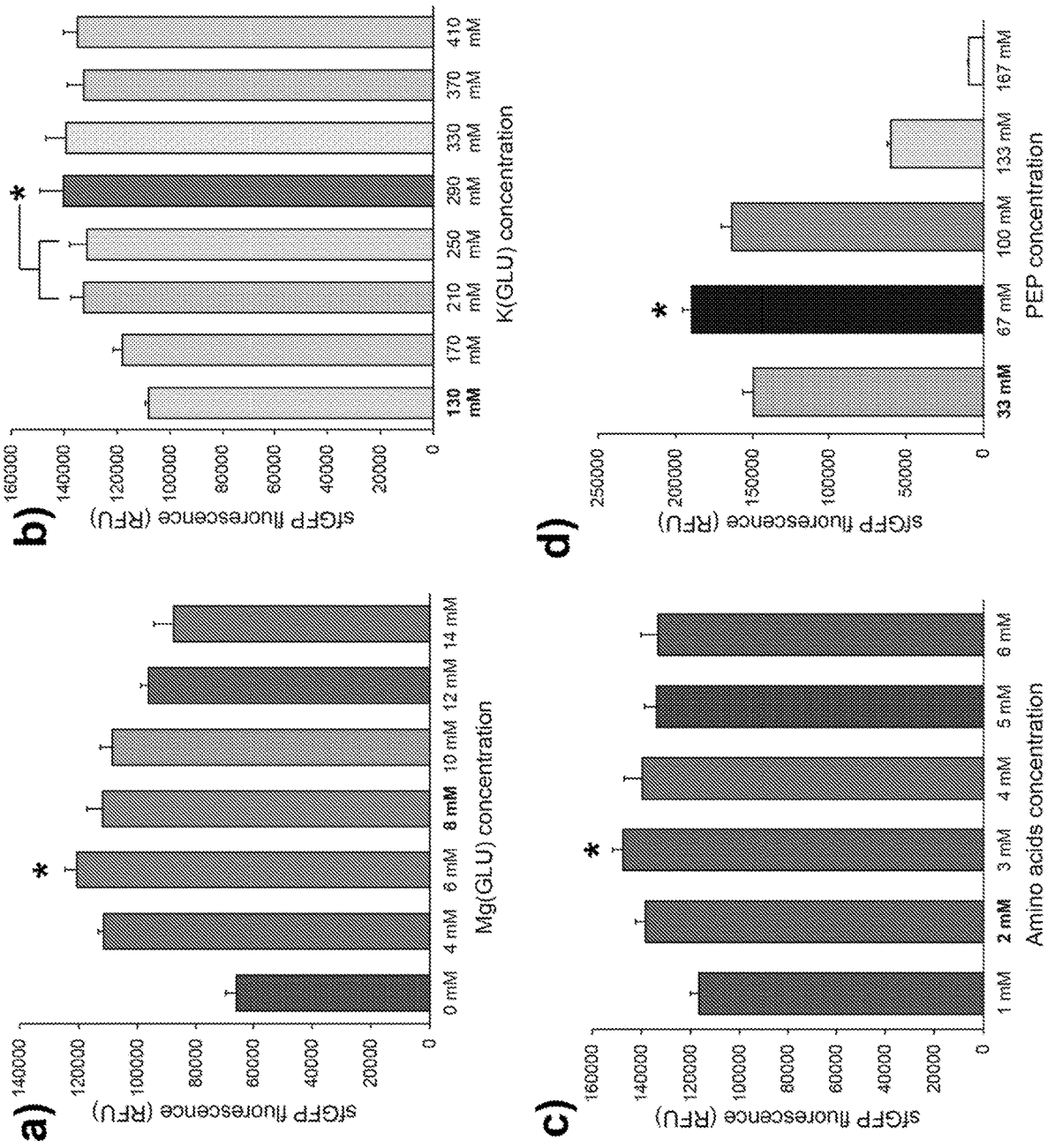
FIG. 3. Optimization of CFPS reagent mix. A single *V. natriegens* lysate was prepared using optimized parameters identified in FIGS. 1-2. Shown are sfGFP fluorescence values obtained using the lysates in vitro when the specified concentration of each of the following reagents is used: (a) Mg(GLU), (b) K(GLU), (c) amino acids, (d) PEP. For all conditions, three independent reactions were performed and one standard deviation is shown. *=statistically significant for $p<0.05$. Bullet points: *V. natriegens* lysates perform best using a slightly different reagent mix than *E. coli* lysates; 6 mM Mg(GLU), 290 mM K(GLU), 3 mM AAs and 67 mM PEP are optimal for this system.
Figure 10:
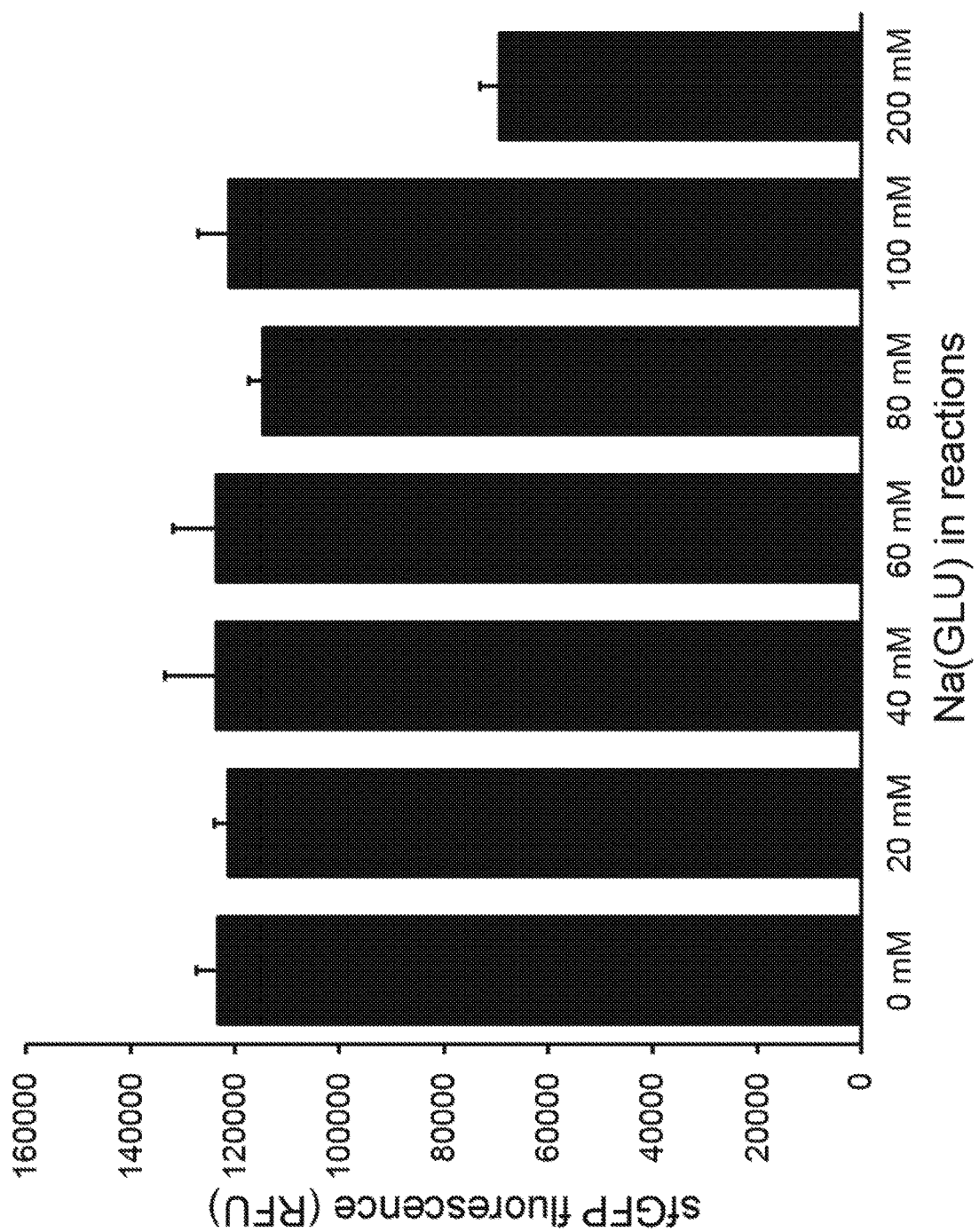
FIG. 10. *V. natriegens* Na(GLU) optimization. sfGFP fluorescence is shown from CFPS reactions supplemented with the indicated concentrations of Na(GLU). For each condition, 3 independent reactions were performed, and one standard deviation is shown.

One notable difference between *E. coli* and Vnat is that the latter is halophilic[45-48]. Indeed, exponential phase Vnat requires significant amounts of cations including $Mg^{2+}$, $K^+$, and $Na^+$[59]. In CFPS, $Mg^{2+}$ is a particularly important reagent as it is a critical cation required for proper ribosome assembly[60]. Thus, we reasoned that the salt content of the extant reagent mix could be improved for use with Vnat lysates. Our approach to address this was twofold. First, we varied the concentration of magnesium glutamate [Mg (GLU)] in the reaction mix (FIG. 3A). The system performed best when supplemented with 6 mM Mg(GLU). We also varied the concentration of potassium glutamate [K(GLU)] in the reaction mix (FIG. 3B). System productivity increased steadily with increasing K(GLU) concentration, up to a maximum beginning at 290 mM K(GLU). This is more than double the 130 mM K(GLU) used in the *E. coli* mix, and is in agreement with a previous study documenting the higher demand for $K^+$ in Vnat growth[59]. We also tested various concentrations of sodium glutamate, but observed no significant improvements to the system (FIG. 10).

Next, we looked at optimizing the concentration of amino acids in the reaction mix. As the monomeric building blocks of proteins, amino acids are a key CFPS reagent. Besides their central involvement in protein synthesis, some amino acids are also active participants in central metabolic pathways—consequently, CFPS productivity can be impaired by any non-productive consumption of amino acids by metabolic pathways still active in the lysate[3,61]. We therefore reasoned that due to potential differences in central metabolism, Vnat lysates may have different amino acid demands than *E. coli* systems. To test this, we varied the concentrations of all 20 amino acids added to the CFPS reagent mix (FIG. 3C). Increasing the concentration of each amino acid from 2 mM to 3 mM yielded a modest, but significant increase in the productivity of the Vnat CFPS system.

The final reagent examined was phosphoenol pyruvate (PEP). A secondary metabolite used in the latter half of glycolysis, PEP is the primary source of ATP in the PANOx-SP energy regeneration system[5]. Similar to amino acids, ATP is utilized by a plethora of cellular processes, and in cell-free systems is consumed to an extent by non-productive side pathways. Thus, as with amino acids, we reasoned that Vnat lysates may have different PEP requirements than *E. coli* lysates. To test this, we varied the concentration of PEP added to Vnat CFPS reactions (FIG. 3D). We found that doubling the PEP concentration from 33 mM (the optimal concentration previously reported for *E. coli*-based CFPS) to 66 mM yielded a 34% increase in the productivity of the system.

Figure 11:
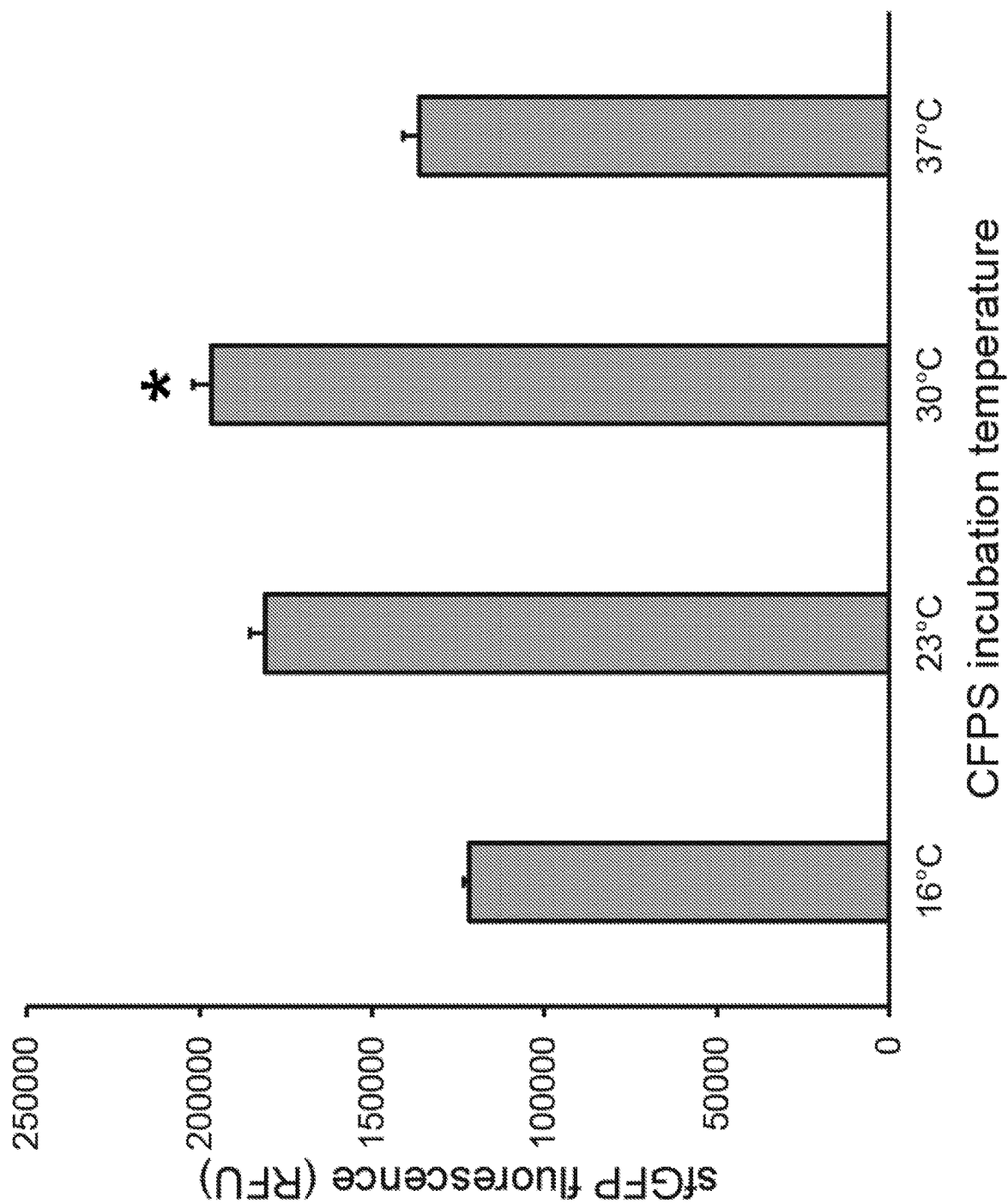
FIG. 11. Characterization of *V. natriegens* CFPS reaction incubation temperature. Shown are sfGFP fluorescence values for CFPS reactions left to incubate for 20 hrs at the indicated temperature. For each condition, 3 independent reactions were performed, and one standard deviation is shown. *=statistically significant for $p<0.05$.

Cell-free reaction temperature is another key factor that can be optimized, because it affects enzyme activities and protein folding. We therefore next sought to establish the optimal reaction incubation temperature for Vnat CFPS. All prior reactions up to this point had been incubated at 30° C. as per *E. coli* protocols[3,54]. However, as *V. natriegens* evolved in an environment with an ambient temperature of only ~23° C., we reasoned that its cellular components may operate more efficiently at lower temperatures. To test this, we incubated Vnat CFPS reactions at several temperatures ranging from 16-37° C. (FIG. 11). We observed that Vnat CFPS reactions are most productive at 30° C., which could also represent the optimum for our reporter protein sfGFP to fold into an active confirmation. Still, the system only experiences a 10% reduction in productivity when incubated at room temperature (~23° C.), and retains >60% productivity at 16° C.

Figure 4:
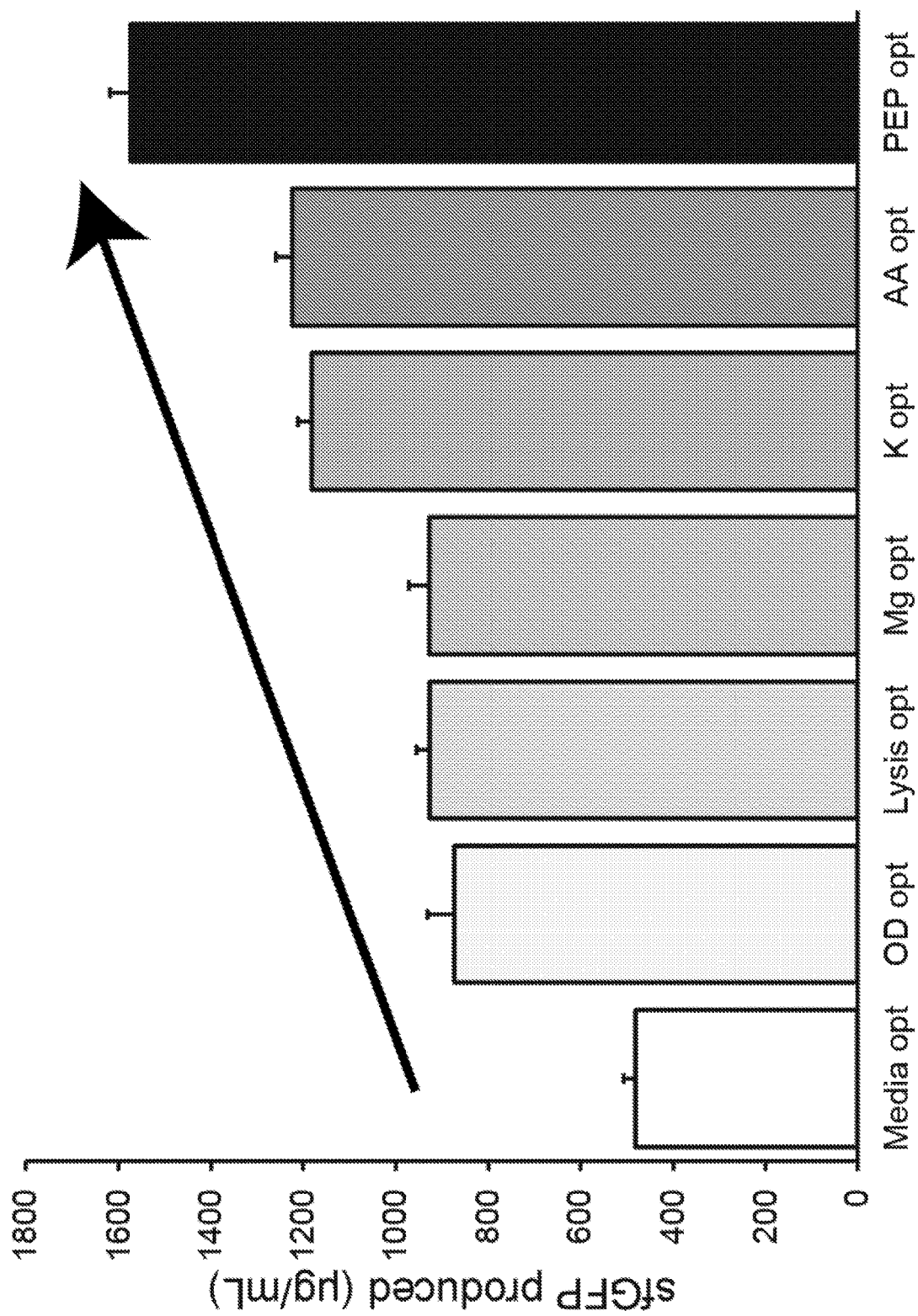
FIG. 4. Summary of the development and optimization of *V. natriegens* CFPS. sfGFP yields from each of the best conditions identified in the indicated optimizations are shown. For each condition, three independent reactions were performed and one standard deviation is shown. Media opt=identification of preferred liquid culture medium; OD opt=identification of optimal $OD_{600}$ at harvest; Lysis opt=identification of optimal sonication procedure; Mg opt=optimization of Mg(GLU) in CFPS reaction mix; K opt=optimization of K(GLU) in CFPS reaction mix; AA opt=optimization of amino acids in CFPS reaction mix; PEP opt=optimization of PEP in CFPS reaction mix. Bullet point: Yields of the fully optimized system are comparable to popular systems based on *E. coli* lysates.

The final, optimized Vnat CFPS platform described here is capable of synthesizing ~1.6 mg/mL of sfGFP in 20-hour batch mode reactions. FIG. 4 captures the step wise yield increases achieved per process optimization. Overall, the yield is comparable to state-of-the-art systems derived from *E. coli*, which have been improved over the last two decades[1,3,6], and to our knowledge is the highest-yielding CFPS system derived from this relatively understudied non-model organism.

Assessing the Capabilities of *V. natriegens* CFPS.

Figure 5:
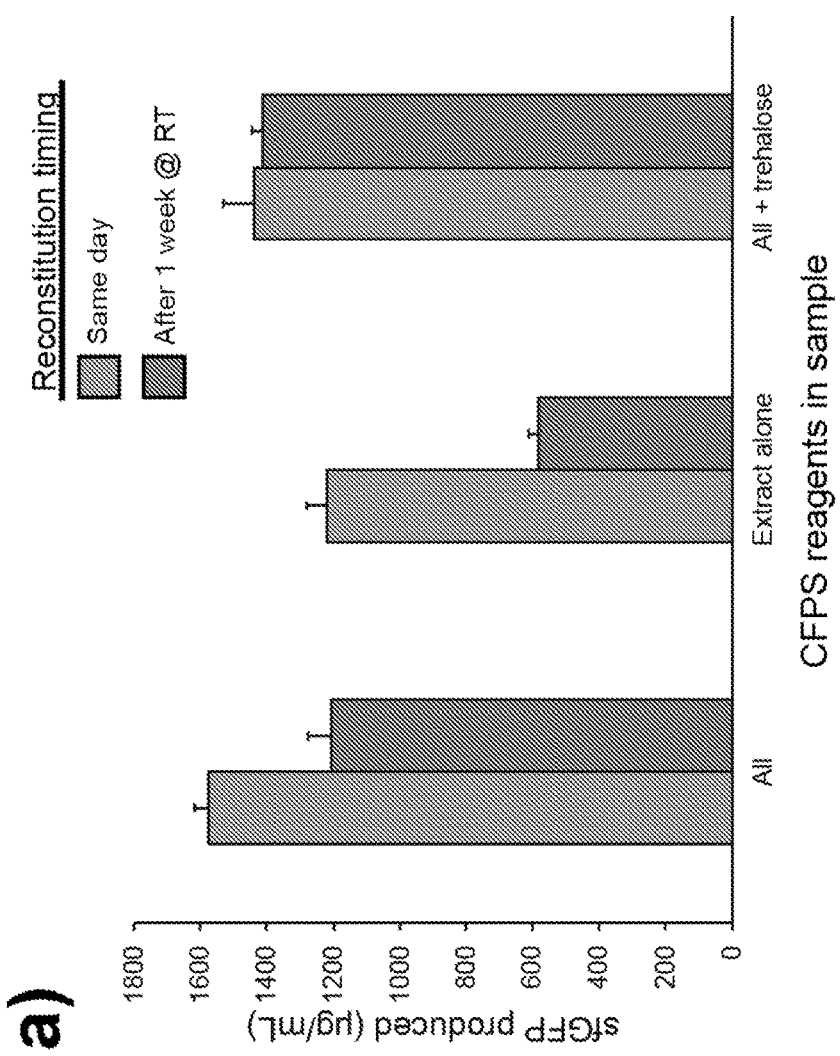
FIG. 5. Demonstration of the capabilities of *V. natriegens* CFPS. (a) Luminescence generated from active firefly luciferase synthesized using *V. natriegens* CFPS. 12 independent reactions were performed, and one standard deviation is shown. (b) Autoradiograph depicting full-length, soluble CRM197 and ScFv synthesized in *V. natriegens* CFPS. (c) Yields of sfGFP from lyophilized *V. natriegens* CFPS reactions. Reactions were assembled both without (All) and with supplementation with 2.5% trehalose (All+ trehalose) or 5% glycerol (All+glycerol). These reactions, along with samples of just *V. natriegens* lysate (Extract alone) were lyophilized overnight. Lyophilized samples were reconstituted either immediately (Same day) or after incubation at room temperature (~23° C.) for 1 week. For each condition 3 independent reactions were performed, and one standard deviation is shown. Bullet points: *V. natriegens* CFPS can synthesize full-length eukaryotic proteins; n the case of luciferase, the product is enzymatically active; and *V. natriegens* CFPS reactions lyophilized in the presence of trehalose lose no efficacy even after a week of incubation at room temperature.

After a systematic optimization of the *V. natriegens*-based CFPS system, we wanted to assess its capabilities. The ability to lyophilize CFPS reactions for storage at room temperature greatly expands the potential user base for a CFPS platform by removing the requirement of storing the materials in freezers at cold temperatures[33-35]. In *E. coli*-based systems, this flexibility often comes at the expense of productivity, as even in the presence of cryoprotectants the productivity of lyophilized samples generally decreases[33,62]. To assess the ability of our Vnat CFPS platform to support robust protein synthesis even after lyophilization, we freeze-dried fully assembled reactions both with and without cryoprotectant supplementation (FIG. 5A). Samples reconstituted with water immediately following lyophilization performed quite well, experiencing only a small loss of activity likely as a result of the lyophilization process. Addition of 5% trehalose to reactions fully preserves reaction efficacy after a week of room temperature storage, with samples experiencing no detectable loss in productivity after this time. These data suggest freeze-dried strategies developed in other CFPS systems could be applied to our *V. natriegens*-based CFPS system.

To further demonstrate the ease-of-use of our system and to demonstrate possible applications, we tested CFPS reactions using lysates derived from a strain of Vnat recently developed and commercialized by Synthetic Genomics, Inc. that includes a genomic insert encoding the T7 RNA polymerase under the control of an IPTG-inducible promoter (Vmax™ Express)[47]. Such a chassis strain circumvents the need to supply this polymerase to CFPS reactions in purified form, partially addressing limitations imposed on reaction volume scale-up related to high costs of reaction substrates[61]. To test the ability of this strain to compose a one-pot CFPS platform, we prepared lysates from cells in which polymerase expression was induced and performed synthesis reactions both with and without supplementation with purified polymerase (FIG. 5B). This analysis revealed that, while overall productivity of the engineered strain is reduced relative to the wild type strain (~21% reduction), the lysates were enriched with enough T7 polymerase to catalyze more than 1 mg/mL of sfGFP synthesis.

Figure 12:
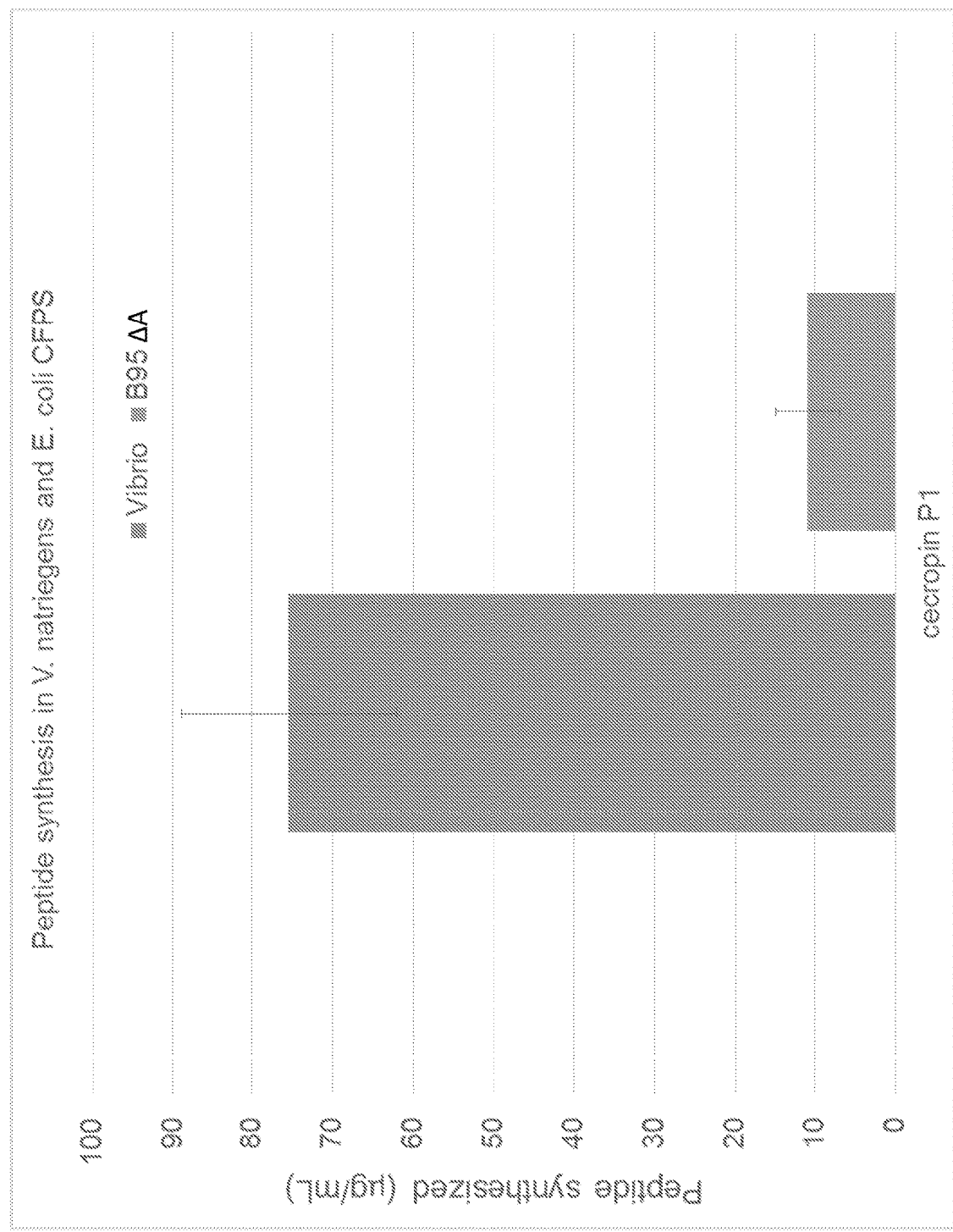
FIG. 12. Comparison of cell-free protein synthesis of Cecropin P1 peptide utilizing an extract from *V. natriegens* versus an extract from *E. coli* strain B95ΔA (see Mukai et al., "Highly reproductive *Escherichia coli* cells with no specific assignment to the UAG codon," Sci. Rep. 2015 May 18; 5:9699, the content of which is incorporated herein by reference in its entirety).

Next, we aimed to expand the targets of our CFPS reactions beyond our reporter protein (sfGFP). Short peptides (<10 kDa) have emerged as important agents in biological engineering and synthetic biology. These small biomolecules are widely used as protein mimics for interrogating protein-protein interactions and assessing enzyme substrate preferences[24,63-65], and bacteria-killing antimicrobial peptides (AMPs) are increasingly being considered for use as next-generation antibiotics as we rapidly approach a post-antibiotic era[31,66,67]. The use and study of peptides has historically been limited by our ability to synthesize usable amounts of these molecules—solid phase peptide synthesis is generally applicable only to peptides shorter than 30 amino acids[68], and recombinant expression in bacterial hosts is opposed by the degradation of peptide products by host proteases[31,67]. We reasoned that protease activity in Vnat may be reduced since unwanted proteins could simply be diluted out by rapid cell divisions, which in turn may make this organism well suited for peptide synthesis. We thus set out to see if our Vnat CFPS platform could catalyze robust expression of peptides. To test this, Vnat CFPS was applied towards the synthesis of the AMPs cecropin A[69] (SEQ ID NO:1 and 2), cecropin P1[31] (SEQ ID NO:3 and 4), and opistoporin I[31] (SEQ ID NO:5 and 6) (Table 1). Opistoporin I expression in particular surpassed 250 μg/mL, suggesting that our Vnat CFPS platform might have utility for the recombinant expression of peptides. Indeed, we show that the *vibrio* system is better at manufacturing peptides than an *E. coli* based cell-free protein synthesis systems (FIG. 12).

Optimization of the CFPS components specifically for use with *V. natriegens* lysates significantly increased the overall productivity of the system to ~1.6 mg/mL sfGFP, comparable to popular platforms based on lysates derived from *E. coli* and the highest-yielding CFPS system derived from a non-model organism, to our knowledge. This is also higher than a recent study published during the preparation of this manuscript which demonstrated expression titers of 0.4 mg/mL of green fluorescent protein in a *V. natriegens* CFPS system[71]. Further, our system is stable at room temperature if lyophilized in the presence of trehalose, is capable of synthesizing small peptide products, and can be carried out in a one-pot system with the use of the Vmax™ Express chassis strain.

Looking forward, we anticipate that the CFPS system described here will find use in the identification and characterization of *V. natriegens* genetic parts. Recent publications have developed a suite of tools for using *V. natriegens*

TABLE 1

Antimicrobial peptides used in this study.

| Name | DNA Sequence and Peptide Sequence | Source |
|---|---|---|
| Cecropin A | (SEQ ID NO: 1)<br>atgAAGTGGA AATTGTTTAA AAAGATCGAA AAGGTGGGGC<br>AAAATATCCG CGACGGGATC ATTAAGGCAG GTCCGGCTGT<br>GGCGGTCGTT GGTCAGGCAA CGCAAATCGC AAAATAA<br><br>(SEQ ID NO: 2)<br>MKWKLFKKIE KVGQNIRDGI IKAGPAVAVV GQATQIAK | 73 |
| Cecropin P1 | (SEQ ID NO: 3)<br>atgAGCTGGC TGAGCAAAAC CGCGAAAAAA CTGGAAAACA<br>GCGCGAAAAA ACGCATTAGC GAAGGCATTG CGATTGCGAT<br>TCAGGGCGGC CCGCGCTAA<br><br>(SEQ ID NO: 4)<br>MSWLSKTAKK LENSAKKRIS EGIAIAIQGG PR | 74 |
| Opistoporin I | (SEQ ID NO: 5)<br>atgGGCAAAG TGTGGGATTG GATTAAAAGC ACCGCGAAAA<br>AACTGTGGAA CAGCGAACCG GTGAAAGAAC TGAAAAACAC<br>CGCGCTGAAC GCGGCGAAAA ACCTGGTGGC GGAAAAAATT<br>GGCGCGACCC CGAGCTAA<br><br>(SEQ ID NO: 6)<br>MGKVWDWIKS TAKKLWNSEP VKELKNTALN AAKNLVAEKI<br>GATPS | 74 |

CONCLUSIONS

Figure 6:
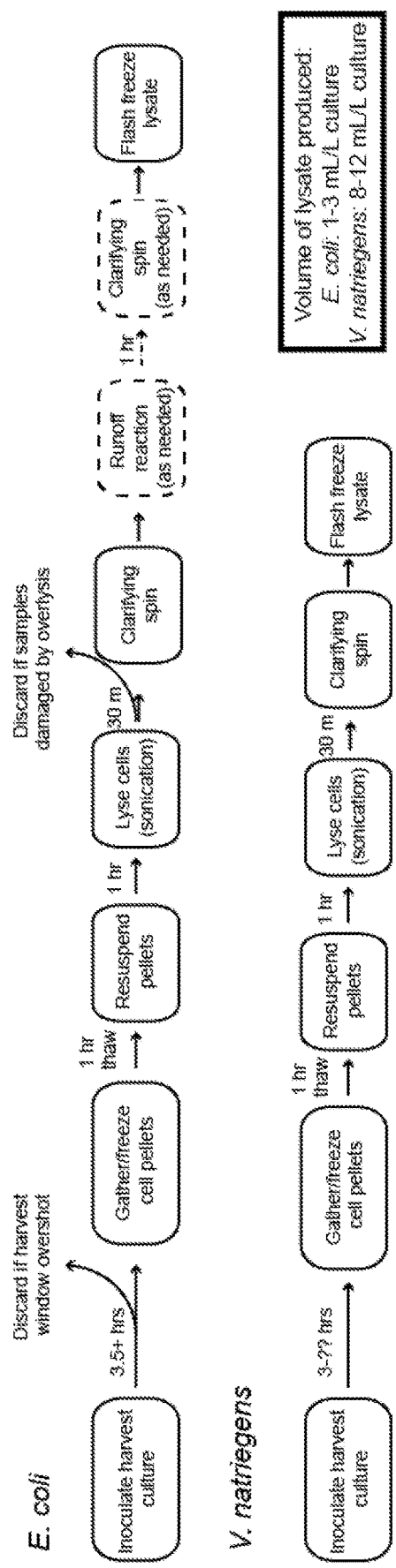
FIG. 6. Comparison of *E. coli* and *V. natriegens* lysate preparation workflows. As compared to *E. coli*, *V. natriegens* cells are easier to handle both in the context of culture harvest and lysis. It is extremely difficult to spoil a *V. natriegens* extract preparation. *V. natriegens*' overall workflow is faster due to the organism's rapid growth rate and omission of any runoff reaction step. Finally, because *V. natriegens* pellets are gathered at stationary phase, they are significantly larger than those gathered for *E. coli*—consequently, the volume of *V. natriegens* lysate derived from a single 1 L harvest is significantly higher. Bullet points: For basically every aspect of lysate preparation, *V. natriegens* is less temperamental then *E. coli* and thus easier to work with; *V. natriegens* workflow is faster than the *E. coli* workflow; and 1 L of *V. natriegens* cell culture yields an order of magnitude more lysate than 1 L of *E. coli* culture.

In this study, we present the development of a novel CFPS platform composed of crude lysates derived from the non-model bacterium *V. natriegens* (FIG. 6). We identified optimal culture harvest conditions for this organism, demonstrating that culturing in BHI media supplemented with v2 salts and harvesting at stationary phase is optimal for the generation of productive lysates. This feature is convenient, as it eliminates the need to collect cell pellets within a tightly specific $OD_{600}$ window in order to preserve lysate quality. Researchers can "set and forget" *V. natriegens* cultures and harvest whenever it is convenient without worrying about spoiling the resulting extracts. Attempts to optimize lysis parameters revealed that *V. natriegens* lysates are highly-resistant to damage via overlysis, and overall the system is relatively agnostic to both lysis buffer resuspension volume and lysis energy delivery. Surprisingly, the system is much less sensitive to overlysis during lysate preparation as compared to *E. coli*-based systems, a huge benefit for first-time or inexperienced CFPS users.

for cloning and recombinant protein expression[47,48], but the knowledge base for this organism still lags behind the more established *E. coli* with regards to regulatory sequences such as promoters, terminators, and ribosome binding sites (RBSs). Due to its open and easily-accessible nature, the CFPS platform developed here could be used to interrogate many such parts in parallel for rapid characterization. The resulting data could in turn be used to inform construct design for use in vivo, supporting the increasing interest in using this organism as an alternative to *E. coli* for molecular biological applications. This idea has already been briefly explored using a *V. natriegens*-based CFPS platform[71].

Perhaps the most surprising finding to arise from this effort was that the most productive *V. natriegens* extracts are derived from stationary phase cells. This not only contradicts what is usually found in other bacterial CFPS systems, but is also is overall difficult to rationalize alongside the generally-accepted notion that ribosomes are downregulated in stationary phase[55]. It is possible that sequestration of ribosomes by native mRNAs in lysates derived from exponential phase cells accounts for the relatively low productivity of these lysates, despite the presence of a larger ribosome pool. In other systems this issue is alleviated by subjecting the lysate to a run-off reaction[3,52,54,56,57], but this approach was not successful here.

Going forward, we expect the efficacy of *V. natriegens* CFPS to improve rapidly. Indeed, the system development and characterization described here accomplished in a very short amount of time what took decades of research and development in *E. coli*. Exploration of the use of alternative energy regeneration systems is one obvious future direction. Indeed, development of an entirely novel energy regeneration system (perhaps using sucrose as the starting substrate[48]) might ultimately be required to fully optimize *V. natriegens* CFPS. Another fruitful direction is in the screening of a larger, more comprehensive library of negative effector knockout strains. This could perhaps be informed by a time course analysis of small molecule concentrations in CFPS reactions, with knockouts targeted towards metabolic pathways that might be siphoning away critical substrates.

In conclusion, the Vnat cell-free platform is excellent for early forays into the use of CFPS systems, as the cells are fast and easy to grow, easy to lyse, and a high volume of active lysate is generated from as little as 1 L of cell culture. Collectively, these features reduce the need for specialized knowledge and equipment that have limited the use of CFPS. We expect that this reduced entry barrier will facilitate the spread of these systems into new areas for use on exciting, novel applications in synthetic biology.

Methods

Strains and Plasmids.

The bacterial strains and plasmids used in this study are listed in Table 2. *V. natriegens* was purchased from the American Type Culture Collection (ATCC® 14048™). Vmax™ Express was purchased from SGI-DNA, a subsidiary of Synthetic Genomics, Inc. pJL1 plasmids encoding the antimicrobial peptides were synthesized and assembled by Twist Bioscience. Assembled plasmids were submitted to the NUSeq Core facility along with forward primers, and sequences were confirmed using traditional Sanger sequencing. Kanamycin (50 µg/mL) was used for maintaining pJL1-based plasmids. Chloramphenicol (34 µg/mL) was used to select for all negative effector knockout mutants.

TABLE 2

Strains and plasmids used in this study. $Km^R$ and $Cm^R$ are kanamycin and chloramphenicol resistance, respectively.

| Strains and plasmids | Genotype/relevant characteristics | Source |
|---|---|---|
| Strains | | |
| BL21 Star ™ (DE3) | F⁻ ompT hsdS$_B$ (r$_B^-$m$_B^-$) gal dcm rne131 (DE3) | Life Technologies |
| *V. natriegens* | ATCC ® 14048 ™ | ATCC |
| Vmax ™ Express | ΔDns*, IPTG-inducible T7 RNAP (Cat. No. CL1100) | Synthetic Genomics, Inc. |
| Plasmids | | |
| pJL1-sfGFP | $Km^R$, $P_{T7}$, super folder green fluorescent protein (sfGFP), C-terminal strep-tag | 89 |
| pJL1-cecropinA | $Km^R$, $P_{T7}$, cecropin A | This study |
| pJL1-cecropinP1 | $Km^R$, $P_{T7}$, cecropin P1 | This study |
| pJL1-opistoporinI | $Km^R$, $P_{T7}$, opistoporin I | This study |
| pJL1-pyrrhocoricin | $Km^R$, $P_{T7}$, pyrrhocoricin | This study |

*Dns is the conventional name for the endA homolog in Vibrio species

Cell Culture.

*V. natriegens* cells were grown in BHI media supplemented with v2 salts (204 mM NaCl, 4.2 mM KCl, 23.14 mM $MgCl_2$) unless noted otherwise. For confirmation of *V. natriegens* growth rate, 100 µL cultures were assembled in a clear 96-well plate (Costar 3370; Corning, Corning, N.Y.) and shaken at 250 RPM at 37° C. for 20 hr in a Synergy H1 plate reader (BioTek, Winooski, Vt.) which continuously monitored the $OD_{600}$ of each sample. To minimize sample evaporation, plates were covered and sealed with Parafilm®. Doubling times were calculated using timepoints corresponding to $OD_{600}$ values between 0.02 and 0.2. For cultures performed at 1 L scale, cells were grown in a 2.5 L Tunair® shake flask and incubated at 37° C. at 250 RPM. Except for experiments performed to identify optimal harvest $OD_{600}$, cultures were grown until the onset of stationary phase (an approx. $OD_{600}$ of 6.5-7.5). 1 mM isopropyl β-D-1-thiogalactopyranoside (IPTG) was added to cultures of Vmax™ Express cells between $OD_{600}$ 0.6-0.8 to induce expression of T7 RNA polymerase. In all cases, cells were pelleted by centrifuging for 15 mM at 5000×g at 4° C., washed three times with cold S30 buffer (10 mM tris-acetate pH 8.2, 14 mM magnesium acetate, 60 mM potassium acetate, 2 mM dithiothreitol)[72], and stored at −80° C. until lysed.

Extract Preparation.

Unless otherwise noted, cell pellets were thawed and suspended in 0.8 mL of S30 buffer per gram of wet cell mass. Prior to the optimization of lysis parameters, cell pellets were instead resuspended in 1.0 mL buffer per gram of cells. Following suspension, 1.4 mL of cell slurry was transferred into 1.5 mL microtubes. The cells were lysed using a Q125 Sonicator (Qsonica, Newtown, Conn.) with 3.175 mm diameter probe at a 20 kHz frequency and 50% amplitude. Sonication was continued for three cycles of 45s ON/59s OFF unless stated otherwise. To minimize heat damage during sonication, samples were placed in an ice-water bath. For each 1.4 mL sample, the input energy was ~270 Joules/sonication cycle. The lysate was then centrifuged at 12,000×g at 4° C. for 10 min. The supernatant was flash-frozen using liquid nitrogen and stored at −80° C. until use. For preparations including a runoff reaction, following the first clarifying spin supernatant was transferred to a new tube and subjected to a 1 hr incubation at 30° C. or 37° C., either stationary or with shaking at 250 RPM. Following this incubation, samples were centrifuged at 10,000×g at 4° C. for 10 min after which supernatant was flash-frozen and stored at −80° C. until use.

CFPS Reaction.

A modified PANOx-SP system was utilized for CFPS reactions. Briefly, a 15 µL CFPS reaction in a 2.0 mL microtube was prepared by mixing the following components: 1.2 mM ATP; 0.85 mM each of GTP, UTP, and CTP; 34 µg/mL folinic acid; 170 µg/mL of *E. coli* tRNA mixture; 13.3 µg/mL plasmid; 16 µg/mL T7 RNA polymerase; 3 mM for each of the 20 standard amino acids; 0.33 mM nicotinamide adenine dinucleotide (NAD); 0.27 mM coenzyme-A (CoA); 1.5 mM spermidine; 1 mM putrescine; 4 mM sodium oxalate; 290 mM potassium glutamate; 10 mM ammonium glutamate; 6 mM magnesium glutamate; 57 mM HEPES, pH 7.2; 67 mM phosphoenolpyruvate (PEP), and 4 µL (27% v/v) of cell extract. Each CFPS reaction was incubated for 20 hr at 30° C. unless noted otherwise. Experiments performed prior to determining an optimal reagent mix for *V. natriegens* lysates used the above mix with the following changes: 2 mM for each of the 20 standard amino acids, 130 mM potassium glutamate, 10 mM magnesium glutamate, and 33 mM PEP were used instead. As individual reagent concentrations were optimized, their optimal value listed above were used for all reactions from that point onward. *E. coli* total tRNA mixture (from strain MRE600) and phosphoenolpyruvate was purchased from Roche Applied Science (Indianapolis, Ind.). ATP, GTP, CTP, UTP, 20 amino acids and other materials were purchased from Sigma (St. Louis, Mo.) without further purification. T7RNAP was purified in house as described previously[3]. To direct synthesis of a specific product, 200 ng of pJL1 template plasmid encoding the product was added to each reaction.

Quantification of Active sfGFP.

CFPS reactions were diluted 1:25 in nanopure water and active full-length sfGFP protein yields were quantified by measuring fluorescence using a Synergy 2 plate reader (BioTek, Winooski, Vt.) with excitation at 485 nm, emission at 528 nm, and cut-off at 510 nm in 96-well half area black plates (Costar 3694; Corning, Corning, N.Y.). sfGFP fluorescence units were converted to concentration using a standard curve established with $^{14}$C-Leu quantified sfGFP as described previously[54].

CFPS Lyophilization.

Samples were assembled in 2 mL microtubes and lyophilized overnight using a VirTis BenchTop Pro Freeze Dryer (SP Scientific, Warminster, Pa.). Lyophilized samples were stored at room temperature under vacuum in a dessicator with Drierite desiccant. For reconstitution of fully-assembled reactions, template plasmid DNA plus nuclease-free water were added to each sample. Samples consisting of only lyophilized lysate were reconstituted with the complete CFPS reagent mix. Where indicated, lyophilized reactions were supplemented with 2.5% (m/v) trehalose.

Quantification of Antimicrobial Peptide Yield in CFPS.

Radioactive $^{14}$C-Leucine was added into 15 µL CFPS reactions to a final concentration of 25 µM. After incubation, yields were quantified by determining radioactive $^{14}$C-Leu incorporation into peptides precipitated in 15% (m/v) trichloroacetic acid (TCA)[72]. Radioactivity of TCA-precipitated samples was measured using liquid scintillation counting (MicroBeta2, PerkinElmer, Waltham, Mass.).

REFERENCES

1 Carlson, E. D., Gan, R., Hodgman, C. E. & Jewett, M. C. Cell-free protein synthesis: applications come of age. Biotechnology advances 30, 1185-1194, doi:10.1016/j.biotechadv.2011.09.016 (2012).
2 Martin, R. W. et al. Development of a CHO-Based Cell-Free Platform for Synthesis of Active Monoclonal Antibodies. ACS synthetic biology 6, 1370-1379, doi: 10.1021/acssynbio.7b00001 (2017).
3 Martin, R. W. et al. Cell-free protein synthesis from genomically recoded bacteria enables multisite incorporation of noncanonical amino acids. Nature communications 9, 1203, doi:10.1038/s41467-018-03469-5 (2018).
4 Lu, Y. Cell-free synthetic biology: Engineering in an open world. Synthetic and systems biotechnology 2, 23-27, doi:10.1016/j.synbio.2017.02.003 (2017).
5 Jewett, M. C. & Swartz, J. R. Mimicking the *Escherichia coli* cytoplasmic environment activates long-lived and efficient cell-free protein synthesis. Biotechnology and bioengineering 86, 19-26, doi:10.1002/bit.20026 (2004).
6 Caschera, F. & Noireaux, V. Synthesis of 2.3 mg/ml of protein with an all *Escherichia coli* cell-free transcription-translation system. Biochimie 99, 162-168, doi:10.1016/j.biochi.2013.11.025 (2014).
7 Zawada, J. F. et al. Microscale to manufacturing scale-up of cell-free cytokine production—a new approach for shortening protein production development timelines. Biotechnology and bioengineering 108, 1570-1578, doi: 10.1002/bit.23103 (2011).
8 Jewett, M. C., Calhoun, K. A., Voloshin, A., Wuu, J. J. & Swartz, J. R. An integrated cell-free metabolic platform for protein production and synthetic biology. Molecular systems biology 4, 220, doi:10.1038/msb.2008.57 (2008).
9 Buntru, M., Vogel, S., Spiegel, H. & Schillberg, S. Tobacco BY-2 cell-free lysate: an alternative and highly-productive plant-based in vitro translation system. BMC biotechnology 14, 37, doi:10.1186/1472-6750-14-37 (2014).
10 Buntru, M., Vogel, S., Stoff, K., Spiegel, H. & Schillberg, S. A versatile coupled cell-free transcription-translation system based on tobacco BY-2 cell lysates. Biotechnology and bioengineering 112, 867-878, doi:10.1002/bit.25502 (2015).
11 Thoring, L., Dondapati, S. K., Stech, M., Wustenhagen, D. A. & Kubick, S. High-yield production of "difficult-to-express" proteins in a continuous exchange cell-free system based on CHO cell lysates. Scientific reports 7, 11710, doi:10.1038/s41598-017-12188-8 (2017).
12 Penalber-Johnstone, C. et al. Optimizing cell-free protein expression in CHO: Assessing small molecule mass transfer effects in various reactor configurations. Biotechnology and bioengineering 114, 1478-1486, doi:10.1002/bit.26282 (2017).
13 Chappell, J., Jensen, K. & Freemont, P. S. Validation of an entirely in vitro approach for rapid prototyping of DNA regulatory elements for synthetic biology. Nucleic acids research 41, 3471-3481, doi:10.1093/nar/gkt052 (2013).
14 Takahashi, M. K. et al. Characterizing and prototyping genetic networks with cell-free transcription-translation reactions. Methods 86, 60-72, doi:10.1016/j.ymeth.2015.05.020 (2015).
15 Karim, A. S. & Jewett, M. C. A cell-free framework for rapid biosynthetic pathway prototyping and enzyme discovery. Metabolic engineering 36, 116-126, doi:10.1016/j.ymben.2016.03.002 (2016).
16 Dudley, Q. M., Anderson, K. C. & Jewett, M. C. Cell-Free Mixing of *Escherichia coli* Crude Extracts to Prototype and Rationally Engineer High-Titer Mevalonate Synthesis. ACS synthetic biology 5, 1578-1588, doi:10.1021/acssynbio.6b00154 (2016).
17 Watanabe, M. et al. Cell-free protein synthesis for structure determination by X-ray crystallography. Methods in molecular biology 607, 149-160, doi:10.1007/978-1-60327-331-2_13 (2010).
18 Martemyanov, K. A., Shirokov, V. A., Kurnasov, O. V., Gudkov, A. T. & Spirin, A. S. Cell-free production of biologically active polypeptides: application to the synthesis of antibacterial peptide cecropin. Protein expression and purification 21, 456-461, doi:10.1006/prep.2001.1400 (2001).
19 Renesto, P. & Raoult, D. From genes to proteins: in vitro expression of rickettsial proteins. Annals of the New York Academy of Sciences 990, 642-652 (2003).
20 Xu, Z., Chen, H., Yin, X., Xu, N. & Cen, P. High-level expression of soluble human beta-defensin-2 fused with green fluorescent protein in *Escherichia coli* cell-free system. Applied biochemistry and biotechnology 127, 53-62 (2005).
21 Sullivan, C. J. et al. A cell-free expression and purification process for rapid production of protein biologics. Biotechnology journal 11, 238-248, doi:10.1002/biot.201500214 (2016).

22. Li, J. et al. Cell-free protein synthesis enables high yielding synthesis of an active multicopper oxidase. Biotechnology journal 11, 212-218, doi:10.1002/biot.201500030 (2016).

23. Heinzelman, P., Schoborg, J. A. & Jewett, M. C. pH responsive granulocyte colony-stimulating factor variants with implications for treating Alzheimer's disease and other central nervous system disorders. Protein engineering, design & selection: PEDS 28, 481-489, doi:10.1093/protein/gzv022 (2015).

24. Kightlinger, W. et al. Design of glycosylation sites by rapid synthesis and analysis of glycosyltransferases. Nature chemical biology, doi:10.1038/s41589-018-0051-2 (2018).

25. Schoborg, J. A. et al. A cell-free platform for rapid synthesis and testing of active oligosaccharyltransferases. Biotechnology and bioengineering 115, 739-750, doi:10.1002/bit.26502 (2018).

26. Gurramkonda, C. et al. Improving the recombinant human erythropoietin glycosylation using microsome supplementation in CHO cell-free system. Biotechnology and bioengineering 115, 1253-1264, doi:10.1002/bit.26554 (2018).

27. Jaroentomeechai, T. et al. Single-pot glycoprotein biosynthesis using a cell-free transcription-translation system enriched with glycosylation machinery. Nature communications 9, 2686, doi:10.1038/s41467-018-05110-x (2018).

28. Pardee, K. et al. Rapid, Low-Cost Detection of Zika Virus Using Programmable Biomolecular Components. Cell 165, 1255-1266, doi:10.1016/j.cell.2016.04.059 (2016).

29. Slomovic, S., Pardee, K. & Collins, J. J. Synthetic biology devices for in vitro and in vivo diagnostics. Proceedings of the National Academy of Sciences of the United States of America 112, 14429-14435, doi:10.1073/pnas.1508521112 (2015).

30. Gootenberg, J. S. et al. Nucleic acid detection with CRISPR-Cas13a/C2c2. Science 356, 438-442, doi:10.1126/science.aam9321 (2017).

31. Pardee, K. et al. Portable, On-Demand Biomolecular Manufacturing. Cell 167, 248-259 e212, doi:10.1016/j.cell.2016.09.013 (2016).

32. Karig, D. K., Bessling, S., Thielen, P., Zhang, S. & Wolfe, J. Preservation of protein expression systems at elevated temperatures for portable therapeutic production. Journal of the Royal Society, Interface 14, doi:10.1098/rsif.2016.1039 (2017).

33. Smith, M. T., Berkheimer, S. D., Werner, C. J. & Bundy, B. C. Lyophilized *Escherichia coli*-based cell-free systems for robust, high-density, long-term storage. BioTechniques 56, 186-193, doi:10.2144/000114158 (2014).

34. Hunt, J. P., Yang, S. O., Wilding, K. M. & Bundy, B. C. The growing impact of lyophilized cell-free protein expression systems. Bioengineered 8, 325-330, doi:10.1080/21655979.2016.1241925 (2017).

35. Adiga, R. et al. Point-of-care production of therapeutic proteins of good-manufacturing-practice quality. Nature Biomedical Engineering, doi:10.1038/s41551-018-0259-1 (2018).

36. Stark, J. C. et al. BioBits Bright: a fluorescent synthetic biology education kit. Science Advances (2018).

37. Huang, A. et al. BioBits Explorer: a modular synthetic biology education kit. Science Advances (2018).

38. Hodgman, C. E. & Jewett, M. C. Optimized extract preparation methods and reaction conditions for improved yeast cell-free protein synthesis. Biotechnology and bioengineering 110, 2643-2654, doi:10.1002/bit.24942 (2013).

39. Zemella, A., Thoring, L., Hoffmeister, C. & Kubick, S. Cell-free protein synthesis: pros and cons of prokaryotic and eukaryotic systems. Chembiochem: a European journal of chemical biology 16, 2420-2431, doi:10.1002/cbic.201500340 (2015).

40. Li, J., Wang, H., Kwon, Y. C. & Jewett, M. C. Establishing a high yielding *streptomyces*-based cell-free protein synthesis system. Biotechnology and bioengineering 114, 1343-1353, doi:10.1002/bit.26253 (2017).

41. Li, J., Wang, H. & Jewett, M. C. Expanding the palette of *Streptomyces*-based cell-free protein synthesis systems with enhanced yields. Biochemical engineering journal 130, 29-33, doi:10.1016/j.bej.2017.11.013 (2018).

42. Moore, S. J., Lai, H. E., Needham, H., Polizzi, K. M. & Freemont, P. S. *Streptomyces venezuelae* TX-TL—a next generation cell-free synthetic biology tool. Biotechnology journal 12, doi:10.1002/biot.201600678 (2017).

43. Kelwick, R., Webb, A. J., MacDonald, J. T. & Freemont, P. S. Development of a *Bacillus subtilis* cell-free transcription-translation system for prototyping regulatory elements. Metabolic engineering 38, 370-381, doi:10.1016/j.ymben.2016.09.008 (2016).

44. Moore, S. J. et al. Rapid acquisition and model-based analysis of cell-free transcription-translation reactions from nonmodel bacteria. Proceedings of the National Academy of Sciences of the United States of America 115, E4340-E4349, doi:10.1073/pnas.1715806115 (2018).

45. Payne, W. J. Studies on bacterial utilization of uronic acids. III. Induction of oxidative enzymes in a marine isolate. Journal of bacteriology 76, 301-307 (1958).

46. Eagon, R. G. *Pseudomonas natriegens*, a marine bacterium with a generation time of less than 10 minutes. Journal of bacteriology 83, 736-737 (1962).

47. Weinstock, M. T., Hesek, E. D., Wilson, C. M. & Gibson, D. G. *Vibrio natriegens* as a fast-growing host for molecular biology. Nature methods 13, 849-851, doi:10.1038/nmeth.3970 (2016).

48. Lee, H. H. et al. *Vibrio natriegens*, a new genomic powerhouse. bioRxiv 058487, doi:https://doi.org/10.1101/058487 (2016).

49. Zawada, J. & Swartz, J. Effects of growth rate on cell extract performance in cell-free protein synthesis. Biotechnology and bioengineering 94, 618-624, doi:10.1002/bit.20831 (2006).

50. Bremer, H. & Dennis, P. *Escherichia coli* and *Salmonella*: Cellular and Molecular Biology. 2 edn, Vol. 1 1553-1569 (ASM Press, 1996).

51. Aiyar, S. E., Gaal, T. & Gourse, R. L. rRNA promoter activity in the fast-growing bacterium *Vibrio natriegens*. Journal of bacteriology 184, 1349-1358 (2002).

52. Kwon, Y. C. & Jewett, M. C. High-throughput preparation methods of crude extract for robust cell-free protein synthesis. Scientific reports 5, 8663, doi:10.1038/srep08663 (2015).

53. Wang, H., Li, J. & Jewett, M. C. Development of a *Pseudomonas putida* cell-free protein synthesis platform for rapid screening of gene regulatory elements. Synthetic Biology 3, ysy003-ysy003, doi:10.1093/synbio/ysy003 (2018).

54. Hong, S. H. et al. Improving cell-free protein synthesis through genome engineering of *Escherichia coli* lacking 55 Failmezger, J., Rauter, M., Nitschel, R., Kraml, M. & Siemann-Herzberg, M. Cell-free protein synthesis from non-growing, stressed *Escherichia coli*. Scientific reports 7, 16524, doi:10.1038/s41598-017-16767-7 (2017).

56 Liu, D. V., Zawada, J. F. & Swartz, J. R. Streamlining *Escherichia coli* S30 extract preparation for economical cell-free protein synthesis. Biotechnology progress 21, 460-465, doi:10.1021/bp049789y (2005).

57 Nirenberg, M. W. Cell-Free Protein Synthesis Directed by Messenger Rna. Method Enzymol 6, 17-23, doi:Doi 10.1016/0076-6879(63)06142-5 (1963).

58 Jewett, M. C., Fritz, B. R., Timmerman, L. E. & Church, G. M. In vitro integration of ribosomal RNA synthesis, ribosome assembly, and translation. Molecular systems biology 9, 678, doi:10.1038/msb.2013.31 (2013).

59 Fagerbakke, K. M., Norland, S. & Heldal, M. The inorganic ion content of native aquatic bacteria. Canadian journal of microbiology 45, 304-311 (1999).

60 Petrov, A. S. et al. RNA-magnesium-protein interactions in large ribosomal subunit. The journal of physical chemistry. B 116, 8113-8120, doi:10.1021/jp304723w (2012).

61 Voloshin, A. M. & Swartz, J. in Cell-Free Protein Synthesis: Methods and Protocols Vol. 1 (eds A. S. Spirin & J. Swartz) Ch. 12, 207-235 (Wiley-VCH Verlab GmbH & Co. KGaA, 2008).

62 Smith, M. T., Bennett, A. M., Hunt, J. M. & Bundy, B. C. Creating a completely "cell-free" system for protein synthesis. Biotechnology progress 31, 1716-1719, doi: 10.1002/btpr.2157 (2015).

63 Gross, A., Hashimoto, C., Sticht, H. & Eichler, J. Synthetic Peptides as Protein Mimics. Frontiers in bioengineering and biotechnology 3, 211, doi:10.3389/fbioe.2015.00211 (2015).

64 Haussner, C., Lach, J. & Eichler, J. Synthetic antibody mimics for the inhibition of protein-ligand interactions. Current opinion in chemical biology 40, 72-77, doi: 10.1016/j.cbpa.2017.07.001 (2017).

65 Devkota, A. K., Kaoud, T. S., Warthaka, M. & Dalby, K. N. Fluorescent peptide assays for protein kinases. Current protocols in molecular biology Chapter 18, Unit 18 17, doi:10.1002/0471142727.mb1817s91 (2010).

66 Bengtsson-Palme, J., Kristiansson, E. & Larsson, D. G. J. Environmental factors influencing the development and spread of antibiotic resistance. FEMS microbiology reviews 42, doi:10.1093/femsre/fux053 (2018).

67 Li, Y. F. Recombinant production of antimicrobial peptides in *Escherichia coli*: A review (vol 80, pg 206, 2011). Protein expression and purification 82, 252-252, doi: 10.1016/j.pep.2011.11.006 (2012).

68 Zhao, Q., Xu, W., Xing, L. & Lin, Z. Recombinant production of medium- to large-sized peptides in *Escherichia coli* using a cleavable self-aggregating tag. Microbial cell factories 15, 136, doi:10.1186/s12934-016-0534-3 (2016).

69 Silvestro, L., Weiser, J. N. & Axelsen, P. H. Antibacterial and antimembrane activities of cecropin A in *Escherichia coli*. Antimicrobial agents and chemotherapy 44, 602-607 (2000).

70 Dalia, T. N. et al. Multiplex Genome Editing by Natural Transformation (MuGENT) for Synthetic Biology in *Vibrio natriegens*. ACS synthetic biology 6, 1650-1655, doi:10.1021/acssynbio.7b00116 (2017).

71 Failmezger, J., Scholz, S., Blombach, B. & Siemann-Herzberg, M. Cell-free protein synthesis from fast-growing *Vibrio natrigens*. Front Microbiol, doi:10.3389/fmicb.2018.01146 (2018).

72 Swartz, J. R., Jewett, M. C. & Woodrow, K. A. Cell-free protein synthesis with prokaryotic combined transcription-translation. Methods in molecular biology 267, 169-182, doi:10.1385/1-59259-774-2:169 (2004).

73 Silvestro, L., Weiser, J. N. & Axelsen, P. H. Antibacterial and antimembrane activities of cecropin A in *Escherichia coli*. Antimicrobial agents and chemotherapy 44, 602-607 (2000).

74 Pardee, K. et al. Portable, On-Demand Biomolecular Manufacturing. Cell 167, 248-259 e212, doi:10.1016/j.cell.2016.09.013 (2016).

75 Hong, S. H. et al. Improving cell-free protein synthesis through genome engineering of *Escherichia coli* lacking release factor 1. Chembiochem: a European journal of chemical biology 16, 844-853, doi:10.1002/cbic.201402708 (2015).

76 Michel-Reydellet, N., Woodrow, K. & Swartz, J. Increasing PCR fragment stability and protein yields in a cell-free system with genetically modified *Escherichia coli* extracts. Journal of molecular microbiology and biotechnology 9, 26-34, doi: 10.1159/000088143 (2005).

77 Borja, G. M. et al. Engineering *Escherichia coli* to increase plasmid DNA production in high cell-density cultivations in batch mode. Microbial cell factories 11, 132, doi:10.1186/1475-2859-11-132 (2012).

78 Jiang, X. et al. Reduction of protein degradation by use of protease-deficient mutants in cell-free protein synthesis system of *Escherichia coli*. Journal of bioscience and bioengineering 93, 151-156 (2002).

79 Zhang, Y. et al. MazF cleaves cellular mRNAs specifically at ACA to block protein synthesis in *Escherichia coli*. Molecular cell 12, 913-923 (2003).

80 Goerke, A. R., Loening, A. M., Gambhir, S. S. & Swartz, J. R. Cell-free metabolic engineering promotes high-level production of bioactive *Gaussia princeps* luciferase. Metabolic engineering 10, 187-200, doi:10.1016/j.ymben.2008.04.001 (2008).

81 Raines, R. T. Ribonuclease A. Chemical reviews 98, 1045-1066 (1998).

82 Kushner, S. R. mRNA decay in *Escherichia coli* comes of age. Journal of bacteriology 184, 4658-4665; discussion 4657 (2002).

83 Airen, I. O. Genome-wide functional genomic analysis for physiological investigation and improvement of cell-free protein synthesis PhD thesis, Stanford University, (2011).

84 Lin, E. C. Glycerol dissimilation and its regulation in bacteria. Annual review of microbiology 30, 535-578, doi:10.1146/annurev.mi.30.100176.002535 (1976).

85 Rittmann, D., Lindner, S. N. & Wendisch, V. F. Engineering of a glycerol utilization pathway for amino acid production by *Corynebacterium glutamicum*. Applied and environmental microbiology 74, 6216-6222, doi:10.1128/AEM.00963-08 (2008).

86 Bundy, B. C. & Swartz, J. R. Efficient disulfide bond formation in virus-like particles. Journal of biotechnology 154, 230-239, doi:10.1016/j.jbiotec.2011.04.011 (2011).

87 Calhoun, K. A. & Swartz, J. R. Total amino acid stabilization during cell-free protein synthesis reactions. Journal of biotechnology 123, 193-203, doi:10.1016/j.jbiotec.2005.11.011 (2006).

88 Michel-Reydellet, N., Calhoun, K. & Swartz, J. Amino acid stabilization for cell-free protein synthesis by modification of the *Escherichia coli* genome. Metabolic engineering 6, 197-203, doi:10.1016/j.ymben.2004.01.003 (2004).

89 Bundy, B. C. & Swartz, J. R. Site-specific incorporation of p-propargyloxyphenylalanine in a cell-free environment for direct protein-protein click conjugation. Bioconjugate chemistry 21, 255-263, doi:10.1021/bc9002844 (2010).

In the foregoing description, it will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

All methods described herein can be performed in any suitable order unless otherwise indicated herein or otherwise clearly contradicted by context. The use of any and all examples provided herein, is intended merely to better illuminate the invention and does not pose a limitation on the scope of the invention unless otherwise claimed. No language in the specification should be construed as indicating any non-claimed element as essential to the practice of the invention.

Citations to a number of patent and non-patent references are made herein. The cited references are incorporated by reference herein in their entireties. In the event that there is an inconsistency between a definition of a term in the specification as compared to a definition of the term in a cited reference, the term should be interpreted based on the definition in the specification.

We claim:

1. A platform for in vitro transcription of mRNA and/or translation of peptides, polypeptides, or sequence defined polymers, the platform comprising a cellular extract prepared from a cell culture of a species of *Vibrio*; wherein the *Vibrio* cells in the culture are in stationary phase immediately prior to extract preparation.

2. The platform of claim 1, wherein the species of *Vibrio* is *Vibrio natriegens*.

3. The platform of claim 1, wherein the species of *Vibrio* cells are engineered to be deficient in a negative effector for cell-free protein synthesis (CFPS).

4. The platform of claim 3, wherein the negative effector for CFPS is selected from the group consisting of a homolog of *E. coli* endA, mazF, rna, rnb, rne, gor, lon, ompT, gdhA, gshA, sdaA, sdaB, speA, WaaL, tnaA, glpK, and any combination thereof.

5. The platform of claim 1, wherein the *Vibrio* cells are engineered to express an upregulated gene product that is a positive effector for CFPS.

6. The platform of claim 5, wherein the positive effector for CFPS is selected from the group consisting of a homolog of *E. coli* ackA, ndk, pykF, cdd, dsbC, dnaK, dnaJ, crpE, tig, groS, groL, infA, infB, fusA, efp, lepA, tufB, hs1R, ffr, and any combination thereof.

7. The platform of claim 1, wherein the species of Vibrio is engineered to be deficient in a release factor 1.

8. The platform of claim 1, wherein the *Vibrio* cells have been genomically-recoded to replace one or more stop codons with a different codon.

9. The platform of claim 1, wherein the *Vibrio* has cells have been engineered to express T7 RNA polymerase.

10. The platform of claim 1, wherein the stationary phase is defined as the cell culture having an $OD_{600}$ of greater than about 3.0.

11. The platform of claim 1, wherein the cellular extract comprises an S12 and/or S30 fraction of the cell culture.

12. The platform of claim 1, further comprising one or more components selected from the group consisting of amino acids which include non- canonical amino acids, NTPs, salts, cofactors, an energy source and an energy source comprising a phosphate group or non-phosphorylated energy group, a translation template, a transcription template, and any combination thereof.

13. The platform of claim 1, further comprising an energy source, wherein the energy source is present at a concentration in a range of greater than about 30 mM, to less than about 100 mM, or within a concentration range bounded by these values.

14. The platform of claim 1, further comprising a source of potassium ($K^+$), wherein the platform comprises potassium at a concentration in a range of greater than about 50 mM, to less than about 500 mM, or within a concentration range bounded by of these values; and/or further comprising a source of magnesium ($Mg^+$), wherein the platform comprises magnesium at a concentration in a range of greater than about 1 mM to less than about 30 mM, or within a concentration range bounded by these values.

15. The platform of claim 1, wherein the platform or one or more components of the platform are preserved such as through freeze-drying.

16. A method for in vitro transcription of mRNA and/or translation of a peptide, a polypeptide, or a sequence defined polymer, the method comprising transcribing a transcription templated encoding the mRNA and/or translating in vitro an mRNA encoding the sequence defined polymer, polypeptide, or peptide in the platform of claim 1.

17. The method of claim 16, wherein the method comprises transcribing a DNA template in the platform to provide the translated mRNA.

18. The method of claim 16, wherein the method is performed at a temperature between about 20-40° C.

19. The platform of claim 12, wherein the energy source comprises one or more molecules selected from the group consisting of phosphoenol pyruvate (PEP), glucose, and pyruvate.

20. The platform of claim 13, wherein the energy source is present at a concentration greater than 67 mM.

21. The platform of claim 14, wherein the platform comprises potassium at a concentration of about 300 mM and/or further comprising magnesium at a concentration of about 8 mM.

* * * * *

UNITED STATES PATENT AND TRADEMARK OFFICE
CERTIFICATE OF CORRECTION

PATENT NO. : 11,673,921 B2
APPLICATION NO. : 16/762889
DATED : June 13, 2023
INVENTOR(S) : Michael Christopher Jewett et al.

It is certified that error appears in the above-identified patent and that said Letters Patent is hereby corrected as shown below:

In the Specification

Column 30, Line 66, "nature ss Thus," should be --nature$^{5, 58}$. Thus--.

Column 36, Line 20, "mM" should be --min--.

In the Claims

Column 99, Claim 9, Line 31, "Vibrio has cells" should be --Vibrio cells--.

Column 100, Claim 15, Line 18, "preserved such as through" should be --preserved through--.

Signed and Sealed this
Eighth Day of August, 2023

Katherine Kelly Vidal
*Director of the United States Patent and Trademark Office*

```
                         SEQUENCE LISTING

<160> NUMBER OF SEQ ID NOS: 30

<210> SEQ ID NO 1
<211> LENGTH: 117
<212> TYPE: DNA
<213> ORGANISM: Artificial
<220> FEATURE:
<223> OTHER INFORMATION: DNA sequence encoding Cecropin A peptide

<400> SEQUENCE: 1
atgaagtgga aattgtttaa aaagatcgaa aaggtggggc aaaatatccg cgacgggatc      60
attaaggcag gtccggctgt ggcggtcgtt ggtcaggcaa cgcaaatcgc aaaataa       117

<210> SEQ ID NO 2
<211> LENGTH: 38
<212> TYPE: PRT
<213> ORGANISM: Artificial
<220> FEATURE:
<223> OTHER INFORMATION: Amino acid sequence of Cecropin A peptide

<400> SEQUENCE: 2

Met Lys Trp Lys Leu Phe Lys Lys Ile Glu Lys Val Gly Gln Asn Ile
1               5                   10                  15

Arg Asp Gly Ile Ile Lys Ala Gly Pro Ala Val Ala Val Val Gly Gln
            20                  25                  30

Ala Thr Gln Ile Ala Lys
        35

<210> SEQ ID NO 3
<211> LENGTH: 99
<212> TYPE: DNA
<213> ORGANISM: Artificial
<220> FEATURE:
<223> OTHER INFORMATION: DNA sequence encoding Cecropin P1 peptide

<400> SEQUENCE: 3
atgagctggc tgagcaaaac cgcgaaaaaa ctggaaaaca gcgcgaaaaa acgcattagc      60
gaaggcattg cgattgcgat tcagggcggc ccgcgctaa                             99

<210> SEQ ID NO 4
```

-continued

<211> LENGTH: 32
<212> TYPE: PRT
<213> ORGANISM: Artificial
<220> FEATURE:
<223> OTHER INFORMATION: Amino acid sequence of Cecropin P1 peptide

<400> SEQUENCE: 4

Met Ser Trp Leu Ser Lys Thr Ala Lys Lys Leu Glu Asn Ser Ala Lys
1               5                   10                  15

Lys Arg Ile Ser Glu Gly Ile Ala Ile Ala Ile Gln Gly Gly Pro Arg
            20                  25                  30

<210> SEQ ID NO 5
<211> LENGTH: 138
<212> TYPE: DNA
<213> ORGANISM: Artificial
<220> FEATURE:
<223> OTHER INFORMATION: DNA sequence encoding Opistoporin I peptide

<400> SEQUENCE: 5
atgggcaaag tgtgggattg gattaaaagc accgcgaaaa aactgtggaa cagcgaaccg      60
gtgaaagaac tgaaaaacac cgcgctgaac gcggcgaaaa acctggtggc ggaaaaaatt     120
ggcgcgaccc cgagctaa                                                   138

<210> SEQ ID NO 6
<211> LENGTH: 45
<212> TYPE: PRT
<213> ORGANISM: Artificial
<220> FEATURE:
<223> OTHER INFORMATION: Amino acid sequence of Opistoporin I peptide

<400> SEQUENCE: 6

Met Gly Lys Val Trp Asp Trp Ile Lys Ser Thr Ala Lys Lys Leu Trp
1               5                   10                  15

Asn Ser Glu Pro Val Lys Glu Leu Lys Asn Thr Ala Leu Asn Ala Ala
            20                  25                  30

Lys Asn Leu Val Ala Glu Lys Ile Gly Ala Thr Pro Ser
        35                  40                  45

<210> SEQ ID NO 7
<211> LENGTH: 235
<212> TYPE: PRT
<213> ORGANISM: E. coli

<400> SEQUENCE: 7

Met Tyr Arg Tyr Leu Ser Ile Ala Ala Val Val Leu Ser Ala Ala Phe
1               5                   10                  15

Ser Gly Pro Ala Leu Ala Glu Gly Ile Asn Ser Phe Ser Gln Ala Lys
            20                  25                  30

Ala Ala Ala Val Lys Val His Ala Asp Ala Pro Gly Thr Phe Tyr Cys
        35                  40                  45

Gly Cys Lys Ile Asn Trp Gln Gly Lys Lys Gly Val Val Asp Leu Gln
    50                  55                  60

Ser Cys Gly Tyr Gln Val Arg Lys Asn Glu Asn Arg Ala Ser Arg Val
65                  70                  75                  80

Glu Trp Glu His Val Val Pro Ala Trp Gln Phe Gly His Gln Arg Gln
                85                  90                  95

Cys Trp Gln Asp Gly Gly Arg Lys Asn Cys Ala Lys Asp Pro Val Tyr
            100                 105                 110

Arg Lys Met Glu Ser Asp Met His Asn Leu Gln Pro Ser Val Gly Glu

```
            115                 120                 125
Val Asn Gly Asp Arg Gly Asn Phe Met Tyr Ser Gln Trp Asn Gly Gly
    130                 135                 140

Glu Gly Gln Tyr Gly Gln Cys Ala Met Lys Val Asp Phe Lys Glu Lys
145                 150                 155                 160

Ala Ala Glu Pro Pro Ala Arg Ala Arg Gly Ala Ile Ala Arg Thr Tyr
                165                 170                 175

Phe Tyr Met Arg Asp Gln Tyr Asn Leu Thr Leu Ser Arg Gln Gln Thr
            180                 185                 190

Gln Leu Phe Asn Ala Trp Asn Lys Met Tyr Pro Val Thr Asp Trp Glu
        195                 200                 205

Cys Glu Arg Asp Glu Arg Ile Ala Lys Val Gln Gly Asn His Asn Pro
    210                 215                 220

Tyr Val Gln Arg Ala Cys Gln Ala Arg Lys Ser
225                 230                 235

<210> SEQ ID NO 8
<211> LENGTH: 784
<212> TYPE: PRT
<213> ORGANISM: E. coli

<400> SEQUENCE: 8

Met Asn Pro Glu Arg Ser Glu Arg Ile Glu Ile Pro Val Leu Pro Leu
1               5                   10                  15

Arg Asp Val Val Val Tyr Pro His Met Val Ile Pro Leu Phe Val Gly
                20                  25                  30

Arg Glu Lys Ser Ile Arg Cys Leu Glu Ala Ala Met Asp His Asp Lys
            35                  40                  45

Lys Ile Met Leu Val Ala Gln Lys Glu Ala Ser Thr Asp Glu Pro Gly
        50                  55                  60

Val Asn Asp Leu Phe Thr Val Gly Thr Val Ala Ser Ile Leu Gln Met
65                  70                  75                  80

Leu Lys Leu Pro Asp Gly Thr Val Lys Val Leu Val Glu Gly Leu Gln
                85                  90                  95

Arg Ala Arg Ile Ser Ala Leu Ser Asp Asn Gly Glu His Phe Ser Ala
            100                 105                 110

Lys Ala Glu Tyr Leu Glu Ser Pro Thr Ile Asp Glu Arg Glu Gln Glu
        115                 120                 125

Val Leu Val Arg Thr Ala Ile Ser Gln Phe Glu Gly Tyr Ile Lys Leu
    130                 135                 140

Asn Lys Lys Ile Pro Pro Glu Val Leu Thr Ser Leu Asn Ser Ile Asp
145                 150                 155                 160

Asp Pro Ala Arg Leu Ala Asp Thr Ile Ala Ala His Met Pro Leu Lys
                165                 170                 175

Leu Ala Asp Lys Gln Ser Val Leu Glu Met Ser Asp Val Asn Glu Arg
            180                 185                 190

Leu Glu Tyr Leu Met Ala Met Met Glu Ser Glu Ile Asp Leu Leu Gln
        195                 200                 205

Val Glu Lys Arg Ile Arg Asn Arg Val Lys Lys Gln Met Glu Lys Ser
    210                 215                 220

Gln Arg Glu Tyr Tyr Leu Asn Glu Gln Met Lys Ala Ile Gln Lys Glu
225                 230                 235                 240

Leu Gly Glu Met Asp Asp Ala Pro Asp Glu Asn Glu Ala Leu Lys Arg
                245                 250                 255
```

-continued

Lys Ile Asp Ala Ala Lys Met Pro Lys Glu Ala Lys Glu Lys Ala Glu
                    260                 265                 270

Ala Glu Leu Gln Lys Leu Lys Met Met Ser Pro Met Ser Ala Glu Ala
                275                 280                 285

Thr Val Val Arg Gly Tyr Ile Asp Trp Met Val Gln Val Pro Trp Asn
            290                 295                 300

Ala Arg Ser Lys Val Lys Lys Asp Leu Arg Gln Ala Gln Glu Ile Leu
305                 310                 315                 320

Asp Thr Asp His Tyr Gly Leu Glu Arg Val Lys Asp Arg Ile Leu Glu
                325                 330                 335

Tyr Leu Ala Val Gln Ser Arg Val Asn Lys Ile Lys Gly Pro Ile Leu
                340                 345                 350

Cys Leu Val Gly Pro Pro Gly Val Gly Lys Thr Ser Leu Gly Gln Ser
            355                 360                 365

Ile Ala Lys Ala Thr Gly Arg Lys Tyr Val Arg Met Ala Leu Gly Gly
            370                 375                 380

Val Arg Asp Glu Ala Glu Ile Arg Gly His Arg Arg Thr Tyr Ile Gly
385                 390                 395                 400

Ser Met Pro Gly Lys Leu Ile Gln Lys Met Ala Lys Val Gly Val Lys
                405                 410                 415

Asn Pro Leu Phe Leu Leu Asp Glu Ile Asp Lys Met Ser Ser Asp Met
                420                 425                 430

Arg Gly Asp Pro Ala Ser Ala Leu Leu Glu Val Leu Asp Pro Glu Gln
            435                 440                 445

Asn Val Ala Phe Ser Asp His Tyr Leu Glu Val Asp Tyr Asp Leu Ser
450                 455                 460

Asp Val Met Phe Val Ala Thr Ser Asn Ser Met Asn Ile Pro Ala Pro
465                 470                 475                 480

Leu Leu Asp Arg Met Glu Val Ile Arg Leu Ser Gly Tyr Thr Glu Asp
                485                 490                 495

Glu Lys Leu Asn Ile Ala Lys Arg His Leu Leu Pro Lys Gln Ile Glu
            500                 505                 510

Arg Asn Ala Leu Lys Lys Gly Glu Leu Thr Val Asp Asp Ser Ala Ile
            515                 520                 525

Ile Gly Ile Ile Arg Tyr Tyr Thr Arg Glu Ala Gly Val Arg Gly Leu
            530                 535                 540

Glu Arg Glu Ile Ser Lys Leu Cys Arg Lys Ala Val Lys Gln Leu Leu
545                 550                 555                 560

Leu Asp Lys Ser Leu Lys His Ile Glu Ile Asn Gly Asp Asn Leu His
                565                 570                 575

Asp Tyr Leu Gly Val Gln Arg Phe Asp Tyr Gly Arg Ala Asp Asn Glu
            580                 585                 590

Asn Arg Val Gly Gln Val Thr Gly Leu Ala Trp Thr Glu Val Gly Gly
            595                 600                 605

Asp Leu Leu Thr Ile Glu Thr Ala Cys Val Pro Gly Lys Gly Lys Leu
            610                 615                 620

Thr Tyr Thr Gly Ser Leu Gly Glu Val Met Gln Glu Ser Ile Gln Ala
625                 630                 635                 640

Ala Leu Thr Val Val Arg Ala Arg Ala Glu Lys Leu Gly Ile Asn Pro
                645                 650                 655

Asp Phe Tyr Glu Lys Arg Asp Ile His Val His Val Pro Glu Gly Ala
            660                 665                 670

Thr Pro Lys Asp Gly Pro Ser Ala Gly Ile Ala Met Cys Thr Ala Leu

```
                675                 680                 685
Val Ser Cys Leu Thr Gly Asn Pro Val Arg Ala Asp Val Ala Met Thr
690                 695                 700
Gly Glu Ile Thr Leu Arg Gly Gln Val Leu Pro Ile Gly Gly Leu Lys
705                 710                 715                 720
Glu Lys Leu Leu Ala Ala His Arg Gly Gly Ile Lys Thr Val Leu Ile
                725                 730                 735
Pro Phe Glu Asn Lys Arg Asp Leu Glu Glu Ile Pro Asp Asn Val Ile
                740                 745                 750
Ala Asp Leu Asp Ile His Pro Val Lys Arg Ile Glu Glu Val Leu Thr
                755                 760                 765
Leu Ala Leu Gln Asn Glu Pro Ser Gly Met Gln Val Val Thr Ala Lys
                770                 775                 780

<210> SEQ ID NO 9
<211> LENGTH: 111
<212> TYPE: PRT
<213> ORGANISM: E. coli

<400> SEQUENCE: 9

Met Val Ser Arg Tyr Val Pro Asp Met Gly Asp Leu Ile Trp Val Asp
1               5                   10                  15
Phe Asp Pro Thr Lys Gly Ser Glu Gln Ala Gly His Arg Pro Ala Val
                20                  25                  30
Val Leu Ser Pro Phe Met Tyr Asn Asn Lys Thr Gly Met Cys Leu Cys
            35                  40                  45
Val Pro Cys Thr Thr Gln Ser Lys Gly Tyr Pro Phe Glu Val Val Leu
        50                  55                  60
Ser Gly Gln Glu Arg Asp Gly Val Ala Leu Ala Asp Gln Val Lys Ser
65                  70                  75                  80
Ile Ala Trp Arg Ala Arg Gly Ala Thr Lys Lys Gly Thr Val Ala Pro
                85                  90                  95
Glu Glu Leu Gln Leu Ile Lys Ala Lys Ile Asn Val Leu Ile Gly
                100                 105                 110

<210> SEQ ID NO 10
<211> LENGTH: 317
<212> TYPE: PRT
<213> ORGANISM: E. coli

<400> SEQUENCE: 10

Met Arg Ala Lys Leu Leu Gly Ile Val Leu Thr Thr Pro Ile Ala Ile
1               5                   10                  15
Ser Ser Phe Ala Ser Thr Glu Thr Leu Ser Phe Thr Pro Asp Asn Ile
                20                  25                  30
Asn Ala Asp Ile Ser Leu Gly Thr Leu Ser Gly Lys Thr Lys Glu Arg
            35                  40                  45
Val Tyr Leu Ala Glu Glu Gly Gly Arg Lys Val Ser Gln Leu Asp Trp
        50                  55                  60
Lys Phe Asn Asn Ala Ala Ile Ile Lys Gly Ala Ile Asn Trp Asp Leu
65                  70                  75                  80
Met Pro Gln Ile Ser Ile Gly Ala Ala Gly Trp Thr Thr Leu Gly Ser
                85                  90                  95
Arg Gly Gly Asn Met Val Asp Gln Asp Trp Met Asp Ser Ser Asn Pro
                100                 105                 110
Gly Thr Trp Thr Asp Glu Ser Arg His Pro Asp Thr Gln Leu Asn Tyr
```

```
            115                 120                 125
Ala Asn Glu Phe Asp Leu Asn Ile Lys Gly Trp Leu Leu Asn Glu Pro
            130                 135                 140

Asn Tyr Arg Leu Gly Leu Met Ala Gly Tyr Gln Glu Ser Arg Tyr Ser
145                 150                 155                 160

Phe Thr Ala Arg Gly Gly Ser Tyr Ile Tyr Ser Ser Glu Glu Gly Phe
                165                 170                 175

Arg Asp Asp Ile Gly Ser Phe Pro Asn Gly Glu Arg Ala Ile Gly Tyr
            180                 185                 190

Lys Gln Arg Phe Lys Met Pro Tyr Ile Gly Leu Thr Gly Ser Tyr Arg
            195                 200                 205

Tyr Glu Asp Phe Glu Leu Gly Gly Thr Phe Lys Tyr Ser Gly Trp Val
            210                 215                 220

Glu Ser Ser Asp Asn Asp Glu His Tyr Asp Pro Gly Lys Arg Ile Thr
225                 230                 235                 240

Tyr Arg Ser Lys Val Lys Asp Gln Asn Tyr Tyr Ser Val Ala Val Asn
                245                 250                 255

Ala Gly Tyr Tyr Val Thr Pro Asn Ala Lys Val Tyr Val Glu Gly Ala
            260                 265                 270

Trp Asn Arg Val Thr Asn Lys Lys Gly Asn Thr Ser Leu Tyr Asp His
            275                 280                 285

Asn Asn Asn Thr Ser Asp Tyr Ser Lys Asn Gly Ala Gly Ile Glu Asn
290                 295                 300

Tyr Asn Phe Ile Thr Thr Ala Gly Leu Lys Tyr Thr Phe
305                 310                 315

<210> SEQ ID NO 11
<211> LENGTH: 268
<212> TYPE: PRT
<213> ORGANISM: E. coli

<400> SEQUENCE: 11

Met Lys Ala Phe Trp Arg Asn Ala Ala Leu Leu Ala Val Ser Leu Leu
1               5                   10                  15

Pro Phe Ser Ser Ala Asn Ala Leu Ala Leu Gln Ala Lys Gln Tyr Gly
                20                  25                  30

Asp Phe Asp Arg Tyr Val Leu Ala Leu Ser Trp Gln Thr Gly Phe Cys
            35                  40                  45

Gln Ser Gln His Asp Arg Asn Arg Asn Glu Arg Asp Glu Cys Arg Leu
        50                  55                  60

Gln Thr Glu Thr Thr Asn Lys Ala Asp Phe Leu Thr Val His Gly Leu
65                  70                  75                  80

Trp Pro Gly Leu Pro Lys Ser Val Ala Ala Arg Gly Val Asp Glu Arg
                85                  90                  95

Arg Trp Met Arg Phe Gly Cys Ala Thr Arg Pro Ile Pro Asn Leu Pro
            100                 105                 110

Glu Ala Arg Ala Ser Arg Met Cys Ser Ser Pro Glu Thr Gly Leu Ser
            115                 120                 125

Leu Glu Thr Ala Ala Lys Leu Ser Glu Val Met Pro Gly Ala Gly Gly
            130                 135                 140

Arg Ser Cys Leu Glu Arg Tyr Glu Tyr Ala Lys His Gly Ala Cys Phe
145                 150                 155                 160

Gly Phe Asp Pro Asp Ala Tyr Phe Gly Thr Met Val Arg Leu Asn Gln
                165                 170                 175
```

```
Glu Ile Lys Glu Ser Glu Ala Gly Lys Phe Leu Ala Asp Asn Tyr Gly
                180                 185                 190

Lys Thr Val Ser Arg Arg Asp Phe Asp Ala Ala Phe Ala Lys Ser Trp
            195                 200                 205

Gly Lys Glu Asn Val Lys Ala Val Lys Leu Thr Cys Gln Gly Asn Pro
        210                 215                 220

Ala Tyr Leu Thr Glu Ile Gln Ile Ser Ile Lys Ala Asp Ala Ile Asn
225                 230                 235                 240

Ala Pro Leu Ser Ala Asn Ser Phe Leu Pro Gln Pro His Pro Gly Asn
                245                 250                 255

Cys Gly Lys Thr Phe Val Ile Asp Lys Ala Gly Tyr
                260                 265

<210> SEQ ID NO 12
<211> LENGTH: 644
<212> TYPE: PRT
<213> ORGANISM: E. coli

<400> SEQUENCE: 12

Met Phe Gln Asp Asn Pro Leu Leu Ala Gln Leu Lys Gln Gln Leu His
1               5                   10                  15

Ser Gln Thr Pro Arg Ala Glu Gly Val Val Lys Ala Thr Glu Lys Gly
            20                  25                  30

Phe Gly Phe Leu Glu Val Asp Ala Gln Lys Ser Tyr Phe Ile Pro Pro
        35                  40                  45

Pro Gln Met Lys Lys Val Met His Gly Asp Arg Ile Ile Ala Val Ile
    50                  55                  60

His Ser Glu Lys Glu Arg Glu Ser Ala Glu Pro Glu Glu Leu Val Glu
65              70                  75                  80

Pro Phe Leu Thr Arg Phe Val Gly Lys Val Gln Gly Lys Asn Asp Arg
                85                  90                  95

Leu Ala Ile Val Pro Asp His Pro Leu Leu Lys Asp Ala Ile Pro Cys
            100                 105                 110

Arg Ala Ala Arg Gly Leu Asn His Glu Phe Lys Glu Gly Asp Trp Ala
        115                 120                 125

Val Ala Glu Met Arg Arg His Pro Leu Lys Gly Asp Arg Ser Phe Tyr
    130                 135                 140

Ala Glu Leu Thr Gln Tyr Ile Thr Phe Gly Asp Asp His Phe Val Pro
145                 150                 155                 160

Trp Trp Val Thr Leu Ala Arg His Asn Leu Glu Lys Glu Ala Pro Asp
                165                 170                 175

Gly Val Ala Thr Glu Met Leu Asp Glu Gly Leu Val Arg Glu Asp Leu
            180                 185                 190

Thr Ala Leu Asp Phe Val Thr Ile Asp Ser Ala Ser Thr Glu Asp Met
        195                 200                 205

Asp Asp Ala Leu Phe Ala Lys Ala Leu Pro Asp Asp Lys Leu Gln Leu
    210                 215                 220

Ile Val Ala Ile Ala Asp Pro Thr Ala Trp Ile Ala Glu Gly Ser Lys
225                 230                 235                 240

Leu Asp Lys Ala Ala Lys Ile Arg Ala Phe Thr Asn Tyr Leu Pro Gly
                245                 250                 255

Phe Asn Ile Pro Met Leu Pro Arg Glu Leu Ser Asp Asp Leu Cys Ser
                260                 265                 270

Leu Arg Ala Asn Glu Val Arg Pro Val Leu Ala Cys Arg Met Thr Leu
            275                 280                 285
```

Ser Ala Asp Gly Thr Ile Glu Asp Asn Ile Glu Phe Phe Ala Ala Thr
290                 295                 300

Ile Glu Ser Lys Ala Lys Leu Val Tyr Asp Gln Val Ser Asp Trp Leu
305                 310                 315                 320

Glu Asn Thr Gly Asp Trp Gln Pro Ser Glu Ala Ile Ala Glu Gln
            325                 330                 335

Val Arg Leu Leu Ala Gln Ile Cys Gln Arg Arg Gly Glu Trp Arg His
            340                 345                 350

Asn His Ala Leu Val Phe Lys Asp Arg Pro Asp Tyr Arg Phe Ile Leu
            355                 360                 365

Gly Glu Lys Gly Glu Val Leu Asp Ile Val Ala Glu Pro Arg Arg Ile
370                 375                 380

Ala Asn Arg Ile Val Glu Glu Ala Met Ile Ala Asn Ile Cys Ala
385                 390                 395                 400

Ala Arg Val Leu Arg Asp Lys Leu Gly Phe Gly Ile Tyr Asn Val His
            405                 410                 415

Met Gly Phe Asp Pro Ala Asn Ala Asp Ala Leu Ala Ala Leu Leu Lys
            420                 425                 430

Thr His Gly Leu His Val Asp Ala Glu Glu Val Leu Thr Leu Asp Gly
            435                 440                 445

Phe Cys Lys Leu Arg Arg Glu Leu Asp Ala Gln Pro Thr Gly Phe Leu
450                 455                 460

Asp Ser Arg Ile Arg Arg Phe Gln Ser Phe Ala Glu Ile Ser Thr Glu
465                 470                 475                 480

Pro Gly Pro His Phe Gly Leu Gly Leu Glu Ala Tyr Ala Thr Trp Thr
            485                 490                 495

Ser Pro Ile Arg Lys Tyr Gly Asp Met Ile Asn His Arg Leu Leu Lys
            500                 505                 510

Ala Val Ile Lys Gly Glu Thr Ala Thr Arg Pro Gln Asp Glu Ile Thr
            515                 520                 525

Val Gln Met Ala Glu Arg Arg Arg Leu Asn Arg Met Ala Glu Arg Asp
530                 535                 540

Val Gly Asp Trp Leu Tyr Ala Arg Phe Leu Lys Asp Lys Ala Gly Thr
545                 550                 555                 560

Asp Thr Arg Phe Ala Ala Glu Ile Val Asp Ile Ser Arg Gly Gly Met
            565                 570                 575

Arg Val Arg Leu Val Asp Asn Gly Ala Ile Ala Phe Ile Pro Ala Pro
            580                 585                 590

Phe Leu His Ala Val Arg Asp Glu Leu Val Cys Ser Gln Glu Asn Gly
            595                 600                 605

Thr Val Gln Ile Lys Gly Glu Thr Val Tyr Lys Val Thr Asp Val Ile
            610                 615                 620

Asp Val Thr Ile Ala Glu Val Arg Met Glu Thr Arg Ser Ile Ile Ala
625                 630                 635                 640

Arg Pro Val Ala

<210> SEQ ID NO 13
<211> LENGTH: 502
<212> TYPE: PRT
<213> ORGANISM: E. coli

<400> SEQUENCE: 13

Met Thr Glu Lys Lys Tyr Ile Val Ala Leu Asp Gln Gly Thr Thr Ser
1               5                   10                  15

Ser Arg Ala Val Val Met Asp His Asp Ala Asn Ile Ile Ser Val Ser
            20                  25                  30

Gln Arg Glu Phe Glu Gln Ile Tyr Pro Lys Pro Gly Trp Val Glu His
        35                  40                  45

Asp Pro Met Glu Ile Trp Ala Thr Gln Ser Ser Thr Leu Val Glu Val
50                  55                  60

Leu Ala Lys Ala Asp Ile Ser Ser Asp Gln Ile Ala Ala Ile Gly Ile
65                  70                  75                  80

Thr Asn Gln Arg Glu Thr Thr Ile Val Trp Glu Lys Glu Thr Gly Lys
                85                  90                  95

Pro Ile Tyr Asn Ala Ile Val Trp Gln Cys Arg Arg Thr Ala Glu Ile
            100                 105                 110

Cys Glu His Leu Lys Arg Asp Gly Leu Glu Asp Tyr Ile Arg Ser Asn
        115                 120                 125

Thr Gly Leu Val Ile Asp Pro Tyr Phe Ser Gly Thr Lys Val Lys Trp
    130                 135                 140

Ile Leu Asp His Val Glu Gly Ser Arg Glu Arg Ala Arg Arg Gly Glu
145                 150                 155                 160

Leu Leu Phe Gly Thr Val Asp Thr Trp Leu Ile Trp Lys Met Thr Gln
                165                 170                 175

Gly Arg Val His Val Thr Asp Tyr Thr Asn Ala Ser Arg Thr Met Leu
            180                 185                 190

Phe Asn Ile His Thr Leu Asp Trp Asp Asp Lys Met Leu Glu Val Leu
        195                 200                 205

Asp Ile Pro Arg Glu Met Leu Pro Glu Val Arg Arg Ser Ser Glu Val
    210                 215                 220

Tyr Gly Gln Thr Asn Ile Gly Gly Lys Gly Gly Thr Arg Ile Pro Ile
225                 230                 235                 240

Ser Gly Ile Ala Gly Asp Gln Gln Ala Ala Leu Phe Gly Gln Leu Cys
                245                 250                 255

Val Lys Glu Gly Met Ala Lys Asn Thr Tyr Gly Thr Gly Cys Phe Met
            260                 265                 270

Leu Met Asn Thr Gly Glu Lys Ala Val Lys Ser Glu Asn Gly Leu Leu
        275                 280                 285

Thr Thr Ile Ala Cys Gly Pro Thr Gly Glu Val Asn Tyr Ala Leu Glu
    290                 295                 300

Gly Ala Val Phe Met Ala Gly Ala Ser Ile Gln Trp Leu Arg Asp Glu
305                 310                 315                 320

Met Lys Leu Ile Asn Asp Ala Tyr Asp Ser Glu Tyr Phe Ala Thr Lys
                325                 330                 335

Val Gln Asn Thr Asn Gly Val Tyr Val Val Pro Ala Phe Thr Gly Leu
            340                 345                 350

Gly Ala Pro Tyr Trp Asp Pro Tyr Ala Arg Gly Ala Ile Phe Gly Leu
        355                 360                 365

Thr Arg Gly Val Asn Ala Asn His Ile Ile Arg Ala Thr Leu Glu Ser
    370                 375                 380

Ile Ala Tyr Gln Thr Arg Asp Val Leu Glu Ala Met Gln Ala Asp Ser
385                 390                 395                 400

Gly Ile Arg Leu His Ala Leu Arg Val Asp Gly Gly Ala Val Ala Asn
                405                 410                 415

Asn Phe Leu Met Gln Phe Gln Ser Asp Ile Leu Gly Thr Arg Val Glu
            420                 425                 430

```
Arg Pro Glu Val Arg Glu Val Thr Ala Leu Gly Ala Ala Tyr Leu Ala
        435                 440                 445

Gly Leu Ala Val Gly Phe Trp Gln Asn Leu Asp Glu Leu Gln Glu Lys
450                 455                 460

Ala Val Ile Glu Arg Glu Phe Arg Pro Gly Ile Glu Thr Thr Glu Arg
465                 470                 475                 480

Asn Tyr Arg Tyr Ala Gly Trp Lys Lys Ala Val Lys Arg Ala Met Ala
                485                 490                 495

Trp Glu Glu His Asp Glu
                500

<210> SEQ ID NO 14
<211> LENGTH: 450
<212> TYPE: PRT
<213> ORGANISM: E. coli

<400> SEQUENCE: 14

Met Thr Lys His Tyr Asp Tyr Ile Ala Ile Gly Gly Ser Gly Gly
1               5                   10                  15

Ile Ala Ser Ile Asn Arg Ala Ala Met Tyr Gly Gln Lys Cys Ala Leu
            20                  25                  30

Ile Glu Ala Lys Glu Leu Gly Gly Thr Cys Val Asn Val Gly Cys Val
        35                  40                  45

Pro Lys Lys Val Met Trp His Ala Ala Gln Ile Arg Glu Ala Ile His
50                  55                  60

Met Tyr Gly Pro Asp Tyr Gly Phe Asp Thr Thr Ile Asn Lys Phe Asn
65                  70                  75                  80

Trp Glu Thr Leu Ile Ala Ser Arg Thr Ala Tyr Ile Asp Arg Ile His
                85                  90                  95

Thr Ser Tyr Glu Asn Val Leu Gly Lys Asn Asn Val Asp Val Ile Lys
            100                 105                 110

Gly Phe Ala Arg Phe Val Asp Ala Lys Thr Leu Glu Val Asn Gly Glu
        115                 120                 125

Thr Ile Thr Ala Asp His Ile Leu Ile Ala Thr Gly Gly Arg Pro Ser
130                 135                 140

His Pro Asp Ile Pro Gly Val Glu Tyr Gly Ile Asp Ser Asp Gly Phe
145                 150                 155                 160

Phe Ala Leu Pro Ala Leu Pro Glu Arg Val Ala Val Val Gly Ala Gly
                165                 170                 175

Tyr Ile Ala Val Glu Leu Ala Gly Val Ile Asn Gly Leu Gly Ala Lys
            180                 185                 190

Thr His Leu Phe Val Arg Lys His Ala Pro Leu Arg Ser Phe Asp Pro
        195                 200                 205

Met Ile Ser Glu Thr Leu Val Glu Val Met Asn Ala Glu Gly Pro Gln
210                 215                 220

Leu His Thr Asn Ala Ile Pro Lys Ala Val Val Lys Asn Thr Asp Gly
225                 230                 235                 240

Ser Leu Thr Leu Glu Leu Glu Asp Gly Arg Ser Glu Thr Val Asp Cys
                245                 250                 255

Leu Ile Trp Ala Ile Gly Arg Glu Pro Ala Asn Asp Asn Ile Asn Leu
            260                 265                 270

Glu Ala Ala Gly Val Lys Thr Asn Glu Lys Gly Tyr Ile Val Val Asp
        275                 280                 285

Lys Tyr Gln Asn Thr Asn Ile Glu Gly Ile Tyr Ala Val Gly Asp Asn
290                 295                 300
```

Thr Gly Ala Val Glu Leu Thr Pro Val Ala Val Ala Ala Gly Arg Arg
305                 310                 315                 320

Leu Ser Glu Arg Leu Phe Asn Asn Lys Pro Asp Glu His Leu Asp Tyr
            325                 330                 335

Ser Asn Ile Pro Thr Val Val Phe Ser His Pro Pro Ile Gly Thr Val
            340                 345                 350

Gly Leu Thr Glu Pro Gln Ala Arg Glu Gln Tyr Gly Asp Asp Gln Val
            355                 360                 365

Lys Val Tyr Lys Ser Ser Phe Thr Ala Met Tyr Thr Ala Val Thr Thr
            370                 375                 380

His Arg Gln Pro Cys Arg Met Lys Leu Val Cys Val Gly Ser Glu Glu
385                 390                 395                 400

Lys Ile Val Gly Ile His Gly Ile Gly Phe Gly Met Asp Glu Met Leu
                405                 410                 415

Gln Gly Phe Ala Val Ala Leu Lys Met Gly Ala Thr Lys Lys Asp Phe
            420                 425                 430

Asp Asn Thr Val Ala Ile His Pro Thr Ala Ala Glu Glu Phe Val Thr
            435                 440                 445

Met Arg
    450

<210> SEQ ID NO 15
<211> LENGTH: 518
<212> TYPE: PRT
<213> ORGANISM: E. coli

<400> SEQUENCE: 15

Met Ile Pro Asp Val Ser Gln Ala Leu Ala Trp Leu Glu Lys His Pro
1               5                   10                  15

Gln Ala Leu Lys Gly Ile Gln Arg Gly Leu Glu Arg Glu Thr Leu Arg
            20                  25                  30

Val Asn Ala Asp Gly Thr Leu Ala Thr Thr Gly His Pro Glu Ala Leu
        35                  40                  45

Gly Ser Ala Leu Thr His Lys Trp Ile Thr Thr Asp Phe Ala Glu Ala
50                  55                  60

Leu Leu Glu Phe Ile Thr Pro Val Asp Gly Asp Ile Glu His Met Leu
65                  70                  75                  80

Thr Phe Met Arg Asp Leu His Arg Tyr Thr Ala Arg Asn Met Gly Asp
                85                  90                  95

Glu Arg Met Trp Pro Leu Ser Met Pro Cys Tyr Ile Ala Glu Gly Gln
            100                 105                 110

Asp Ile Glu Leu Ala Gln Tyr Gly Thr Ser Asn Thr Gly Arg Phe Lys
        115                 120                 125

Thr Leu Tyr Arg Glu Gly Leu Lys Asn Arg Tyr Gly Ala Leu Met Gln
130                 135                 140

Thr Ile Ser Gly Val His Tyr Asn Phe Ser Leu Pro Met Ala Phe Trp
145                 150                 155                 160

Gln Ala Lys Cys Gly Asp Ile Ser Gly Ala Asp Ala Lys Glu Lys Ile
                165                 170                 175

Ser Ala Gly Tyr Phe Arg Val Ile Arg Asn Tyr Tyr Arg Phe Gly Trp
            180                 185                 190

Val Ile Pro Tyr Leu Phe Gly Ala Ser Pro Ala Ile Cys Ser Ser Phe
        195                 200                 205

Leu Gln Gly Lys Pro Thr Ser Leu Pro Phe Glu Lys Thr Glu Cys Gly

```
                   210                 215                 220
Met Tyr Tyr Leu Pro Tyr Ala Thr Ser Leu Arg Leu Ser Asp Leu Gly
225                 230                 235                 240

Tyr Thr Asn Lys Ser Gln Ser Asn Leu Gly Ile Thr Phe Asn Asp Leu
                245                 250                 255

Tyr Glu Tyr Val Ala Gly Leu Lys Gln Ala Ile Lys Thr Pro Ser Glu
                    260                 265                 270

Glu Tyr Ala Lys Ile Gly Ile Glu Lys Asp Gly Lys Arg Leu Gln Ile
                275                 280                 285

Asn Ser Asn Val Leu Gln Ile Glu Asn Glu Leu Tyr Ala Pro Ile Arg
290                 295                 300

Pro Lys Arg Val Thr Arg Ser Gly Glu Ser Pro Ser Asp Ala Leu Leu
305                 310                 315                 320

Arg Gly Gly Ile Glu Tyr Ile Glu Val Arg Ser Leu Asp Ile Asn Pro
                    325                 330                 335

Phe Ser Pro Ile Gly Val Asp Glu Gln Val Arg Phe Leu Asp Leu
                340                 345                 350

Phe Met Val Trp Cys Ala Leu Ala Asp Ala Pro Glu Met Ser Ser Ser
            355                 360                 365

Glu Leu Ala Cys Thr Arg Val Asn Trp Asn Arg Val Ile Leu Glu Gly
        370                 375                 380

Arg Lys Pro Gly Leu Thr Leu Gly Ile Gly Cys Glu Thr Ala Gln Phe
385                 390                 395                 400

Pro Leu Pro Gln Val Gly Lys Asp Leu Phe Arg Asp Leu Lys Arg Val
                405                 410                 415

Ala Gln Thr Leu Asp Ser Ile Asn Gly Gly Glu Ala Tyr Gln Lys Val
                420                 425                 430

Cys Asp Glu Leu Val Ala Cys Phe Asp Asn Pro Asp Leu Thr Phe Ser
                435                 440                 445

Ala Arg Ile Leu Arg Ser Met Ile Asp Thr Gly Ile Gly Gly Thr Gly
                450                 455                 460

Lys Ala Phe Ala Glu Ala Tyr Arg Asn Leu Leu Arg Glu Glu Pro Leu
465                 470                 475                 480

Glu Ile Leu Arg Glu Glu Asp Phe Val Ala Glu Arg Glu Ala Ser Glu
                485                 490                 495

Arg Arg Gln Gln Glu Met Glu Ala Ala Asp Thr Glu Pro Phe Ala Val
                500                 505                 510

Trp Leu Glu Lys His Ala
            515

<210> SEQ ID NO 16
<211> LENGTH: 471
<212> TYPE: PRT
<213> ORGANISM: E. coli

<400> SEQUENCE: 16

Met Glu Asn Phe Lys His Leu Pro Glu Pro Phe Arg Ile Arg Val Ile
1               5                   10                  15

Glu Pro Val Lys Arg Thr Thr Arg Ala Tyr Arg Glu Glu Ala Ile Ile
                20                  25                  30

Lys Ser Gly Met Asn Pro Phe Leu Leu Asp Ser Glu Asp Val Phe Ile
            35                  40                  45

Asp Leu Leu Thr Asp Ser Gly Thr Gly Ala Val Thr Gln Ser Met Gln
        50                  55                  60
```

```
Ala Ala Met Met Arg Gly Asp Glu Ala Tyr Ser Gly Ser Arg Ser Tyr
 65                  70                  75                  80

Tyr Ala Leu Ala Glu Ser Val Lys Asn Ile Phe Gly Tyr Gln Tyr Thr
                 85                  90                  95

Ile Pro Thr His Gln Gly Arg Gly Ala Glu Gln Ile Tyr Ile Pro Val
            100                 105                 110

Leu Ile Lys Lys Arg Glu Gln Glu Lys Gly Leu Asp Arg Ser Lys Met
            115                 120                 125

Val Ala Phe Ser Asn Tyr Phe Phe Asp Thr Thr Gln Gly His Ser Gln
130                 135                 140

Ile Asn Gly Cys Thr Val Arg Asn Val Tyr Ile Lys Glu Ala Phe Asp
145                 150                 155                 160

Thr Gly Val Arg Tyr Asp Phe Lys Gly Asn Phe Asp Leu Glu Gly Leu
                165                 170                 175

Glu Arg Gly Ile Glu Glu Val Gly Pro Asn Asn Val Pro Tyr Ile Val
                180                 185                 190

Ala Thr Ile Thr Ser Asn Ser Ala Gly Gly Gln Pro Val Ser Leu Ala
                195                 200                 205

Asn Leu Lys Ala Met Tyr Ser Ile Ala Lys Lys Tyr Asp Ile Pro Val
210                 215                 220

Val Met Asp Ser Ala Arg Phe Ala Glu Asn Ala Tyr Phe Ile Lys Gln
225                 230                 235                 240

Arg Glu Ala Glu Tyr Lys Asp Trp Thr Ile Glu Gln Ile Thr Arg Glu
                245                 250                 255

Thr Tyr Lys Tyr Ala Asp Met Leu Ala Met Ser Ala Lys Lys Asp Ala
                260                 265                 270

Met Val Pro Met Gly Gly Leu Leu Cys Met Lys Asp Asp Ser Phe Phe
            275                 280                 285

Asp Val Tyr Thr Glu Cys Arg Thr Leu Cys Val Val Gln Glu Gly Phe
            290                 295                 300

Pro Thr Tyr Gly Gly Leu Glu Gly Gly Ala Met Glu Arg Leu Ala Val
305                 310                 315                 320

Gly Leu Tyr Asp Gly Met Asn Leu Asp Trp Leu Ala Tyr Arg Ile Ala
                325                 330                 335

Gln Val Gln Tyr Leu Val Asp Gly Leu Glu Glu Ile Gly Val Val Cys
                340                 345                 350

Gln Gln Ala Gly Gly His Ala Ala Phe Val Asp Ala Gly Lys Leu Leu
                355                 360                 365

Pro His Ile Pro Ala Asp Gln Phe Pro Ala Gln Ala Leu Ala Cys Glu
            370                 375                 380

Leu Tyr Lys Val Ala Gly Ile Arg Ala Val Glu Ile Gly Ser Phe Leu
385                 390                 395                 400

Leu Gly Arg Asp Pro Lys Thr Gly Lys Gln Leu Pro Cys Pro Ala Glu
                405                 410                 415

Leu Leu Arg Leu Thr Ile Pro Arg Ala Thr Tyr Thr Gln Thr His Met
                420                 425                 430

Asp Phe Ile Ile Glu Ala Phe Lys His Val Lys Glu Asn Ala Ala Asn
            435                 440                 445

Ile Lys Gly Leu Thr Phe Thr Tyr Glu Pro Lys Val Leu Arg His Phe
            450                 455                 460

Thr Ala Lys Leu Lys Glu Val
465                 470
```

<210> SEQ ID NO 17
<211> LENGTH: 696
<212> TYPE: DNA
<213> ORGANISM: V. natriegens

<400> SEQUENCE: 17

```
atgaaatacc tgttctcttt attcattctt gcactatcca gtgccgccgt ggccgcgcca      60
ccaagttcat tttcagccgc taagcgcgaa gcggtaaaaa tctatcaaga tcatcccacc     120
agcttttatt gcggctgtga tattcaatgg caaggcaaga aaggcttacc tgatctttcc     180
tcttgtggtt accaggttcg caaacaagaa aagcgtgctt cacgcatcga gtgggaacat     240
gtcgttccag cttggcaatt tgggcaccag ctgcaatgct ggcaaagcgg tggtcgtaaa     300
aactgctcgc gtaatgacaa acattccgc tcaatggaag ccgatctgca aacctgact      360
cctgcgattg gtgaggtaaa tggtgatcgc tctaactaca atttcagtca gtggaatggg     420
atcgatggcg caacctatgg tcgttgtgaa gtccaggtaa acttcaagca acgcaaagtc     480
atgccacccg atcgagcacg cggctccatc gctcgtacct atctttatat gagcaaggag     540
tacggcttca aactgtccaa gcaacaaact cagttaatga gtgcatggaa caaaacctac     600
ccagccgata atgggaatg cgaacgcgat aagcgcattg ccaaagtaca aggcaaccat     660
aatccattcg ttcaagaggc ctgtcgcgca ctgtaa                             696
```

<210> SEQ ID NO 18
<211> LENGTH: 2352
<212> TYPE: DNA
<213> ORGANISM: V. natriegens

<400> SEQUENCE: 18

```
atgaacttgg aacgttccga gagtatcgag atcccggtac tacctctacg tgacgtagtg      60
gtctacccgc acatggtcat tccattgttt gttggtcgtg aaaaatcgat tagctgtcta     120
gaaacggcga tggaaacaaa caaacaagtt ctgcttgtgg cacaaaagca agcggataca     180
gacgagccaa cggttgacga cctatttgag gtaggtacgg tagccaccat tcttcagctt     240
ttaaagcttc ctgatggcac agtaaaagta ctggttgaag gtcagcagcg tgcgaagatt     300
aatcacttta agagagcga ttttttctta gctgaagctg aattcatcgt gacacctgag     360
ctggatgagc gtgagcaaga agttattgtt cgtagtgcga tcaaccagtt cgaaggcttt     420
atcaagctga acaaaaaaat cccaccagaa gttctgactt cgctaaatgg gattgatgaa     480
gccgcgcgtc tagccgatac catcgcagct cacatgcctt tgaaattggt cgacaagcaa     540
caagtacttg agatcataga cgttaccgag cgtttggaat tcctgatggg ccaaatggag     600
tcggaaatcg atctgctgca agttgaaaaa cgcatccgtg ccgcgttaa aaagcaaatg     660
gagaagtctc agcgcgagta ctatctgaat gagcaaatga agcgattca gaaagagcta     720
ggtgagatgg aagatgcgcc ggatgaattt gaaacgctgc agaataaaat cgaagagtcc     780
aaaatgcctc aagaggcgcg cgaaaagaca gagcaagagc tacaaaagct taagatgatg     840
tctccaatgt ctgcggaagc aacagtggtg cgtagctaca tcgattggat ggtgagcgtt     900
ccttgggcta agcgttctaa agtgaaaaag aacctggcta aggcagaaga gattctaaac     960
gaagatcatt acggtctgga gcgcgtcaaa gagcgcattc tggaatactt ggcagtacaa    1020
aaccgtatta caagctgaa aggcccaatc ctttgtcttg ttggtcctcc aggtgtgggt    1080
aaaacctctc ttggccgttc gatcgcatct gcgactgggc gtaaatacgt gcgtatggcg    1140
cttggtggtg tgcgtgacga agctgagatt cgtggccacc gtcgtactta cattggctca    1200
```

```
ctaccgggta agcttatcca gaaaatgtct aaagttgggg ttaaaaaccc gctattcctt    1260
cttgatgaga tcgataagat gtcttctgac atgcgcggtg atccagcatc tgcactgcta    1320
gaagttctgg atcctgaaca aaacaactcg ttcaacgatc actacttaga agtagattac    1380
gatctgtcgg atgtaatgtt cgttgcgacg tctaactcga tgaatatccc aggtccgctt    1440
cttgaccgta tggaagttat ccgtctttct ggttacacag aagatgaaaa actgaacatc    1500
gcgaaacgcc acttggtaga taagcagttg aagcgtaacg gactgaagcc aaacgagatt    1560
gttatcgagg actcagcgat tgtcggcatt attcgttact acactcgtga agcgggtgta    1620
cgtaacctag agcgtgaaat ttctaagatc tgtcgtaagg cggtgaagaa tatcctgctg    1680
gataaagata tcaagtctgt gaccgtatct atggacaacc tgaaagagta cctgggtgtt    1740
cagcgttttg actatggtaa agctgatgaa agcaaccgta ttggtcaggt gacgggtttg    1800
gcttggactg aagtcggtgg tgatttgcta actattgaaa ctcagtctat gccgggtaaa    1860
ggtaaactga cacagacggg gtctcttggc gacgtgatgc aagagtctat ccaagcggcc    1920
atgacagttg ttcgctctcg tgctgaaaag ctgggtatca caccgatttt ctacgagaag    1980
aaagacatcc acgtgcatgt tcctgaaggt gcgacaccaa agatgggccc aagtgctggt    2040
acagcaatgt gcactgcttt ggtttctgcg ttaactggta acccagtgaa agcggaagtg    2100
gcaatgacgg gtgaaatcac actacgtggt gaagttttgc ctatcggtgg cctaaaagaa    2160
aaattacttg cggcacatcg tggcggcatt aaaacgtac tgattccaaa agataacgag    2220
cgtgatttgg aagagattcc agagaatgtt atcgcagatc tgacagttat cccggttcag    2280
tggattgatg aagtactgaa agttgcactc gagcgagacc cgacgggcgt tgagtttgaa    2340
gctaaaaaat ag                                                         2352
```

<210> SEQ ID NO 19
<211> LENGTH: 2001
<212> TYPE: DNA
<213> ORGANISM: V. natriegens

<400> SEQUENCE: 19

```
atgtttcaag ataacccgct attagcccaa cttaagcagc aaatccaaga aaaccttcct      60
aaaaagaag ggtcaatcaa agcaacagat aaaggctttg gtttccttga agtggacagc      120
aaaaccagtt tcttcattcc acctgcgtac atgaaaaagt gcattcatgg cgataaagta      180
gtcgccatta ttcgtacaga gaatgaacgt gaagttgcag agccacaaga gctgctagaa      240
cagtcactta ctcgctttat tggccgtgta aaaatgttca aggtaagct gaatgttgtt      300
cctgaccacc ctcaactgaa aaagttgtcg ctaaaagcaa aactaaagaa aggccaaaag      360
ccagataact tcaatgaagg tgattgggtt gtcggccatc ttattcgcca ccctcttaaa      420
ggtgacaact cttttcttcgt agaaatctct gaaaaaatca cggatgctga cgataagatc      480
gcaccatggt gggtaaccct tggcacaaaac gatcttccaa actctgagcc tgctggtatt      540
gagaactggg agttaaaaga cgacgcggaa ttagaccgcg ttgatttaac tcacgttcca      600
ttcgtaacta tcgatggcga gtccaccaaa gatatggacg atgcgctgca tgcgaagaaa      660
acagaatctg gcgattttga actgaccatc gcgattgccg atcctaccgc atacattacg      720
ccagaagatg aaatggacaa agtcgctcgt gagcgtggct acacgatcta cttgccaggg      780
cgcaacatcc caatgctgcc tcgcgatctt gctgatgacc tatgttctct tattgaaggt      840
gaaactcgcc ctgcccttg ctgtaccgta agcgtaagta aagatggtgt gattggtgat      900
aacatcaact tctttgctgc gaacattaag tctcacgctc gtcttgctta tgaccacgta      960
```

```
tcagactgga tcgaaaatgg cagctctgat aaatggcagc catcggaaga tatcgcaact    1020
atcgtacgtg acctgtacga cttctccgtt gctcgtgccg actggcgtga aagaacgcg    1080 gttgtattcc cggaccgtcc ggactaccgt ttcgaactta gcgaagacaa tgacgttatt    1140
gccattcatg cagacatgcg tcgcagtgca aaccgtcttg tagaagagtc gatgatcaca    1200
gcgaatatct gtgctggccg cacgcttcgc gataagtttg aaactggcgt gttcaacact    1260
cactctggtc tcaaagcaga gaagattgaa gaagttgtac aattagttga cccagaaggt    1320
acacatggct tcacagcgga cactatcgcg acactggaag ctttgcagc attacgtcgt    1380 tggttgtcta ctcaggaaac ttcatacttg gataaccgca tccgcaagtt ccaggcgtac    1440
agtgaagtcg gcaatcagcc acttcctcac tacgcgatgg gcctagatat ttacgcgact    1500
tggacatctc caattcgtaa atacggcgat atgatcaacc accgtatgct aaaagcggtg    1560
attcttgaca aagaacctgt tcaaaagcct gatgatcaag tcggtgaaga actggcatta    1620
caccgtaagc accacaaaat tgcggagcgt aatgtgtctg actggcttta cgctcgtact    1680
cttgctgagg agccaagcaa acaaactcgc tacatcggtg aaattttcga tatcaatcgt    1740
gctggtgcgc gtgttcgcct gcttgaaaac ggcgccgcgg cgtttattcc tggctcactc    1800
attgttgaca ataaagaacg cattgagtgc aacggtgaca acggtactat ctccatcgat    1860
aaagaagtgg tgtacaagct gggcgatacg ctagaagttg tcttggcaga tgtgaaccag    1920
gaaaaccgca gtttagttgc taaaccgacg caagtgttcg ctgagccgcc aaaagcacag    1980
acggaacaaa cggttgaata a                                              2001
```

<210> SEQ ID NO 20
<211> LENGTH: 1518
<212> TYPE: DNA
<213> ORGANISM: V. natriegens

<400> SEQUENCE: 20

```
atgactgagc aaaaatacat tgttgcccta gaccaaggta cgacaagctc tcgcgcagta    60
attcttgatc acgacgcgaa tatcgtcagc gtcgctcagc gcgaatttac tcagatttat    120
ccgcaagcag gttgggttga gcacgatcca atggaaatct gggcaacaca aagttcaacc    180
ttagttgaag cttttagctaa gtcaggcatc cgcagcgatc aattagcggc tattggcatc    240
acaaaccaac gtgaaacaac gatcgtctgg aacaaagaaa caggtaaacc ggtttacaac    300
gctatcgtct ggcaatgtcg acgcaccgca gaaatttgcg aagacttaaa acgccgcggc    360
ttagaagact acgtacgtga acacacaggc ttagtgcttg acccttactt ctctggcacc    420
aaagtgaagt ggattcttga taacgtcgaa ggtgcccgcg aagatgccga agcaggaaaa    480
ctgttatttg gtacggttga tacctggctg gtgtggaaaa tgacacaagg ccgtgtgcac    540
gtaacggatt acaccaacgc ttcacgtacg atgctattta atatcaatga cctatgttgg    600
gaccaaaagc tgttggatga gttgggtatt cctgcgtcaa tgatgcctga agtaaaacgt    660
tcatctgaaa tctatggcaa aaccaacatt ggtggtaaag gtggtacgcg tattcctatt    720
gcgggtattg ctggtgacca acaagctgcg ctatacggcc agatgtgtgt tgaagcaggt    780
caggcaaaga acacctacgg tacaggttgc ttcttgttga tgaatactgg tcaggaaaaa    840
gtgacgtcta cacacggcct gctgacaaca ctggcatgtg gcccgaaagg tgaaccggca    900
tacgcactag aaggcgcggt gttcatgggt ggtgcgtcta ttcagtggct gcgtgacgag    960
cttaagattc ttaatggcgc agaagactct gaatacttcg caacaaaagt agacacatcc    1020
```

| | |
|---|---|
| aatggtgtgt acgtcgtgcc agcctttact ggccttggcg caccatactg ggatgcgtac | 1080 |
| gcacgaggaa ccattgttgg cttaactcga ggcgttaact caaaccatat tattcgtgcg | 1140 |
| actttggaag gtatcgctta ccaaacccgt gacgtattgg atgcaatgca agccgactct | 1200 |
| ggaatccagt tggctaacct aagagttgac ggcggcgcag tagcaaacaa cttcttgatg | 1260 |
| caattccagt ctgacgtact aaatacgcaa gtacttcgcc ctgaagtcac tgaagtaacc | 1320 |
| gctctgggtg cagcttatct ggcaggctta gcggtaggat attgggatag cctcgatgaa | 1380 |
| ctgcaaggta agcggtaat tgatcgtaca tttgagcctc atgatgatga agagaagcgt | 1440 |
| aatcgtcgct acaaaggctg gaagcgtgca gtgaaatgtg ctcaaacttg gtcagaactt | 1500 |
| cacgacgaag acgattaa | 1518 |

```
<210> SEQ ID NO 21
<211> LENGTH: 1356
<212> TYPE: DNA
<213> ORGANISM: V. natriegens

<400> SEQUENCE: 21
```

| | |
|---|---|
| atggcgactc attttgacta tatctgtatc ggtggcggca gtggcggcat cgcatctgca | 60 |
| aaccgtgcag ccatgtacgg cgcgaaagta gcgctgattg aagcacaaga ccttggtggc | 120 |
| acctgtgtaa acgtaggttg tgtaccaaag aaagtgatgt ggcatggcgc gcaaatcgca | 180 |
| gaagcaatga acctgtacgc ggaagattat gggtttgatg tcgacgtgaa aggtttcgac | 240 |
| tggagcaagc tggtagagag tcgtcaggcg tacattggtc gtattcacca atcttacgac | 300 |
| cgtgttctag gcaacaacaa agtaaatgtt atcaaaggct ttgctaagtt tgttgacgaa | 360 |
| aaaccgttg aagtaaacgg tgaacactac acggccgatc atatcctgat cgctgttggt | 420 |
| ggccgtccaa ctattccaaa catcccgggc gcagaatacg gcatcgattc aaacggcttc | 480 |
| ttcgacctgg ctgagcaacc aaaacgcgta gcggttgttg gtgcaggcta catcgcagtt | 540 |
| gaaatcgcgg gcgtgctaca cgcactaggt acagaaacac acctgttcgt acgtaaagaa | 600 |
| tcgccactgc gtagcttcga tccaatgatc atcgaaacgt tggttgaagt gatggacgct | 660 |
| gaaggtccaa aactgcacac ccattctgta ccaaaagaaa tcattaaaga agcagatggc | 720 |
| actctgactc tgcacctgga aaatggtgaa agccaaaacg ttgaccagct aatctgggca | 780 |
| atcggccgtc acccaacaac agacgctatc aacctagcat caactggcgt tgcaaccaac | 840 |
| gacaaaggct acatcaaggt agacgaatac caagaaacca acgtgaaagg catctactgt | 900 |
| gtaggtgaca tcatggaagg tggtatcgag ctaacacctg tagcagtgaa agcaggtcgt | 960 |
| cagctttctg agcgtttgtt caacaacaag ccaaacgcga agatggatta cgacctcgtt | 1020 |
| ccgactgtcg tattcagcca cccaccaatt ggtaccatcg gtctgactga gccagaagcg | 1080 |
| attgcgaagt acggcgaaga caacgtgaaa gtgtacacct ctggcttcac tgcaatgtac | 1140 |
| accgcggtca ctaagcaccg tcaaccatgt aagatgaagc tggtatgtgc tggtgaagaa | 1200 |
| gaaacggtag tcggcctgca cggcatcggt ttcacggtag acgaaatgat tcagggcttt | 1260 |
| ggcgtagcaa tgaagatggg tgcaactaaa gcagacttcg actctgttgt agcaattcac | 1320 |
| ccaacgggct cggaagagtt cgttactatg agatag | 1356 |

```
<210> SEQ ID NO 22
<211> LENGTH: 1569
<212> TYPE: DNA
<213> ORGANISM: V. natriegens

<400> SEQUENCE: 22
```

```
ttgactgatt ttgctgcgcg actggaaaaa gttgcatcaa acccggaagt atttaaacag      60
tttggacgcg gtgttgagcg tgaaacgtta cgctatcgtc aggatggaca gctagcaaca     120
acacctcatc cagagggatt gggctcagcg ttcacaaacc agtggattac cacggacttt     180
tcagagtcgt tactggagtt cattactccg gtttctcatg atgttccgga gctaatggca     240
caactgaaag atattcatca ctttactcaa actaaatgg gtgaagaaaa aatgtggccg     300
ctttctatgc catgttatgt cgccagtgaa gataatatta atctggcaca gtacggatcg     360
tctaacgcag ctcgaatgaa aacgctctac cgagagggtt tgaaacgccg ttatggcagc     420
ttaatgcaga tcatttcggg tgttcacttc aacttctcgt tcccagaatc gtttgggat      480 gccctatatg gtgagcagga tgaagaggct cgtcaggaaa ccaaatccga tgcctatttt     540
gccctcattc gtaactacta tcgtttttggt tggatgattc cctacttctt tggtgcttcg     600
cctgcgttgt gtggttcgtt tattcaaggc cgagaaacaa gcttaccgtt tgagagcttg     660
ggtggaacgt tattcttacc gaaatcaacg tctttgcgtc tgagcgacct tggttacacg     720
aataatgcac agagttcgct aaagattggc ttcaatagta ttgaccagta tctggaaggt     780
ttaagtgatg ctattcgtcg tccgtcagaa gagttcgcaa aaattggtgt gaaagttgat     840
ggcgagtacc gtcagctcaa ttcgaatgtg ttgcaaatag aaaacgaatt gtacgcgcca     900
attcgcccta aacgagtggc taaaagtggt gagaaaccat cagaagcgtt aaagcgtgcg     960
ggtgttgaat atattgaagt tcgttcattg gacgtgaacc cattcagccc agtaggcata    1020
actgaagagc aagttcgctt cctcgacctg ttcctgactt gggcagcact gtcagactca    1080
gaaccaatgg ataactgtga actggagtgt tggcgtgata actggaacaa agtcattgta    1140
tcgggccgtg aaaaaggctt gatgcttcag atcggttgcc aaggtgagcg cttacctcta    1200
caagagtggg ctcaccgcgt gttgcagat ctacgccaaa ttgctgtgat gatggatgaa     1260
gtgaacggtg ataatgctta ccaagaggtt tgcgataagt taactggctg gattgatgaa    1320
cctgaattga cgacttctgg tcaattgctg gaactgacca aggagttggg cggcttaggt    1380
aaagtaggtt gttcacttgg tatgaagcat cgtgaagata acctgaatca cggctaccag    1440
cattactcac aagaagtgat ggaacaggaa gcgttagcat cggttgaaaa gcaaaagcaa    1500
gcagagctaa gtgacacgat gtcttttgat gacttcctgg aagactattt ttcttattta    1560
aaacaataa                                                             1569

<210> SEQ ID NO 23
<211> LENGTH: 1461
<212> TYPE: DNA
<213> ORGANISM: V. natriegens

<400> SEQUENCE: 23
atggaaaact ttaaacactt acctgagccg tttcgtattc gcgttattga accagtaaaa      60
cgcactacac gtgaatatag agaagaagcg attctaaaag cgggtatgaa ccctttctt     120 ctggatagcg aagatgtgtt tatcgacctt cttaccgata gtggtacagg cgctattacg     180
caagagatgc aagcagccat gttgcgcggc gatgaagcat acagcggcag ccgaagctac     240
catgcacttc aacaggccgt tgaggatatc tttggctacc aatacaccat tccaactcac     300
caaggacgtg gtgcagagca aatttacatt ccggttctga ttaaaaaacg tgagaaagag     360
aaagaactag atagaagcaa gatggttgcg ctgtcgaatt acttttttga caccacacaa    420
ggccatacac agttaaactg ctgtgttgcg aaaaacgttt ataccgaaga agcattcgac    480
```

| | | |
|---|---|---|
| acttcaatcg aagcagactt taaaggtaac tttgatctgg agaaactaga acaggcaatc | 540 | |
| ctagaagctg gcgcagcaaa tgtacctat attgtcagca ccatcacatg taactctgcc | 600 | |
| ggcggccagc cagtatcgct tgctaaccta aaagcggttt atgaaattgg tcagaaatac | 660 | |
| gatattccag tgatcatgga ttcggctcgt tttgccgaga atgcttactt cattcaacaa | 720 | |
| cgtgaagctg gctacgctga ctggtcaatc gaagcaatca ccaaagagag ctacaaatac | 780 | |
| gcggatggtc tggcgatgtc ggcaaagaaa gatgccatgg ttcaaatggg cggcttactt | 840 | |
| tgctttaaag acgattcgtt aatggacgtg tacacggaat gccgcacgct gtgtgttgtt | 900 | |
| caggaaggct ttccgaccta tggtggtctg gaaggtggcg ctatggagcg tcttgccgta | 960 | |
| ggcctttatg atggcatgcg tcaggactgg ctggcatacc gaatcggtca ggttcagtac | 1020 | |
| ctggttgata gctggaagc gattggcatc gtttgtcagc aagcgggtgg ccatgctgcc | 1080 | |
| ttcgttgacg caagcaaact cctgcctcac attcctgcag agcaattccc ggcacatgca | 1140 | |
| ctggcgtgcg agctttataa agtcgctggt attcgagcgg tagaaatagg ctcccttcta | 1200 | |
| ttgggccgag atcctgcgac aggtaaacaa caccgtgtc cggctgaact gcttcgcctt | 1260 | |
| accattcctc gcgctaccta cacacaaacg catatggatt tcattgtcga agcattccag | 1320 | |
| gcggtaaaag aaaatgcagc caatgtaaaa ggtctggact ttacttatga accggaagtt | 1380 | |
| ttacgtcact tcaccgcgcg tctaaaagag gttgagtcag agactcaagc tccatccatc | 1440 | |
| acgacagcag aaacagtata a | 1461 | |

<210> SEQ ID NO 24
<211> LENGTH: 231
<212> TYPE: PRT
<213> ORGANISM: V. natriegens

<400> SEQUENCE: 24

```
Met Lys Tyr Leu Phe Ser Leu Phe Ile Leu Ala Leu Ser Ser Ala Ala
1               5                   10                  15

Val Ala Ala Pro Pro Ser Ser Phe Ser Ala Ala Lys Arg Glu Ala Val
            20                  25                  30

Lys Ile Tyr Gln Asp His Pro Thr Ser Phe Tyr Cys Gly Cys Asp Ile
        35                  40                  45

Gln Trp Gln Gly Lys Lys Gly Leu Pro Asp Leu Ser Ser Cys Gly Tyr
    50                  55                  60

Gln Val Arg Lys Gln Glu Lys Arg Ala Ser Arg Ile Glu Trp Glu His
65                  70                  75                  80

Val Val Pro Ala Trp Gln Phe Gly His Gln Leu Gln Cys Trp Gln Ser
                85                  90                  95

Gly Gly Arg Lys Asn Cys Ser Arg Asn Asp Lys Thr Phe Arg Ser Met
            100                 105                 110

Glu Ala Asp Leu His Asn Leu Thr Pro Ala Ile Gly Glu Val Asn Gly
        115                 120                 125

Asp Arg Ser Asn Tyr Asn Phe Ser Gln Trp Asn Gly Ile Asp Gly Ala
    130                 135                 140

Thr Tyr Gly Arg Cys Glu Val Gln Val Asn Phe Lys Gln Arg Lys Val
145                 150                 155                 160

Met Pro Pro Asp Arg Ala Arg Gly Ser Ile Ala Arg Thr Tyr Leu Tyr
                165                 170                 175

Met Ser Lys Glu Tyr Gly Phe Lys Leu Ser Lys Gln Gln Thr Gln Leu
            180                 185                 190

Met Ser Ala Trp Asn Lys Thr Tyr Pro Ala Asp Lys Trp Glu Cys Glu
```

```
                    195                 200                 205
Arg Asp Lys Arg Ile Ala Lys Val Gln Gly Asn His Asn Pro Phe Val
    210                 215                 220

Gln Glu Ala Cys Arg Ala Leu
225                 230

<210> SEQ ID NO 25
<211> LENGTH: 783
<212> TYPE: PRT
<213> ORGANISM: V. natriegens

<400> SEQUENCE: 25

Met Asn Leu Glu Arg Ser Glu Ser Ile Glu Ile Pro Val Leu Pro Leu
1               5                   10                  15

Arg Asp Val Val Val Tyr Pro His Met Val Ile Pro Leu Phe Val Gly
                20                  25                  30

Arg Glu Lys Ser Ile Ser Cys Leu Glu Thr Ala Met Glu Thr Asn Lys
            35                  40                  45

Gln Val Leu Leu Val Ala Gln Lys Gln Ala Asp Thr Asp Glu Pro Thr
        50                  55                  60

Val Asp Asp Leu Phe Glu Val Gly Thr Val Ala Thr Ile Leu Gln Leu
65                  70                  75                  80

Leu Lys Leu Pro Asp Gly Thr Val Lys Val Leu Val Glu Gly Gln Gln
                85                  90                  95

Arg Ala Lys Ile Asn His Phe Lys Glu Ser Asp Phe Phe Leu Ala Glu
            100                 105                 110

Ala Glu Phe Ile Val Thr Pro Glu Leu Asp Glu Arg Glu Gln Glu Val
        115                 120                 125

Ile Val Arg Ser Ala Ile Asn Gln Phe Glu Gly Phe Ile Lys Leu Asn
    130                 135                 140

Lys Lys Ile Pro Pro Glu Val Leu Thr Ser Leu Asn Gly Ile Asp Glu
145                 150                 155                 160

Ala Ala Arg Leu Ala Asp Thr Ile Ala Ala His Met Pro Leu Lys Leu
                165                 170                 175

Val Asp Lys Gln Gln Val Leu Glu Ile Ile Asp Val Thr Glu Arg Leu
            180                 185                 190

Glu Phe Leu Met Gly Gln Met Glu Ser Glu Ile Asp Leu Leu Gln Val
        195                 200                 205

Glu Lys Arg Ile Arg Gly Arg Val Lys Lys Gln Met Glu Lys Ser Gln
    210                 215                 220

Arg Glu Tyr Tyr Leu Asn Glu Gln Met Lys Ala Ile Gln Lys Glu Leu
225                 230                 235                 240

Gly Glu Met Glu Asp Ala Pro Asp Glu Phe Glu Thr Leu Gln Asn Lys
                245                 250                 255

Ile Glu Glu Ser Lys Met Pro Gln Glu Ala Arg Glu Lys Thr Glu Gln
            260                 265                 270

Glu Leu Gln Lys Leu Lys Met Met Ser Pro Met Ser Ala Glu Ala Thr
        275                 280                 285

Val Val Arg Ser Tyr Ile Asp Trp Met Val Ser Val Pro Trp Ala Lys
    290                 295                 300

Arg Ser Lys Val Lys Lys Asn Leu Ala Lys Ala Glu Glu Ile Leu Asn
305                 310                 315                 320

Glu Asp His Tyr Gly Leu Glu Arg Val Lys Glu Arg Ile Leu Glu Tyr
                325                 330                 335
```

```
Leu Ala Val Gln Asn Arg Ile Asn Lys Leu Lys Gly Pro Ile Leu Cys
                340                 345                 350

Leu Val Gly Pro Pro Gly Val Gly Lys Thr Ser Leu Gly Arg Ser Ile
            355                 360                 365

Ala Ser Ala Thr Gly Arg Lys Tyr Val Arg Met Ala Leu Gly Gly Val
        370                 375                 380

Arg Asp Glu Ala Glu Ile Arg Gly His Arg Arg Thr Tyr Ile Gly Ser
385                 390                 395                 400

Leu Pro Gly Lys Leu Ile Gln Lys Met Ser Lys Val Gly Val Lys Asn
                405                 410                 415

Pro Leu Phe Leu Leu Asp Glu Ile Asp Lys Met Ser Ser Asp Met Arg
            420                 425                 430

Gly Asp Pro Ala Ser Ala Leu Leu Glu Val Leu Asp Pro Glu Gln Asn
        435                 440                 445

Asn Ser Phe Asn Asp His Tyr Leu Glu Val Asp Tyr Asp Leu Ser Asp
        450                 455                 460

Val Met Phe Val Ala Thr Ser Asn Ser Met Asn Ile Pro Gly Pro Leu
465                 470                 475                 480

Leu Asp Arg Met Glu Val Ile Arg Leu Ser Gly Tyr Thr Glu Asp Glu
                485                 490                 495

Lys Leu Asn Ile Ala Lys Arg His Leu Val Asp Lys Gln Leu Lys Arg
            500                 505                 510

Asn Gly Leu Lys Pro Asn Glu Ile Val Ile Glu Asp Ser Ala Ile Val
        515                 520                 525

Gly Ile Ile Arg Tyr Tyr Thr Arg Glu Ala Gly Val Arg Asn Leu Glu
        530                 535                 540

Arg Glu Ile Ser Lys Ile Cys Arg Lys Ala Val Lys Asn Ile Leu Leu
545                 550                 555                 560

Asp Lys Asp Ile Lys Ser Val Thr Val Ser Met Asp Asn Leu Lys Glu
                565                 570                 575

Tyr Leu Gly Val Gln Arg Phe Asp Tyr Gly Lys Ala Asp Glu Ser Asn
            580                 585                 590

Arg Ile Gly Gln Val Thr Gly Leu Ala Trp Thr Glu Val Gly Gly Asp
        595                 600                 605

Leu Leu Thr Ile Glu Thr Gln Ser Met Pro Gly Lys Gly Lys Leu Thr
        610                 615                 620

Gln Thr Gly Ser Leu Gly Asp Val Met Gln Glu Ser Ile Gln Ala Ala
625                 630                 635                 640

Met Thr Val Val Arg Ser Arg Ala Glu Lys Leu Gly Ile Asn Thr Asp
                645                 650                 655

Phe Tyr Glu Lys Lys Asp Ile His Val His Val Pro Glu Gly Ala Thr
            660                 665                 670

Pro Lys Asp Gly Pro Ser Ala Gly Thr Ala Met Cys Thr Ala Leu Val
        675                 680                 685

Ser Ala Leu Thr Gly Asn Pro Val Lys Ala Glu Val Ala Met Thr Gly
        690                 695                 700

Glu Ile Thr Leu Arg Gly Glu Val Leu Pro Ile Gly Gly Leu Lys Glu
705                 710                 715                 720

Lys Leu Leu Ala Ala His Arg Gly Gly Ile Lys Thr Val Leu Ile Pro
                725                 730                 735

Lys Asp Asn Glu Arg Asp Leu Glu Glu Ile Pro Glu Asn Val Ile Ala
            740                 745                 750

Asp Leu Thr Val Ile Pro Val Gln Trp Ile Asp Glu Val Leu Lys Val
```

755                 760                 765
Ala Leu Glu Arg Asp Pro Thr Gly Val Glu Phe Glu Ala Lys Lys
        770                 775                 780

<210> SEQ ID NO 26
<211> LENGTH: 666
<212> TYPE: PRT
<213> ORGANISM: V. natriegens

<400> SEQUENCE: 26

Met Phe Gln Asp Asn Pro Leu Leu Ala Gln Leu Lys Gln Gln Ile Gln
1               5                   10                  15

Glu Asn Leu Pro Lys Lys Glu Gly Ser Ile Lys Ala Thr Asp Lys Gly
            20                  25                  30

Phe Gly Phe Leu Glu Val Asp Ser Lys Thr Ser Phe Phe Ile Pro Pro
        35                  40                  45

Ala Tyr Met Lys Lys Cys Ile His Gly Asp Lys Val Ala Ile Ile
    50                  55                  60

Arg Thr Glu Asn Glu Arg Glu Val Ala Glu Pro Gln Glu Leu Leu Glu
65                  70                  75                  80

Gln Ser Leu Thr Arg Phe Ile Gly Arg Val Lys Met Phe Lys Gly Lys
                85                  90                  95

Leu Asn Val Val Pro Asp His Pro Gln Leu Lys Lys Leu Ser Leu Lys
            100                 105                 110

Ala Lys Leu Lys Lys Gly Gln Lys Pro Asp Asn Phe Asn Glu Gly Asp
        115                 120                 125

Trp Val Val Gly His Leu Ile Arg His Pro Leu Lys Gly Asp Asn Ser
130                 135                 140

Phe Phe Val Glu Ile Ser Glu Lys Ile Thr Asp Ala Asp Asp Lys Ile
145                 150                 155                 160

Ala Pro Trp Trp Val Thr Leu Ala Gln Asn Asp Leu Pro Asn Ser Glu
                165                 170                 175

Pro Ala Gly Ile Glu Asn Trp Glu Leu Lys Asp Asp Ala Glu Leu Asp
            180                 185                 190

Arg Val Asp Leu Thr His Val Pro Phe Val Thr Ile Asp Gly Glu Ser
        195                 200                 205

Thr Lys Asp Met Asp Asp Ala Leu His Ala Lys Lys Thr Glu Ser Gly
    210                 215                 220

Asp Phe Glu Leu Thr Ile Ala Ile Ala Asp Pro Thr Ala Tyr Ile Thr
225                 230                 235                 240

Pro Glu Asp Glu Met Asp Lys Val Ala Arg Glu Arg Gly Tyr Thr Ile
                245                 250                 255

Tyr Leu Pro Gly Arg Asn Ile Pro Met Leu Pro Arg Asp Leu Ala Asp
            260                 265                 270

Asp Leu Cys Ser Leu Ile Glu Gly Glu Thr Arg Pro Ala Leu Cys Cys
        275                 280                 285

Thr Val Ser Val Ser Lys Asp Gly Val Ile Gly Asp Asn Ile Asn Phe
    290                 295                 300

Phe Ala Ala Asn Ile Lys Ser His Ala Arg Leu Ala Tyr Asp His Val
305                 310                 315                 320

Ser Asp Trp Ile Glu Asn Gly Ser Ser Asp Lys Trp Gln Pro Ser Glu
                325                 330                 335

Asp Ile Ala Thr Ile Val Arg Asp Leu Tyr Asp Phe Ser Val Ala Arg
            340                 345                 350

```
Ala Asp Trp Arg Glu Lys Asn Ala Val Val Phe Pro Asp Arg Pro Asp
            355                 360                 365

Tyr Arg Phe Glu Leu Ser Glu Asp Asn Asp Val Ile Ala Ile His Ala
        370                 375                 380

Asp Met Arg Arg Ser Ala Asn Arg Leu Val Glu Glu Ser Met Ile Thr
385                 390                 395                 400

Ala Asn Ile Cys Ala Gly Arg Thr Leu Arg Asp Lys Phe Glu Thr Gly
                405                 410                 415

Val Phe Asn Thr His Ser Gly Leu Lys Ala Glu Lys Ile Glu Glu Val
            420                 425                 430

Val Gln Leu Val Asp Pro Glu Gly Thr His Gly Phe Thr Ala Asp Thr
        435                 440                 445

Ile Ala Thr Leu Glu Gly Phe Ala Ala Leu Arg Arg Trp Leu Ser Thr
        450                 455                 460

Gln Glu Thr Ser Tyr Leu Asp Asn Arg Ile Arg Lys Phe Gln Ala Tyr
465                 470                 475                 480

Ser Glu Val Gly Asn Gln Pro Leu Pro His Tyr Ala Met Gly Leu Asp
                485                 490                 495

Ile Tyr Ala Thr Trp Thr Ser Pro Ile Arg Lys Tyr Gly Asp Met Ile
            500                 505                 510

Asn His Arg Met Leu Lys Ala Val Ile Leu Asp Lys Glu Pro Val Gln
        515                 520                 525

Lys Pro Asp Asp Gln Val Gly Glu Glu Leu Ala Leu His Arg Lys His
530                 535                 540

His Lys Ile Ala Glu Arg Asn Val Ser Asp Trp Leu Tyr Ala Arg Thr
545                 550                 555                 560

Leu Ala Glu Glu Pro Ser Lys Gln Thr Arg Tyr Ile Gly Glu Ile Phe
                565                 570                 575

Asp Ile Asn Arg Ala Gly Ala Arg Val Arg Leu Leu Glu Asn Gly Ala
            580                 585                 590

Ala Ala Phe Ile Pro Gly Ser Leu Ile Val Asp Asn Lys Glu Arg Ile
        595                 600                 605

Glu Cys Asn Gly Asp Asn Gly Thr Ile Ser Ile Asp Lys Glu Val Val
610                 615                 620

Tyr Lys Leu Gly Asp Thr Leu Glu Val Val Leu Ala Asp Val Asn Gln
625                 630                 635                 640

Glu Asn Arg Ser Leu Val Ala Lys Pro Thr Gln Val Phe Ala Glu Pro
                645                 650                 655

Pro Lys Ala Gln Thr Glu Gln Thr Val Glu
            660                 665

<210> SEQ ID NO 27
<211> LENGTH: 505
<212> TYPE: PRT
<213> ORGANISM: V. natriegens

<400> SEQUENCE: 27

Met Thr Glu Gln Lys Tyr Ile Val Ala Leu Asp Gln Gly Thr Thr Ser
1               5                   10                  15

Ser Arg Ala Val Ile Leu Asp His Asp Ala Asn Ile Val Ser Val Ala
            20                  25                  30

Gln Arg Glu Phe Thr Gln Ile Tyr Pro Gln Ala Gly Trp Val Glu His
        35                  40                  45

Asp Pro Met Glu Ile Trp Ala Thr Gln Ser Ser Thr Leu Val Glu Ala
    50                  55                  60
```

```
Leu Ala Lys Ser Gly Ile Arg Ser Asp Gln Leu Ala Ala Ile Gly Ile
 65                  70                  75                  80

Thr Asn Gln Arg Glu Thr Thr Ile Val Trp Asn Lys Glu Thr Gly Lys
                 85                  90                  95

Pro Val Tyr Asn Ala Ile Val Trp Gln Cys Arg Arg Thr Ala Glu Ile
            100                 105                 110

Cys Glu Asp Leu Lys Arg Arg Gly Leu Glu Asp Tyr Val Arg Asp Asn
            115                 120                 125

Thr Gly Leu Val Leu Asp Pro Tyr Phe Ser Gly Thr Lys Val Lys Trp
130                 135                 140

Ile Leu Asp Asn Val Glu Gly Ala Arg Glu Asp Ala Glu Ala Gly Lys
145                 150                 155                 160

Leu Leu Phe Gly Thr Val Asp Thr Trp Leu Val Trp Lys Met Thr Gln
                165                 170                 175

Gly Arg Val His Val Thr Asp Tyr Thr Asn Ala Ser Arg Thr Met Leu
            180                 185                 190

Phe Asn Ile Asn Asp Leu Cys Trp Asp Gln Lys Leu Leu Asp Glu Leu
            195                 200                 205

Gly Ile Pro Ala Ser Met Met Pro Glu Val Lys Arg Ser Ser Glu Ile
210                 215                 220

Tyr Gly Lys Thr Asn Ile Gly Gly Lys Gly Thr Arg Ile Pro Ile
225                 230                 235                 240

Ala Gly Ile Ala Gly Asp Gln Gln Ala Ala Leu Tyr Gly Gln Met Cys
                245                 250                 255

Val Glu Ala Gly Gln Ala Lys Asn Thr Tyr Gly Thr Gly Cys Phe Leu
            260                 265                 270

Leu Met Asn Thr Gly Gln Glu Lys Val Thr Ser Thr His Gly Leu Leu
            275                 280                 285

Thr Thr Leu Ala Cys Gly Pro Lys Gly Glu Pro Ala Tyr Ala Leu Glu
290                 295                 300

Gly Ala Val Phe Met Gly Gly Ala Ser Ile Gln Trp Leu Arg Asp Glu
305                 310                 315                 320

Leu Lys Ile Leu Asn Gly Ala Glu Asp Ser Tyr Phe Ala Thr Lys
                325                 330                 335

Val Asp Thr Ser Asn Gly Val Tyr Val Val Pro Ala Phe Thr Gly Leu
            340                 345                 350

Gly Ala Pro Tyr Trp Asp Ala Tyr Ala Arg Gly Thr Ile Val Gly Leu
            355                 360                 365

Thr Arg Gly Val Asn Ser Asn His Ile Ile Arg Ala Thr Leu Glu Gly
370                 375                 380

Ile Ala Tyr Gln Thr Arg Asp Val Leu Asp Ala Met Gln Ala Asp Ser
385                 390                 395                 400

Gly Ile Gln Leu Ala Asn Leu Arg Val Asp Gly Gly Ala Val Ala Asn
                405                 410                 415

Asn Phe Leu Met Gln Phe Gln Ser Asp Val Leu Asn Thr Gln Val Leu
            420                 425                 430

Arg Pro Glu Val Thr Glu Val Thr Ala Leu Gly Ala Ala Tyr Leu Ala
            435                 440                 445

Gly Leu Ala Val Gly Tyr Trp Asp Ser Leu Asp Glu Leu Gln Gly Lys
            450                 455                 460

Ala Val Ile Asp Arg Thr Phe Glu Pro His Asp Asp Glu Glu Lys Arg
465                 470                 475                 480
```

```
Asn Arg Arg Tyr Lys Gly Trp Lys Arg Ala Val Lys Cys Ala Gln Thr
                    485                 490                 495

Trp Ser Glu Leu His Asp Glu Asp
            500                 505

<210> SEQ ID NO 28
<211> LENGTH: 451
<212> TYPE: PRT
<213> ORGANISM: V. natriegens

<400> SEQUENCE: 28

Met Ala Thr His Phe Asp Tyr Ile Cys Ile Gly Gly Ser Gly Gly
1               5                   10                  15

Ile Ala Ser Ala Asn Arg Ala Ala Met Tyr Gly Ala Lys Val Ala Leu
                20                  25                  30

Ile Glu Ala Gln Asp Leu Gly Gly Thr Cys Val Asn Val Gly Cys Val
                35                  40                  45

Pro Lys Lys Val Met Trp His Gly Ala Gln Ile Ala Glu Ala Met Asn
50                  55                  60

Leu Tyr Ala Glu Asp Tyr Gly Phe Asp Val Asp Val Lys Gly Phe Asp
65                  70                  75                  80

Trp Ser Lys Leu Val Glu Ser Arg Gln Ala Tyr Ile Gly Arg Ile His
                85                  90                  95

Gln Ser Tyr Asp Arg Val Leu Gly Asn Asn Lys Val Asn Val Ile Lys
                100                 105                 110

Gly Phe Ala Lys Phe Val Asp Glu Lys Thr Val Glu Val Asn Gly Glu
                115                 120                 125

His Tyr Thr Ala Asp His Ile Leu Ile Ala Val Gly Gly Arg Pro Thr
                130                 135                 140

Ile Pro Asn Ile Pro Gly Ala Glu Tyr Gly Ile Asp Ser Asn Gly Phe
145                 150                 155                 160

Phe Asp Leu Ala Glu Gln Pro Lys Arg Val Ala Val Val Gly Ala Gly
                165                 170                 175

Tyr Ile Ala Val Glu Ile Ala Gly Val Leu His Ala Leu Gly Thr Glu
                180                 185                 190

Thr His Leu Phe Val Arg Lys Glu Ser Pro Leu Arg Ser Phe Asp Pro
                195                 200                 205

Met Ile Ile Glu Thr Leu Val Glu Val Met Asp Ala Glu Gly Pro Lys
210                 215                 220

Leu His Thr His Ser Val Pro Lys Glu Ile Ile Lys Glu Ala Asp Gly
225                 230                 235                 240

Thr Leu Thr Leu His Leu Glu Asn Gly Glu Ser Gln Asn Val Asp Gln
                245                 250                 255

Leu Ile Trp Ala Ile Gly Arg His Pro Thr Thr Asp Ala Ile Asn Leu
                260                 265                 270

Ala Ser Thr Gly Val Ala Thr Asn Asp Lys Gly Tyr Ile Lys Val Asp
                275                 280                 285

Glu Tyr Gln Glu Thr Asn Val Lys Gly Ile Tyr Cys Val Gly Asp Ile
                290                 295                 300

Met Glu Gly Gly Ile Glu Leu Thr Pro Val Ala Val Lys Ala Gly Arg
305                 310                 315                 320

Gln Leu Ser Glu Arg Leu Phe Asn Asn Lys Pro Asn Ala Lys Met Asp
                325                 330                 335

Tyr Asp Leu Val Pro Thr Val Val Phe Ser His Pro Pro Ile Gly Thr
                340                 345                 350
```

```
Ile Gly Leu Thr Glu Pro Glu Ala Ile Ala Lys Tyr Gly Glu Asp Asn
            355                 360                 365

Val Lys Val Tyr Thr Ser Gly Phe Thr Ala Met Tyr Thr Ala Val Thr
370                 375                 380

Lys His Arg Gln Pro Cys Lys Met Lys Leu Val Cys Ala Gly Glu Glu
385                 390                 395                 400

Glu Thr Val Val Gly Leu His Gly Ile Gly Phe Thr Val Asp Glu Met
                405                 410                 415

Ile Gln Gly Phe Gly Val Ala Met Lys Met Gly Ala Thr Lys Ala Asp
            420                 425                 430

Phe Asp Ser Val Val Ala Ile His Pro Thr Gly Ser Glu Glu Phe Val
                435                 440                 445

Thr Met Arg
    450

<210> SEQ ID NO 29
<211> LENGTH: 522
<212> TYPE: PRT
<213> ORGANISM: V. natriegens

<400> SEQUENCE: 29

Met Thr Asp Phe Ala Ala Arg Leu Glu Lys Val Ala Ser Asn Pro Glu
1               5                   10                  15

Val Phe Lys Gln Phe Gly Arg Gly Val Glu Arg Glu Thr Leu Arg Tyr
            20                  25                  30

Arg Gln Asp Gly Gln Leu Ala Thr Thr Pro His Pro Glu Gly Leu Gly
        35                  40                  45

Ser Ala Phe Thr Asn Gln Trp Ile Thr Thr Asp Phe Ser Glu Ser Leu
    50                  55                  60

Leu Glu Phe Ile Thr Pro Val Ser His Asp Val Pro Glu Leu Met Ala
65                  70                  75                  80

Gln Leu Lys Asp Ile His His Phe Thr Gln Thr Lys Met Gly Glu Glu
                85                  90                  95

Lys Met Trp Pro Leu Ser Met Pro Cys Tyr Val Ala Ser Glu Asp Asn
            100                 105                 110

Ile Asn Leu Ala Gln Tyr Gly Ser Ser Asn Ala Ala Arg Met Lys Thr
        115                 120                 125

Leu Tyr Arg Glu Gly Leu Lys Arg Arg Tyr Gly Ser Leu Met Gln Ile
    130                 135                 140

Ile Ser Gly Val His Phe Asn Phe Ser Phe Pro Glu Ser Phe Trp Asp
145                 150                 155                 160

Ala Leu Tyr Gly Glu Gln Asp Glu Glu Ala Arg Gln Glu Thr Lys Ser
                165                 170                 175

Asp Ala Tyr Phe Ala Leu Ile Arg Asn Tyr Tyr Arg Phe Gly Trp Met
            180                 185                 190

Ile Pro Tyr Phe Phe Gly Ala Ser Pro Ala Leu Cys Gly Ser Phe Ile
        195                 200                 205

Gln Gly Arg Glu Thr Ser Leu Pro Phe Glu Ser Leu Gly Gly Thr Leu
    210                 215                 220

Phe Leu Pro Lys Ser Thr Ser Leu Arg Leu Ser Asp Leu Gly Tyr Thr
225                 230                 235                 240

Asn Asn Ala Gln Ser Ser Leu Lys Ile Gly Phe Asn Ser Ile Asp Gln
                245                 250                 255

Tyr Leu Glu Gly Leu Ser Asp Ala Ile Arg Arg Pro Ser Glu Glu Phe
```

```
            260                 265                 270
Ala Lys Ile Gly Val Lys Val Asp Gly Glu Tyr Arg Gln Leu Asn Ser
            275                 280                 285
Asn Val Leu Gln Ile Glu Asn Glu Leu Tyr Ala Pro Ile Arg Pro Lys
            290                 295                 300
Arg Val Ala Lys Ser Gly Glu Lys Pro Ser Glu Ala Leu Lys Arg Ala
305                 310                 315                 320
Gly Val Glu Tyr Ile Glu Val Arg Ser Leu Asp Val Asn Pro Phe Ser
                325                 330                 335
Pro Val Gly Ile Thr Glu Glu Gln Val Arg Phe Leu Asp Leu Phe Leu
                340                 345                 350
Thr Trp Ala Ala Leu Ser Asp Ser Glu Pro Met Asp Asn Cys Glu Leu
                355                 360                 365
Glu Cys Trp Arg Asp Asn Trp Asn Lys Val Ile Val Ser Gly Arg Glu
            370                 375                 380
Lys Gly Leu Met Leu Gln Ile Gly Cys Gln Gly Glu Arg Leu Pro Leu
385                 390                 395                 400
Gln Glu Trp Ala His Arg Val Phe Ala Asp Leu Arg Gln Ile Ala Val
                405                 410                 415
Met Met Asp Glu Val Asn Gly Asp Asn Ala Tyr Gln Glu Val Cys Asp
                420                 425                 430
Lys Leu Thr Gly Trp Ile Asp Glu Pro Glu Leu Thr Thr Ser Gly Gln
                435                 440                 445
Leu Leu Glu Leu Thr Lys Glu Leu Gly Gly Leu Gly Lys Val Gly Cys
            450                 455                 460
Ser Leu Gly Met Lys His Arg Glu Asp Asn Leu Asn His Gly Tyr Gln
465                 470                 475                 480
His Tyr Ser Gln Glu Val Met Glu Gln Glu Ala Leu Ala Ser Val Glu
                485                 490                 495
Lys Gln Lys Gln Ala Glu Leu Ser Asp Thr Met Ser Phe Asp Asp Phe
            500                 505                 510
Leu Glu Asp Tyr Phe Ser Tyr Leu Lys Gln
            515                 520

<210> SEQ ID NO 30
<211> LENGTH: 486
<212> TYPE: PRT
<213> ORGANISM: V. natriegens

<400> SEQUENCE: 30

Met Glu Asn Phe Lys His Leu Pro Glu Pro Phe Arg Ile Arg Val Ile
1               5                   10                  15
Glu Pro Val Lys Arg Thr Thr Arg Glu Tyr Arg Glu Glu Ala Ile Leu
            20                  25                  30
Lys Ala Gly Met Asn Pro Phe Leu Leu Asp Ser Glu Asp Val Phe Ile
        35                  40                  45
Asp Leu Leu Thr Asp Ser Gly Thr Gly Ala Ile Thr Gln Glu Met Gln
    50                  55                  60
Ala Ala Met Leu Arg Gly Asp Glu Ala Tyr Ser Gly Ser Arg Ser Tyr
65                  70                  75                  80
His Ala Leu Gln Gln Ala Val Glu Asp Ile Phe Gly Tyr Gln Tyr Thr
                85                  90                  95
Ile Pro Thr His Gln Gly Arg Gly Ala Glu Gln Ile Tyr Ile Pro Val
            100                 105                 110
```

```
Leu Ile Lys Lys Arg Glu Lys Glu Lys Glu Leu Asp Arg Ser Lys Met
        115                 120                 125

Val Ala Leu Ser Asn Tyr Phe Phe Asp Thr Thr Gln Gly His Thr Gln
130                 135                 140

Leu Asn Cys Cys Val Ala Lys Asn Val Tyr Thr Glu Glu Ala Phe Asp
145                 150                 155                 160

Thr Ser Ile Glu Ala Asp Phe Lys Gly Asn Phe Asp Leu Glu Lys Leu
            165                 170                 175

Glu Gln Ala Ile Leu Glu Ala Gly Ala Asn Val Pro Tyr Ile Val
                180                 185                 190

Ser Thr Ile Thr Cys Asn Ser Ala Gly Gly Gln Pro Val Ser Leu Ala
        195                 200                 205

Asn Leu Lys Ala Val Tyr Glu Ile Gly Gln Lys Tyr Asp Ile Pro Val
        210                 215                 220

Ile Met Asp Ser Ala Arg Phe Ala Glu Asn Ala Tyr Phe Ile Gln Gln
225                 230                 235                 240

Arg Glu Ala Gly Tyr Ala Asp Trp Ser Ile Glu Ala Ile Thr Lys Glu
                245                 250                 255

Ser Tyr Lys Tyr Ala Asp Gly Leu Ala Met Ser Ala Lys Lys Asp Ala
            260                 265                 270

Met Val Gln Met Gly Gly Leu Leu Cys Phe Lys Asp Asp Ser Leu Met
        275                 280                 285

Asp Val Tyr Thr Glu Cys Arg Thr Leu Cys Val Val Gln Glu Gly Phe
290                 295                 300

Pro Thr Tyr Gly Gly Leu Glu Gly Gly Ala Met Glu Arg Leu Ala Val
305                 310                 315                 320

Gly Leu Tyr Asp Gly Met Arg Gln Asp Trp Leu Ala Tyr Arg Ile Gly
                325                 330                 335

Gln Val Gln Tyr Leu Val Asp Lys Leu Glu Ala Ile Gly Ile Val Cys
            340                 345                 350

Gln Gln Ala Gly Gly His Ala Ala Phe Val Asp Ala Ser Lys Leu Leu
        355                 360                 365

Pro His Ile Pro Ala Glu Gln Phe Pro Ala His Ala Leu Ala Cys Glu
        370                 375                 380

Leu Tyr Lys Val Ala Gly Ile Arg Ala Val Glu Ile Gly Ser Leu Leu
385                 390                 395                 400

Leu Gly Arg Asp Pro Ala Thr Gly Lys Gln His Pro Cys Pro Ala Glu
                405                 410                 415

Leu Leu Arg Leu Thr Ile Pro Arg Ala Thr Tyr Thr Gln Thr His Met
            420                 425                 430

Asp Phe Ile Val Glu Ala Phe Gln Ala Val Lys Glu Asn Ala Ala Asn
        435                 440                 445

Val Lys Gly Leu Asp Phe Thr Tyr Glu Pro Glu Val Leu Arg His Phe
450                 455                 460

Thr Ala Arg Leu Lys Glu Val Glu Ser Glu Thr Gln Ala Pro Ser Ile
465                 470                 475                 480

Thr Thr Ala Glu Thr Val
                485
```